United States Patent [19]
Adams et al.

[11] Patent Number: 5,874,265
[45] Date of Patent: Feb. 23, 1999

[54] METHODS AND COMPOSITIONS FOR THE PRODUCTION OF STABLY TRANSFORMED FERTILE MONOCOT PLANTS AND CELLS THEREOF

[75] Inventors: Thomas R. Adams, No. Stonington; Sheryl A. Chambers, Groton; Richard J. Daines, Ledyard; William J. Gordon-Kamm; Albert P. Kausch, both of Stonington; Peggy G. Lemaux, Mystic; Catherine J. Mackey, Old Lyme, all of Conn.; Mary L. Mangano, Westerly, R.I.; James V. O'Brien, Mystic, Conn.; Thomas B. Rice, Waterford, Conn.; T. Michael Spencer, Mystic, Conn.; William G. Start, North Stonington, Conn.; Nancy G. Willetts, Niantic, Conn.

[73] Assignee: Dekalb Genetics Corporation, DeKalb, Ill.

[21] Appl. No.: 446,931

[22] Filed: May 23, 1995

Related U.S. Application Data

[63] Continuation of Ser. No. 565,844, Aug. 9, 1990, Pat. No. 5,550,318, which is a continuation-in-part of Ser. No. 513,298, Apr. 17, 1990, abandoned.

[51] Int. Cl.⁶ .......................... C12N 15/00; C12N 15/82; A01H 1/06; A01H 4/00
[52] U.S. Cl. ..................... 435/172.3; 435/172.1; 435/287; 935/52; 935/67; 800/205; 800/DIG. 55; 800/DIG. 58
[58] Field of Search ........................ 800/205; 435/172.3, 435/172.1, 242, 424, 430, 430.1; 935/52, 67

[56] References Cited

U.S. PATENT DOCUMENTS

| | | | |
|---|---|---|---|
| 4,370,160 | 1/1983 | Ziemelis | 71/117 |
| 4,399,216 | 8/1983 | Axel et al. | 435/6 |
| 4,535,060 | 8/1985 | Comai | 435/172.3 |
| 4,559,301 | 12/1985 | Turner et al. | 435/76 |

(List continued on next page.)

FOREIGN PATENT DOCUMENTS

| | | | |
|---|---|---|---|
| B-80893/87 | 12/1988 | Australia | C12N 15/00 |
| 2032443 | 12/1990 | Canada | C12N 15/87 |
| 0 126 537 A2 | 11/1984 | European Pat. Off. | A61K 9/52 |
| 0 131 623 B1 | 1/1985 | European Pat. Off. | C12N 15/11 |

(List continued on next page.)

OTHER PUBLICATIONS

Datta, S.K., et al., "Genetically Engineered Fertile Indica–Rice Recovered from Protoplasts", *Bio/Technology*, 8, 736–740 (Aug. 1990).

Hooykaas–Van Slogteren, G.M.S., et al., "Expression of Ti Plasmid Genes in Monocotyledonous Plants Infected with *Agrobacterium tumefaciens*", *Nature*, 311, 763–764 (Oct. 25, 1984).

Ranch, J.P., et al., "Expression of 5–Methyltryptophan Resistance in Plants Regenerated from Resistant Cell Lines of *Datura innoxia*", *Plant Physiol.*, 71, 136–140 (1983).

Armstrong, C.L., et al., "Genetic and Cytogenetic Variation in Plants Regenerated from Organogenic and Friable, Embryogenic Tissue Cultures in Maize", *Crop Sci.*, 28, 363–369 (1988).

(List continued on next page.)

*Primary Examiner*—Gary Benzion
*Attorney, Agent, or Firm*—Schwegman, Lundberg, Woessner, and Kluth, P.A.

[57] ABSTRACT

This invention relates to a method for the production of stable, genetically transformed cereal plants, other than maize or rice, that comprise an exogenous DNA expressing phosphinothricin acetyl transferase to impart resistance to phosphinothricin in said cereal plants. Cereal plants within the scope of the method include, but are not limited to, wheat, barley and oats. The invention also pertains to a method of breeding said transgenic cereal plants with a either a non-transgenic plant or a transgenic plant, and the obtention of fertile transgenic plants and seed therefrom.

31 Claims, 24 Drawing Sheets

5,874,265
Page 2

U.S. PATENT DOCUMENTS

| | | | |
|---|---|---|---|
| 4,559,302 | 12/1985 | Ingolia | 435/172.3 |
| 4,581,847 | 4/1986 | Hibberd et al. | 47/58 |
| 4,634,665 | 1/1987 | Axel et al. | 435/68 |
| 4,642,411 | 2/1987 | Hibberd et al. | 800/1 |
| 4,665,030 | 5/1987 | Close | 435/240 |
| 4,666,844 | 5/1987 | Chen | 435/240 |
| 4,683,202 | 7/1987 | Mullis | 435/91 |
| 4,727,028 | 2/1988 | Santerre et al. | 435/240.2 |
| 4,743,548 | 5/1988 | Crossway et al. | 435/172.3 |
| 4,761,373 | 8/1988 | Anderson et al. | 435/172.3 |
| 4,806,483 | 2/1989 | Wang | 435/240.49 |
| 4,940,835 | 7/1990 | Shah et al. | 800/205 |
| 4,971,908 | 11/1990 | Kishore et al. | 435/172.1 |
| 5,001,060 | 3/1991 | Peacock et al. | 435/172.3 |
| 5,004,863 | 4/1991 | Umbeck | 800/205 |
| 5,015,580 | 5/1991 | Christou et al. | 435/172.3 |
| 5,034,322 | 7/1991 | Rogers et al. | 435/172.3 |
| 5,049,500 | 9/1991 | Arnizen et al. | 435/172.3 |
| 5,094,945 | 3/1992 | Comai | 435/172.3 |
| 5,110,732 | 5/1992 | Benfey et al. | 435/172.3 |
| 5,134,074 | 7/1992 | Gordon et al. | 435/240.4 |
| 5,145,777 | 9/1992 | Goodman et al. | 435/172.3 |
| 5,164,310 | 11/1992 | Smith et al. | 435/172.3 |
| 5,177,010 | 1/1993 | Goldman et al. | 435/172.2 |
| 5,187,073 | 2/1993 | Goldman et al. | 435/172.3 |
| 5,187,267 | 2/1993 | Comai et al. | 536/23.1 |
| 5,188,642 | 2/1993 | Shah et al. | 47/58 |
| 5,188,958 | 2/1993 | Moloney et al. | 435/240.4 |
| 5,215,912 | 6/1993 | Hoffman | 435/240.4 |
| 5,250,515 | 10/1993 | Fuchs et al. | 514/12 |
| 5,254,799 | 10/1993 | De Greve et al. | 800/205 |
| 5,258,300 | 11/1993 | Glassman et al. | 435/240 |
| 5,268,463 | 12/1993 | Jefferson | 536/23.7 |
| 5,272,072 | 12/1993 | Kaneko et al. | 435/172.3 |
| 5,276,268 | 1/1994 | Strauch et al. | 800/205 |
| 5,290,924 | 3/1994 | Last et al. | 536/24.1 |
| 5,302,523 | 4/1994 | Coffee et al. | 435/172.1 |
| 5,350,689 | 9/1994 | Shillito et al. | 435/240.47 |
| 5,352,605 | 10/1994 | Fraley et al. | 435/240.4 |
| 5,371,003 | 12/1994 | Murry et al. | 435/172.3 |
| 5,380,831 | 1/1995 | Adang et al. | 536/23.71 |
| 5,405,765 | 4/1995 | Vasil et al. | 435/172.3 |
| 5,436,393 | 7/1995 | Rocha-Sosa et al | 800/205 |
| 5,484,956 | 1/1996 | Lundquist et al. | 800/205 |
| 5,489,520 | 2/1996 | Adams et al. | 435/172.3 |
| 5,500,365 | 3/1996 | Fischoff et al. | 435/240.4 |
| 5,508,468 | 4/1996 | Lundquist et al. | 800/205 |
| 5,545,545 | 8/1996 | Gengenbach et al. | 435/172.3 |
| 5,550,318 | 8/1996 | Adams et al. | 800/205 |
| 5,554,798 | 9/1996 | Lundquist et al. | 800/205 |
| 5,561,236 | 10/1996 | Leemans et al. | 800/205 |
| 5,565,347 | 10/1996 | Fillatti et al. | 435/172.3 |
| 5,567,600 | 10/1996 | Adang et al. | 536/23.71 |
| 5,567,862 | 10/1996 | Adang et al. | 800/205 |
| 5,578,702 | 11/1996 | Adang et al. | 530/350 |
| 5,589,616 | 12/1996 | Hoffman | 800/205 |
| 5,591,616 | 1/1997 | Hiei et al. | 435/172.3 |
| 5,595,733 | 1/1997 | Carswell et al. | 424/93.21 |
| 5,596,131 | 1/1997 | Horn et al. | 800/205 |
| 5,623,067 | 4/1997 | Vandekerckhove et al. | 536/24.1 |
| 5,641,664 | 6/1997 | D'Halluin et al. | 435/172.3 |
| 5,641,876 | 6/1997 | McElroy et al. | 536/24.1 |

FOREIGN PATENT DOCUMENTS

| | | | |
|---|---|---|---|
| 0 141 373 A3 | 5/1985 | European Pat. Off. | A01G 7/00 |
| 0 154 204 A2 | 9/1985 | European Pat. Off. | C12N 15/00 |
| 0 160 390 A2 | 11/1985 | European Pat. Off. | A01H 15/00 |
| 0 174 791 A2 | 3/1986 | European Pat. Off. | C12N 15/00 |
| 0 189 707 A2 | 8/1986 | European Pat. Off. | C12N 15/00 |
| 0 193 259 A1 | 9/1986 | European Pat. Off. | C12N 15/00 |
| 0 202 668 A2 | 11/1986 | European Pat. Off. | C12N 5/02 |
| 0 204 549 A2 | 12/1986 | European Pat. Off. | C12N 15/00 |
| 0 242 236 A1 | 10/1987 | European Pat. Off. | C12N 15/00 |
| 0 242 246 A1 | 10/1987 | European Pat. Off. | C12N 15/00 |
| 0 299 552 A1 | 1/1988 | European Pat. Off. | C12N 15/00 |
| 0 257 472 A2 | 3/1988 | European Pat. Off. | C12N 15/00 |
| 0 262 971 A2 | 4/1988 | European Pat. Off. | A01H 1/02 |
| 0 270 356 A2 | 6/1988 | European Pat. Off. | C12N 15/00 |
| 0 271 408 A2 | 6/1988 | European Pat. Off. | C12N 15/00 |
| 0 275 069 A2 | 7/1988 | European Pat. Off. | C12N 15/00 |
| 0 280 400 A2 | 8/1988 | European Pat. Off. | A01C 1/06 |
| 0 282 164 A2 | 9/1988 | European Pat. Off. | C12N 5/00 |
| 0 289 479 A2 | 11/1988 | European Pat. Off. | C12N 15/00 |
| 0 290 395 A2 | 11/1988 | European Pat. Off. | C12N 15/00 |
| 0 292 435 A1 | 11/1988 | European Pat. Off. | C12N 15/00 |
| 0 301 749 A2 | 2/1989 | European Pat. Off. | C12N 15/00 |
| 0 331 855 A2 | 9/1989 | European Pat. Off. | C12M 3/00 |
| 0 334 539 A2 | 9/1989 | European Pat. Off. | C12N 15/00 |
| 0 335 528 A2 | 10/1989 | European Pat. Off. | C12N 15/00 |
| 0 348 348 A2 | 12/1989 | European Pat. Off. | A01N 65/00 |
| 0 353 908 A2 | 2/1990 | European Pat. Off. | C12N 15/29 |
| 0 359 617 A2 | 3/1990 | European Pat. Off. | C12N 15/53 |
| 0 360 750 A2 | 3/1990 | European Pat. Off. | C12N 15/29 |
| 0 385 962 A1 | 9/1990 | European Pat. Off. | C12N 15/82 |
| 0 442 174 A1 | 8/1991 | European Pat. Off. | C12N 15/82 |
| 0 485 970 A3 | 5/1992 | European Pat. Off. | . |
| 0 589 110 A1 | 3/1994 | European Pat. Off. | . |
| 37 38 874 A1 | 11/1988 | Germany | A01H 1/06 |
| 40 13 099 A1 | 10/1991 | Germany | . |
| 61-134343 | 6/1986 | Japan | . |
| 8 801 444 | 1/1990 | Netherlands | C12N 15/87 |
| 2 159 173 | 11/1985 | United Kingdom | C12N 15/00 |
| 85/01856 | 5/1985 | WIPO | . |
| 85/02972 | 7/1985 | WIPO | A01C 1/06 |
| 87/04181 | 7/1987 | WIPO | C12N 1/00 |
| 87/05629 | 9/1987 | WIPO | C12N 15/00 |
| 89/04371 | 5/1989 | WIPO | C12P 21/00 |
| 89/10396 | 11/1989 | WIPO | C12N 5/00 |
| 89/11789 | 12/1989 | WIPO | A01H 1/00 |
| 89/12102 | 12/1989 | WIPO | C12N 15/00 |
| 90/01869 | 3/1990 | WIPO | A01H 1/04 |
| 90/02801 | 3/1990 | WIPO | C12N 15/32 |
| WO 91/02071 | 2/1991 | WIPO | . |
| WO 91/10725 | 7/1991 | WIPO | . |
| WO 92/12250 | 7/1992 | WIPO | . |
| 92/17580 | 10/1992 | WIPO | C12N 5/10 |
| 93/06220 | 4/1993 | WIPO | C12N 15/82 |
| WO 93/07278 | 4/1993 | WIPO | . |
| 93/09237 | 5/1993 | WIPO | C12N 15/82 |
| WO 93/19190 | 9/1993 | WIPO | . |

OTHER PUBLICATIONS

Dure III, L., et al., "Common Amino Acid Sequence Domains Among the LEA Proteins of Higher Plants", *Plant Molecular Biology*, 12, 475–486 (1989).

Hong, B., et al., "Cloning and Characterization of a cDNA Encoding a mRNA Rapidly–Induced by ABA in Barley Aleurone Layers", *Plant. Mol. Biol.*, 11, 495–506 (1988).

Lemaux, P.G., et al., "Selection of Stable Transformants from Maize Suspension Cultures Using the Herbicide Bialaphos", *J. Cell. Biochem.*, vol. 14e, Abstract R230, 304 (Mar. 31, 1990).

Mundy, J., et al., "Abscisic Acid and Water–Stress Induce the Expression of a Novel Rice Gene", *The EMBO Journal*, 7, 2279–2286 (1988).

Piatkowski, D., et al., "Characterization of Five Abscisic Acid–Responsive cDNA Clones Isolated from the Desiccation–Tolerant Plant *Craterostigma plantagineum* and Their Relationship to Other Water–Stress Genes", *Plant Physiol.*, 94, 1682–1688 (1990).

Yamaguchi–Shinozaki, K., et al., "Molecular Cloning and Characterization of 9 cDNAs for Genes That Are Responsive to Desiccation in *Arabidopsis thaliana*: Sequence Analysis of One cDNA Clone That Encodes a Putative Transmembrane Channel Protein", *Plant Cell Physiol.*, 33, 217–224 (1992).

Beermann et al., "Tyrosinase as a marker for transgenic mice," *Nucleic Acids Research*, 19(4):958, 1991.

Gordon–Kamm et al., "Transformation of Maize Cells and Regeneration of Fertile Transgenic Plants," *The Plant Cell*, 2:603–618, Jul., 1990.

Perl et al., "Bacterial Dihydrodipicolinate Synthase and Desensitized Aspartate Kinase: Two Novel Selectable Markers for Plant Transformation," *Bio/Technology*, 11:715–718, Jun., 1993.

Perlak et al., "Modification of the coding sequence enhances plant expression of insect control protein genes," *Proc. Natl. Acad. Sci. USA*, 88:3324–3328, Apr., 1991.

Spencer et al., "Segregation of transgenes in maize," *Plant Molecular Biology*, 18:201–210, 1992.

Sugiyama et al., "Use of the Tyrosinase Gene from Streptomyces to Probe Promoter Sequences for *Escherichia coli*," *Plasmid*, 23:237–241, 1990.

Wong et al., "*Arabidopsis thaliana* small subunit leader and transit peptide enhance the expression of *Bacillus thuringiensis* proteins in transgenic plants," *Plant Molecular Biology*, 20:81–93, 1992.

Botterman, J., et al., "Engineering Herbicide Resistance in Plants", *Trends in Genetics*, vol. 4, No. 8, 219–222, (Aug. 1988).

DeBlock et al. "Engineering Herbicide Resistnce in Plants by Expression of a Detoxifying Enzyme" EMBO, 8, 2513–2518, 1987.

Vasil "Transgenic Cereals Becoming A Reality" Bio/Technology 8, 797, Sep. 1990.

Sanford "The Biolistic Process" Trends Biotechnology, 6, 229–302, 1990.

International Search Report, PCT/US 97/00978, mailed Jul. 22, 1997.

International Search Report, PCT/US 97/00983, mailed Jun. 12, 1997.

Atanassova, R., et al., "A 126 bp Fragment of Plant Histone Gene Promoter Confers Preferential Expression in Meristems of Transgenic Arabidopsis", *The Plant J.*, 2, 291–300 (1992).

Brignon, P., et al., "Nuclease Sensitivity and Functional Analysis of a Maize Histone H3 Gene Promoter", *Plant Mol. Biol.*, 22, 1007–1015 (1993).

McCue, K.F., et al., "Drought and Salt Tolerance: Towards Understanding and Application", *TIBTECH*, 8, 358–362 (Dec. 1990).

Rathinasabapathi, B., et al., "Metabolic Engineering of Glycine Betaine Synthesis: Plant Betaine Aldehyde Dehydrogenases Lacking Typical Transit Peptides are Targeted to Tobacco Chloroplasts Where They Confer Betaine Aldehyde Resistance", *Planta*, 193, 155–162 (1994).

Vasil, V., et al., "Regeneration of Plants from Embryogenic Suspension Culture Protoplasts of Wheat (*Triticum aestivum* L.)", *Bio/Technology*, 8, 429–434 (May 1990).

"Biotechnica Applies for Field Test of Genetically Engineered Corn", *Genetic Technology News*, 10, 4 (Mar. 1990).

"Bullets Transform Plant Cells", *Agricell Report*, 9, 5 (Jul. 1987).

Catalog, Handbook of Fine Chemicals, Aldrich Chemical Co., p. 508 (1988).

"Chipping Away At Old Weed Enemies", *Prairie Farmer*, 162, 34 (Feb. 20, 1990).

"Corn Transformers Multiply", *Bio/Technol.*, 8, 490 (Jun. 1990).

"Cornell U. Gene Gun Hits Biotech Bullseye", *Agriculture Technology*, p. 13.

"Dalapon", *Merck Index, 11th Edition*, S. Budavae, (ed.), Merck and Co., pp. 405–406 (1989).

"Dekalb Researchers Produce Fertile Corn Plants with Foreign Genes", *ARI Newsletter* (Oct.–Nov. 1990).

Dialog Search of Japanese Patent No. 61–134,343 (1986).

"Gene Guns Succeed in Altering Corn", *Biotechnology News*, p. 2 (Apr. 1990).

"Genetic Engineering Advance Announced for Corn Plants", *Investor's Daily* (Apr. 19, 1990).

"Genetically Engineered Corn: Breakthrough Brings Market Closer", *Genetic Technology News*, 8–11 (Oct. 1990).

"Herbicide–Resistant Corn", *CT Academy of Science and Engineering, Case Reports*, 5, 6 (1990).

"Keystone Crops", *Agricultural Genetics Report* (Mar./Apr. 1990).

Patent Family Record for Australian Patent AU–B–87/80893.

"Plant Science Research, Inc. Achieves Successful Transformation of Corn", *Genetic Engineering News*, 10, 3 (Mar. 1990).

"Shotgunning DNA into Cells", *Genetic Engineering News* (Jul.–Aug. 1987).

Specification of U.S. Patent Application, Serial No. 07/205,155, entitled "Stable Transformation of Plant Cells," 1–29 (Jun. 10, 1988).

"Sticky Ends", *Genetic Engineering News*, 10, 1 (May 1990).

"Teams from USDA/Monsanto and DeKalb Genetically Engineer Corn", *Genetic Technology News*, 10 (May 1990).

"Two Teams Succeed in Putting Foreign Genes in Corn Plants", *Genetic Engineering Letter*, 10, 3 (Apr. 24, 1990).

"USDA Approves Field Test for BioTechnica's Genetically Engineered Corn", *Genetic Techonology News*, 10, 6 (Jul. 1990).

Adang, M.J., et al., "Characterized Full–Length and Truncated Plasmid Clones of the Crystal Protein of *Bacillus thuringiensis* subsp. *kurstaki* HD–73 and Their Toxicity to *Manduca sexta*", *Gene*, 36, 289–300 (1985).

Ahokas, H., "Electrophorectic Transfection of Cereal Grains with Exogenous Nucleic Acid", Abstracts, Soc. Biochem. Biophys. Microbio. Fen., Biotieteen Paivat (Bioscience Days), Technical University of Helsinki, Espoo, Finland, p. 2, (1989).

Ahokas, H., "Transfection of Germinating Barley Seed Electrophoretically with Exogenous DNA", *Theor. Appl. Genet.*, 77, 469–472 (1989).

Altenbach, S.B., et al., "Cloning and Sequence Analysis of a cDNA Encoding a Brazil Nut Protein Exceptionally Rich in Methionine", *Plant Mol. Biol.*, 8, 239–250 (1987).

Altenbach, S.B., et al., "Enhancement of the Methionine Content of Seed Proteins by the Expression of a Chimeric Gene Encoding a Methionine–Rich Protein in Transgenic Plants", *Plant. Mol. Biol.*, 13, 513–522 (1989).

Ampe, C., et al., "The Amino–Acid Sequence of the 2S Sulphur–Rich from Seed of Brazil Nut (*Bertholletia excelsa* H.B.K.)", *Eur. J. Biochem.*, 159, 597–604 (1986).

Andrews, D.L., et al., "Characterization of the Lipid Acyl Hydrolase Activity of the Major Potato (*Solanum tuberosum*) Tuber Protein, Patatin, by Cloning and Abundant Expression in a Baculovirus Vector", *Biochem. J.*, 252, 199–206 (1988).

Armstrong, C.L., et al., "Establishment and Maintenance of Friable, Embryogenic Maize Callus and the Involvement of L–Proline", *Planta*, 164, 207–214 (1985).

Armstrong, C.L., et al., "Genetic and Cytogenetic Variation in Plants Regenerated from Organogenic and Friable, Embryogenic Tissue Cultures in Maize", *Biol. Abstracts*, 85, Abstract No. 117662, p. 22 (1988).

Barker, R.F., et al., "Nucleotide Sequence of the T–DNA Region from the *Agrobacterium tumefaciens* Octopine Ti Plasmid pTi15955", *Plant Mol. Biol.*, 2, 335–350 (1983).

Benner, M.S., et al., "Genetic Anlysis of Methionine–Rich Storage Protein Accumulation in Maize", *Theor. Appl. Genet.*, 78, 761–767 (1989).

Bevan, M., et al., "A Chimaeric Antibiotic Resistance Gene as a Selectable Marker for Plant Cell Transformation", *Nature*, 304, 184–187 (1983).

Bevan, M., et al., "Structure and Transcription of the Nopaline Synthase Gene Region of T–DNA", *Nuc. Acids Res.*, 11, 369–385 (1983).

Binns, A.N., "Agrobacterium–Mediated Gene Delivery and the Biology of Host Range Limitations", *Physiologia Plantarum*, 79, 135–139 (1990).

Bishop, J.E., "Two Teams Place Genes into Corn", *The Wall Street Journal*, B1 (Apr. 1990).

Booy, G., et al., "Attempted Pollen–Mediated Transformation of Maize", *J. Plant Physiol.*, 135, 319–324 (1989).

Boulton, M.I., et al., "Specificity of Agrobacterium–Mediated Delivery of Maize Streak Virus DNA to Members of the Gramineae", *Plant Mol. Biol.*, 12, 31–40 (1989).

Boyer, J.S., "Water Deficits and Photosynthesis", In: *Water Deficits and Plant Growth*, vol. IV, Kozlowski, T.T., (ed.), Academic Press, New York, pp. 153–190 (1976).

Brill, W.J. "Agricultural Microbiology", *Scientific American*, 245, 199–215 (Sep. 1981).

Buchanan–Wollaston, V., et al., "Detoxification of the Herbicide Dalapon by Transformed Plants", *J. Cell. Biochem.*, 13D, Abstract No. M503, p. 330 (1989).

Callis, J., et al., "Introns Increase Gene Expression in Cultured Maize Cells", *Genes and Development*, 1, 1183–1200 (1987).

Cao, J., et al., "Transformation of Rice and Maize Using the Biolistic Process", In: *Plant Gene Transfer*, Lamb, C.J., et al., (eds.), Wiley–Liss, Inc. New York, pp. 21–23 (1990).

Carpita, N.C., "The Biochemistry of Growing Cell Walls", In: *Physiology of Cell Expansion During Plant Growth*, Cosgrove, D.J. et al., (eds.), Am. Soc. Plant Physiologists, Rockville, MD, pp. 28–100 (1987).

Chandler, V.L., et al., "Two Regulatory Genes of the Maize Anthocyanin Pathway are Homologous: Isolation of B Utilizing R Genomic Sequences", *The Plant Cell*, 1, 1175–1183 (1989).

Charest, P.J. et al., "Factors Affecting the Use of Chloramphenicol Acetyltransferase as a Marker for Brassica Genetic Transformation", *Plant Cell Reports*, 7 628–631 (1989).

Chourey, P.S., et al., "Callus Formation from Protoplasts of a Maize Cell Culture", *Theor. Appl. Genet.*, 59, 341–344 (1981).

Christou, P., et al., "Cotransformation Frequencies of Foreign Genes in Soybean Cell Cultures", *Theor. Appl. Genet.* 79, 337–341 (1990).

Christou, P., et al., "Opine Synthesis in Wild–Type Plant Tissue", *Plant Physiol.*, 82, 218–221 (1986).

Christou, P., et al., "Soybean Genetic Engineering — Commercial Production of Transgenic Plants", *Trends in Biotechnology*, 8, 145–151 (1990).

Christou, P., et al., "Stable Transformation of Soybean Callus by DNA–Coated Gold Particles", *Plant Physiol.*, 87, 671–674 (1988).

Chu, C., et al., "Establishment of an Efficient Medium for Another Culture of Rice Through Comparative Experiments on the Nitrogen Sources", *Scientia Sinica*, 18, 659–668 (Sep.–Oct. 1975).

Clark, B., "Biotech Advance in Corn: Gunslinging Researchers Fire Marker Genes in to Corn", *AG Consultant*, 46, 12 (Jul. 1990).

Cocking, F., et al., "Gene Transfer in Cereals", *Science*, 236, 1259–1262 (1987).

Coe, E.H., et al., "The Genetics of Corn", In: *Corn and Corn Improvement*, 2nd Edition, Sprague, G.F., (ed.), American Society of Agronomy, Inc., Madison, WI, p. 138 (1977).

Comai, L., et al., "Expression in Plants of a Mutant aroA Gene from *Salmonella typhimurium* Confers Tolerance to Glyphosate", *Nature*, 317, 741–744 (Oct. 1985).

Creissen, G., et al., "Agrobacterium– and Microprojectile–Mediated Viral DNA Delivery into Barley Microspore–Derived Cutures", *Plant Cell Reports*, 8, 680–683 (Apr. 1990).

Crossway, A., et al., "Integration of Foreign DNA Following Microinjection of Tobacco Mesophyll Protoplasts", *Mol. Gen. Genet.*, 202, 179–185 (1986).

Darvill, A., et al., "The Primary Cell Walls of Flowering Plants", In: *The Plant Cell*, vol. 1 of The Biochemistry of Plants Series, Tolbert, N.E., (ed.), Academic Press, New York, pp. 91–162 (1980).

Dauce–Le Reverend, B., et al., "Improvement of *Escherichia coli* Strains Overproducing Lysine Using Recombinant DNA Techniques", *European J. Appl. Microbiol. Biotechnol.*, 15, 227–231 (1982).

De Greef, W., et al., "Evaluation of Herbicide Resistance in Transgenic Crops under Field Conditions", *Bio/Technology*, 7, 61–64 (1989).

Dekeyser, R.A., et al., "Evaluation of Selectable Markers for Rice Transformation", *Plant Physiol.*, 90, 217–223 (1989).

Dekeyser, R.A., et al., "Transient Gene Expression in Intact and Organized Rice Tissues", *The Plant Cell*, 2, 591–602 (Jul. 1990).

DeWald, S.G., et al., "Plant Regeneration from Inbred Maize Suspensions", VIIth International Congress on Plant Tissue and Cell Culture, Amsterdam, The Netherlands, Abstract No. A1–36, p. 12, (Jun. 24–29, 1990).

DeWet, J.J., et al., "Exogenous Gene Transfer in Maize (*Zea mays*) using DNA–treated Pollen", In: *The Experimental Manipulation of Ovule Tissues*, Chapman, G.P. et al., (eds.), Longman, New York, pp. 197–209 (1985).

DeWet, J.R., et al., "Cloning of Firefly Luciferase cDNA and the Expression of Active Luciferase in *Escherichia coli*", *Proc. Nat. Acad. Sci. USA*, 82, 7870–7873 (1985).

Donn, G., et al., "Stable Transformation of Maize with a Chimaeric, Modified Phosphinothricin–Acetyltranferase Gene from *Streptomyces viridochromogenes*", Abstracts, VIIth International Congress on Plant Tissue Cell Culture, Amsterdam, The Netherlands, Abstract No. A2–38, p. 53 (Jun. 24–29, 1990).

Evans, D.A., et al., "Somaclonal Variation — Genetic Basis and Breeding Applications", *Trends Genet.*, 5, 46–50 (1989).

Flavell, R., et al., "Prospects for Transforming Monocot Crop Plants", *Nature*, 307, 108–109 (Jan. 12, 1984).

Fransz, P., et al, "Cytodifferentiation During Callus Initiation and Somatic Embryogenesis in *Zea mays* L.", Ph.D. Thesis, University of Wageningen Press, The Netherlands (1988).

Freeling, J.C., et al., "Development Potentials of Maize Tissue Cultures", *Maydica*, XXI, 97–112 (Jul. 1977).

Freiberg, B., "More Researchers Discover Corn Transformation Technology", *AG Biotechnology News*, p. 26 (1990).

Fromm, M.E., et al., "Expression of Genes Transfected into Monocot and Dicot Plant Cells by Electroportion", *Proc. Nat. Acad. Sci. USA*, 82, 5824–5828 (1985).

Fromm, M.E., et al., "Inheritance and Expression of Chimeric Genes in the Progeny of Transgenic Maize Plants", *Bio/Technology*, 8, 833–839 (1990).

Fromm, M.E., et al., "Stable Transformation of Maize after Gene Transfer by Electroporation", *Nature*, 319, 791–793 (1986).

Fry, S.C., "Introduction to the Growing Cell Wall", In: *The Growing Plant Cell Wall: Chemical and Metabolic Analysis*, Longman Scientific and Technical, New York, pp. 1–5, 102–109 (1988).

Geiser, M., et al., "The Hypervariable Region on the Genes Coding for Entomophatogenic Crystal Proteins of *Bacillus thuringiensis*: Nucleotide Sequence of the kurhd1 gene of subsp. *kurstaki* HDI", *Gene*, 48, 109–118 (1986).

Goff, S.A., et al., "Plant Regeneration of Anthocyanin Biosynethic Genes Following Transfer of B Regulatory Genes into Maize Tissues", *EMBO J.*, 9, 2517–2522 (1990).

Goodman, R.M., et al., "Gene Transfer in Crop Improvement", *Science*, 236, 48–54 (Apr. 3, 1987).

Gordon–Kamm, W.J., et al., "Stable Transformation of Embryonic Maize Cultures by Microprojectile Bombardment", *J. Cellular Biochem.*, 13D, Abstract No. M122, p. 259 (1989).

Gould, O., et al., "Shoot Tip Culture as a Potential Transformation System", Abstracts, Beltwide Cotton Production Research Conferences, New Orleans, LA, p. 91 (1988).

Graves, A., et al., "The Transformation of *Zea mays* Seedlings with *Agrobacterium tumefaciens*", *Plant Mol. Biol.*, 7, 43–50 (1986).

Green, C., et al., "Plant Regeneration in Tissue Cultures of Maize", *Crop Sci.*, 15, 417–421 (1975).

Green, C., et al., "Plant Regeneration in Tissue Cultures of Maize", In: *Maize for Biological Research*, Sheridan, W.F., (ed.), Plant Molecular Biology Association, Charlottesville, VA, pp. 367–372 (1982).

Green, C., et al., "Somatic Cell Genetic Systems in Corn", In: *Advances in Gene Technology: Molecular Genetics of Plants and Animals*, Downey, K., (ed.), Academic Press, Inc., New York, pp. 147–157 (1983).

Grimsley, N., et al., "DNA Transfer from Agrobacterium to *Zea mays* or Brassica by Agroinfection is Dependent on Bacterial Virulence Functions", *Mol. Gen. Genet.*, 217, 309–316 (1989).

Gritz, L., et al., "Plasmid–Encoded Hygromycin B Resistance: The Sequence of Hygromycin B Phosphotransferase Gene and Its Expression in *Escherichia coli* and *Saccharomyces cerevisiae*", *Gene*, 25, 179–188 (1983).

Guerineau, F., et al., "Sulfonamide Resistance Gene for Plant Transformation", *Plant Molecular Biology*, 15, 127–136 (1990).

Guilley, H., et al., "Transcription of Cauliflower Mosaic Virus DNA: Detection of Promoter Sequences, and Characterization of Transcripts", *Cell*, 30, 763–773 (Oct. 1982).

Gunset, G., "Corn Farmers See Economic, Environment Gold in Designer Genes", *Chicago Tribune* (Jan. 21, 1991).

Gunset, G., "Genetic Advance May Transform Corn", *Chicago Tribune* (Apr. 19, 1990).

Hallauer, A.R., et al., "Corn Breeding", In: *Corn and Corn Improvement*, 3rd Edition, Sprague, G.F., et al., (eds.), American Society of Agronomy, Inc., Madison, WI, pp. 463–564 (1988).

Haughn, G.W., "Transformation with a Mutant Arabidopsis Acetolactate Synthase Gene Renders Tobacco Resistant to Sulfonylurea Herbicides", *Mol. Gen. Genet.*, 211, 266–271 (1988).

Hauptmann, R.M. et al., "Evaluation of Selectable Markers for Obtaining Stable Transformants on the Gramineae", *Plant Physiol.*, 86, 602–606 (1988).

Herrera–Estrella, L., et al., "Use of Reporter Genes to Study Gene Expression in Plant Cells", In: *Plant Molecular Biology Manual B1*, Kluwer Academic Publishers, Dordrecht, Belgium, pp. 1–22 (1988).

Hoffman, L.M., et al., "A Modified Storage Protein is Synthesized, Processed, and Degraded in the Seeds of Transgenic Plants", *Plant Mol. Biol.*, 11, 717–729 (1988).

Hoffman, L.M., et al., "Synthesis and Protein Body Deposition of Maize 15–kd Zein in Transgenic Tobacco Seeds", *EMBO J.*, 6, 3213–3221 (1987).

Hofte, H., et al., "Insecticidal Crystal Proteins of *Bacillus thuringiensis*", *Microbiol. Rev.*, 53, 242–255 (Jun. 1989).

Hooykaas, P.J.J., "Transformation of Plant Cell via Agrobacterium", *Plant Mol. Biol.*, 13, 327–336 (1989).

Horn, M., et al., "Transgenic Plants of Orchard Grass (*Dactylis glomerata* L.) from Protoplasts", *Chem. Abstracts*, 110, Abstract No. 89869a, p. 208 (1989).

Horn, M., et al., "Transgenic Plants of Orchardgrass (*Dactylis glomerta* L.) from Protoplasts", *Plant Cell Reports*, 7, 469–472 (1988).

Huang, Y., et al., "Factors Influencing Stable Transformation of Maize Protoplasts by Electroporation", *Plant Cell. Tissue and Organ Culture*, 18, 281 (1989).

Imbrie–Milligan, C., et al., "Microcallus Growth from Maize Protoplasts", *Planta*, 171, 58–64 (1987).

Jahne, A., et al., "Regeneration of Fertile Plants from Protoplasts Derived from Embryogenic Cell Suspensions of Barley (*Hordeum vulagare* L.)", *Plant Cell Rep.*, 10, 1–6 (1991).

Jaynes, J.M., et al., "Plant Protein Improvement by Genetic Engineering: Use of Synthetic Genes", *Trends in Biotechnology*, 4, 314–320 (Dec. 1986).

Jefferson, R.A., "Assaying Chimeric Genes in Plants: The GUS Gene Fusion System", *Plant Mol. Biol. Rep.*, 5, 387–405 (1987).

Jefferson, R.A., et al., "Beta–Glucuronidase from *Escherichia coli* as a Gene–Fusion Marker", *Proc. Nat. Acad. Sci. USA*, 83, 8447–8451 (1986).

Jefferson, R.A., et al., "GUS Fusions: Beta–Glucuronidase as a Sensitive and Versatile Gene Fusion Marker in Higher Plants", *EMBO J.*, 6, 3901–3907 (1987).

Johri, M.M., et al., "Genetic Approaches to Meristem Organization", In: *Maize for Biological Research*, Sheridan, W.F., (ed.), Plant Molecular Biology Association, Charlottesville, VA, pp. 301–310 (1982).

Jones, H., et al., "Recent Advances in Plant Electroporation", *Oxford Surveys of Plant Molecular and Cell Biology*, 4, 347–357 (1987).

Jones, H., et al., "Transient Gene Expression in Electroporated Solanum Protoplasts", *Plant Mol. Biol.*, 13, 503–511 (1989).

Kaeppler, H.F., et al., "Silicon Carbide Fiber–Mediated DNA Delivery into Plant Cells", *Plant Cell Rep.*, 9, 415–418 (1990).

Kamo, K., et al., "Establishment and Characterization of Long–Term Embryonic Maize Callus and Cell Suspension Cultures", *Plant Sci.*, 45, 111–117 (1986).

Kamo, K., et al., "Regeneration of *Zea mays* L. from Embryongenic Callus", *Bot. Gaz.*, 146, 327–334 (1985).

Kao, K.N., et al., "Nutritional Requirements for Growth of *Vicia hajastana* Cells and Protoplasts at a Very Low Population Density in Liquid Media", *Planta*, 126, 105–110 (1978).

Kartha, K., et al, "Transient Expression of Chloramphenicol Acetyl Transferase (CAT) Gene in Barley Cell Cultures and Immature Embryos Through Microprojectile Bombardment", *Plant Cell. Rep.*, 8, 429–432 (1989).

Kay, R., et al., "Duplication of CaMV 35S Promoter Sequences Creates a Strong Enhancer for Plant Genes", *Science*, 236, 1299–1302 (Jun. 5, 1987).

Kirihara, J., et al., "Differential Expression of a Gene for a Methionine–Rich Storage Protein in Maize", *Mol. Gen. Genet.*, 211, 477–484 (1988).

Kirihara, J., et al., "Isolation and Sequence of a Gene Encoding a Methionine–Rich 10–kDa Zein Protein from Maize", *Gene*, 71, 359–370 (1988).

Klein, T.M. et al., "Factors Influencing Gene Delivery into *Zea mays* Cells by High Velocity Microprojectiles", *Bio/Technology*, 6, 559–563 (1988).

Klein, T.M., et al., "Genetic Transformation of Maize Cell by Particle Bombardment and the Influence of Methylation on Foreign Gene Expression", In: *Gene Manipulation in Plant Improvement II*, Gustafson, J.P., (ed.), Plenum Press, New York, pp. 265–266 (1990).

Klein, T.M., et al., "Genetic Transformation of Maize Cells by Particle Bombardment", *Plant Physiology*, 91, 440–444 (1989).

Klein, T.M., et al., "High–Velocity Microprojectiles for Delivering Nucleic Acids to Living Cells", *Nature*, 327, 70–73 (1987).

Klein, T.M., et al., "Regulation of Anthocyanin Biosynthetic Genes Introduced into Intact Maize Tissues by Microprojectiles", *Pro. Nat. Acad. Sci. USA*, 86, 6681–6685 (Sep. 1989).

Klein, T.M., et al., "Transfer of Foreign Genes into Intact Maize Cells with High–Velocity Microprojectiles", *Proc. Nat. Acad. Sci. USA*, 85, 4305–4309 (1988).

Kozak, M., "Compilation and Analysis of Sequences from the Translational Start Site in Eukaryotic mRNAs", *Nuc. Acids Res.*, 12, 857–872 (1984).

Kozak, M., "Point Mutations Define a Sequence Flanking the AUG Initiator Codon that Modulates Translation by Eukaryotic Ribosomes", *Cell*, 44, 283–292 (1986).

Kreitlow, B., "Genetic Engineering 'Breakthrough' Disputed", *Cedar Rapids Gazette* (Apr. 20, 1990).

Kuhlemeier, C., et al., "Regulation of Gene Expression in Higher Plants", *Ann. Rev. Plant Physiol.*, 38, 234–239 (1987).

Lazzeri, P., et al., "In Vitro Genetic Manipulation of Cereals and Grasses", *Adv. Cell Culture*, 6, 291–293 (1988).

Lee, J.S., et al., "Gene Transfer into Intact Cells of Tobacco by Electroporation", *Korean J. Genetics*, 11, 65–72 (1989).

Levitt, J., "Growth Regulators", In: *Introduction to Plant Physiology*, The C.V. Mosby Company, St. Louis, MO, p. 241 (1969).

Lindsey, K., et al., "Electroporation of Cells", *Physiol. Plant.*, 79, 168–172 (1990).

Lindsey, K., et al., "Stable Transformation of Sugarbeet Protoplasts by Electroporation", *Plant Cell Rep.*, 8, 71–74 (1989).

Lindsey, K., et al., "The Permeability of Electroporated Cells and Protoplasts of Sugar Beet", *Planta*, 172, 346–355 (1987).

Lindsey, K., et al., "Transient Gene Expression in Electroporated Protoplasts and Intact Cells of Sugar Beet", *Plant Mol. Biol.*, 10, 43–52 (1987).

Looker D., "Dekalb Claims Success in Effort to Alter Genetic Makeup of Corn", *Des Moines Register* (Apr. 19, 1990).

Lorz, H., et al., "Advances in Tissue Cultures and Progess Towards Genetic Transformation of Cereals", *Plant Breeding*, 100, 1–25 (1988).

Lu, C., et al., "Improved Efficiency of Somatic Embryogenesis and Plant Regeneration on Tissue Cultures of Maize (*Zea mays* L.)", *Theor. Appl. Genet.*, 66, 285–289 (1983).

Lu, C., et al., "Somatic Embryogenesis in *Zea mays* L.", *Theor. Appl. Genet*, 62, 109–112 (1982).

Ludwig, S., et al., "A Regulatory Gene as a Novel Visible Marker for Maize Transformation", *Science*, 247, 449–450 (1990).

Ludwig, S., et al., "High Frequency Callus Formation from Maize Protoplasts", *Theor. Appl. Genet.*, 71, 344–350 (1985).

Ludwig, S., et al., "Lc, a Member of the Maize R Gene Family Responsible for Tissue–Specific Anthocyanin Production, Encodes a Protein Similar to Transcriptional Activators and Contains the myc–Homology Region", *Proc. Nat. Acad. Sci. USA*, 86, 7092–7096 (1989).

Ludwig, S., et al., "Maize R Gene Family: Tissue–Specific Helix–Loop–Helix Proteins", *Cell*, 62, 849–851 (1990).

Lutcke, H., et al., "Selection of AUG Initiation Codons Differs in Plants and Animals", *EMBO J.*, 6, 43–48 (1987).

Masumura, T., et al., "cDNA Cloning of an mRNA Encoding a Sulfer–Rich 10 kDa Prolamin Polypeptide in Rice Seeds", *Plant Mol. Biol.*, 12, 123–130 (1989).

McCabe, D.E. et al., "Stable Transformation of Soybean (*Glycine max*) by Particle Acceleration", *Bio/Technology*, 6, 923–926 (1988).

McDaniel, C., et al., "Cell–Lineage Patterns in the Shoot Apical Meristem of the Germinating Maize Embryo", *Planta*, 175, 13–22 (1988).

Meadows, C., et al., "Characterization of Cells and Protoplasts of the B73 Maize Cell Line", *Plant Sci. Lett.*, 28, 337–348 (1982–1983).

Mendel, R., et al., "Delivery of Foreign Genes to Intact Barley Cell by High–Velocity Microprojectiles", *Theor. Appl. Genet.*, 78, 31–34 (1989).

Messing, J., "Corn Storage Protein: A Molecular Genetic Model", Division of Energy Biosciences — Summaries of FY 1990 Activities, U.S. Department of Energy, Washington, D.C., Abstract No. 135, p. 70 (1990).

Milborrow, B.V., "Abscisic Acid and Other Hormones", In: *The Physiology and Biochemistry of Drought Resistance in Plants*, Paleg, L.G., et al., (eds.), Academic Press, New York, pp. 347–388 (1981).

Moffat, A.S., "Corn Transformed", *Science*, 249, 630 (Aug. 10, 1990).

Morikawa, H., et al., "Gene Transfer into Intact Plant Cells by Electroporation Through Cell Walls and Membranes", *Gene*, 41, 121–124 (1986).

Morocz, S., et al., "An Improved System to Obtain Fertile Regenerants via Maize Protoplasts Isolated From a Highly Embryogenic Suspension Culture", *Theor. Appl. Genet.*, 80, 721–726 (1990).

Morocz, S., et al., "Two Approaches to Rendering *Zea mays* L. Applicable to Tissue Culture Manipulations", Abstracts, VIIth International Congress on Plant Tissue and Cell Culture, A1–102, Amsterdam, The Netherlands, Abstract No. 209, p. 190 (1990).

Murakami, T., et al., "The Bialaphos Biosynthetic Genes of *Streptomyces hygroscopicus*: Molecular Cloning and Characterization of the Gene Cluster", *Mol. Gen. Genet.*, 205, 42–50 (1986).

Murashige, T., et al., "A Revised Medium for Rapid Growth and Bio Assays with Tobacco Tissue Cultures", *Physiol. Plant.*, 15, 473–497 (1962).

Murphy, H.L., "New Dekalb–Pfizer Seed Cheif to Harvest R & D Breakthroughs", *Crain's Business Weekly*, 38–39 (1990).

Murray, E.E., et al., "Codon Usage in Plant Genes", *Nuc. Acids Res.*, 17, 477–498 (1989).

Nelson, R.S., "Virus Tolerance, Plant Growth and Field Performance of Transgenic Tomato Plants Expressing Coat Protein from Tobacco Mosaic Virus", *Bio/Technology*, 6, 403–409 (Apr. 1988).

Nelson, T., "New Horses for Monocot Gene Jockeys", *The Plant Cell*, 2, 589 (1990).

Neuffer, M.G., "Growing Maize for Genetic Purposes", In: *Maize for Biological Research*, Sheridan, W.F., (ed.), Plant Molecular Biology Association, Charlottesville, VA, pp. 19–30 (1982).

Odell, J., et al., "Identification of DNA Sequences Required for Activity of the Cauliflower Mosaic Virus 35S Promoter", *Nature*, 313, 810–811 (1985).

Ohta, Y., et al., "Gene Manifestation of Exogenous DNA Applied to Self–Propagating Stigma (Gene Action Revealed in the Msub1 and Msub2 Generations from Self–Pollination Applying Exogenous DNA)", *Jap. J. Breed.*, 30, 184–185 (1980).

Ohta, Y., et al., "High–Efficiency Genetic Transformation of Maize by a Mixture of Pollen and Exogenous DNA", *Proc. Nat. Acad. Sci. USA*, 83, 715–719 (1986).

Ozias–Akins, P., et al., "In Vitro Regeneration and Genetic Manipuation of Grasses", *Physiol. Plant.*, 73, 565–569 (1988).

Ozias–Akins, P., et al., "Progress and Limitations in the Culture of Cereal Protoplasts", *Trends in Biotechnology*, 2, 119–123 (1984).

Parker, W.B., et al., "Selection and Characterization of Sethoxydim–Tolerant Maize Tissue Cultures", *Plant Physiol.*, 92, 1220–1225 (1990).

Paszkowski, J., et al., "Direct Gene Transfer to Plants", *The EMBO Journal*, 3, 2717–2722 (1984).

Pederson, K., et al., "Sequence Analysis and Characterization of a Maize Gene Encoding a High–Sulfur Zein Protein of Msubr 15,000", *J. Biol. Chem.*, 261, 6279–6284 (1986).

Phillips, R.L., et al., "Cell/Tissue Culture and In Vitro Manipulation", In: *Corn and Corn Improvement*, 3rd Edition, Sprague, G.F., et al. (eds.), American Society of Agronomy, Inc., Madison, WI, 345–387 (1988).

Phillips, R.L., et al., "Elevated Protein–Bound Methionine in Seeds of a Maize Line Resistant to Lysine Plus Threonine", *Cereal Chem.*, 62, 213–218 (1985).

Poehlman, J.M., "Backcross Breeding", In: *Breeding Field Crops*, 3rd Edition, AVI Publishing Company, Inc., Westport, CT, 203–206 (1988).

Poehlman, J.M., "Breeding Corn (Maize)", In: *Breeding Field Crops*, 3rd Edition, AVI Publishing Co., Westport, CT, 477–481 (1986).

Poehlman, J.M., "Breeding Corn (Maize)", In: *Breeding Field Crops*, 3rd Edition, AVI Publishing Co., Westport, CT, 452 (1986).

Poehlman, J.M., "Breeding Corn (Maize)", In: *Breeding Field Crops*, 3rd Edition, AVI Publishing Co., Westport, CT, 469–470 (1988).

Potrykus, I., "Gene Transfer to Cerals: An Assessment", *Bio/Technology*, 8, 535–542 (Jun. 1990).

Potrykus, I., "Gene Transfer to Cereals: An Assessment", *Trends in Biotechnology*, 7, 269–273 (Oct. 1989).

Potrykus, I., "Gene Transfer to Plants: Assessment and Perspectives", *Physiol. Plant.*, 79, 125–134 (1990).

Potrykus, I., et al., "Callus Formation from Cell Culture Protoplasts of Corn (*Zea mays* L.)", *Theor. Appl. Genet.*, 54, 209–214 (1979).

Potrykus, I., et al., "Callus Formation from Stem Protoplasts of Corn (*Zea mays* L.)", *Mol. Gen. Genet.*, 156, 347–350 (1977).

Potrykus, I., et al., "Direct Gene Transfer to Cells of a Graminaceous Monocot", *Mol. Gen. Genet.*, 199, 184–188 (1985).

Potter, H., et al., "Enhancer–Dependent Expression of Human Kappa Immunoglobulin Genes Introduced into Mouse Pre–B Lymphocytes by Electroporation", *Proc. Nat. Acad. Sci. USA*, 81, 7161–7165 (1984).

Prioli, L.M., et al., "Plant Regeneration and Recovery of Fertile Plants from Protoplasts of Maize (*Zea mays* L.)", *Bio/Technology*, 7, 589–594 (Jun. 1989).

Puite, K.J., et al., "Electrofusion,1 a Simple and Reproducible Technique in Somatic Hybridization of *Nicotiana plumbaginifolia* mutants", *Plant Cell Rep.*, 4, 274–276 (1985).

Rhodes, C.A., "Corn: From Protoplasts to Fertile Plants", *Bio/Technology*, 7, 548 (Jun. 1989).

Rhodes, C.A., et al., "Genetically Transformed Maize Plants from Protoplasts", *Science*, 240, 204–207 (Apr. 1988).

Rhodes, C.A., et al., "Plant Regeneration from Protoplasts Isolated from Embryogenic Maize Cell Cultures", *Bio/Technology*, 6, 56–60 (Jan. 1988).

Richaud, R., et al., "Chromosomal Location and Nucleotide Sequence of the *Escherichia coli* dapA Gene", *Biol. Abstracts*, 82, Abstract No. 3396, p. 391 (1986).

Richaud, F., et al., "Chromosomal Location and Nucleotide Sequence of the *Escherichia coli* dapA Gene", *Journal of Bacteriology*, 166, 297–300 (Apr. 1986).

Robbins–Roth, C., et al., "They Make it Happen in Biotech", *Bioworld*, 30–36 (Nov.–Dec. 1990).

Robertson, D.S., "Loss of Mu Mutator Activity when Active Mu Systems are Transferred to Inbred Lines", *Maize Genetics Coop. Newsletter*, 60, 10 (1986).

Ross, M.C., et al., "Transient and Stable Transgenic Cells and Calli of Tobacco and Maize Following Microprojectile Bombardment", *J. Cell. Biochem.*, 13D, Abstract No. M149, p. 268 (1989).

Sahi, S.V., et al., "Metabolites in Maize Which Affect Virulance Induction in *Agrobacterium tumefaciens*", *Plant Physiol., Supplement*, Abstract No. 514, p. 86 (1989).

Sanford, J.C., "Biolistic Plant Transformation", *Physiol. Plant.*, 79, 206–209 (1990).

Sanford, J.C., et al., "Attempted Pollen–Mediated Plant Transformation Employing Genomic Donor DNA", *Theor. Appl. Genet.*, 69, 571–574 (1985).

Sanford, J.C., et al., "Delivery of Substances into Cells and Tissues Using a Particle Bombardment Process", *Particulate Sci. Technol.*, 5, 27–37 (1987).

Sass, J.E. "Morphology: Development of the Caryopsis", In: *Corn and Corn Improvement*, 2nd Edition, Sprague, G.F., (ed.), American Society of Agronomy, Inc. Madison, WI, p. 89, 98 (1977).

Schmidt, A., et al., "Media and Environmental Effects of Phenolics Production from Tobacco Cell Cultures", *Chem. Abstracts.*, 110, Abstract No. 230156z, p. 514 (1989).

Shigekawa, K., et al., "Electroporation of Eukaryotes and Prokaryotes: A General Approach to the Introduction of Macromolecules into Cells", *BioTechniques*, 6, 742–751 (1988).

Shillito, R.D., et al., "High Efficiency Direct Gene Transfer to Plants", *Bio/Technology*, 3, 1099–1103 (1985).

Shillito, R.D., et al., "Regeneration of Fertile Plants from Protoplasts of Elite Inbred Maize", *Bio/Technology*, 7, 581–587 (Jun. 1989).

Shimamoto, K., et al., "Fertile Transgenic Rice Plants Regenerated from Transformed Protoplasts", *Nature*, 338, 274–278 (1989).

Shotwell, M.A., et al., "The Biochemistry and Molecular Biology of Seed Storage Proteins", In: *The Biochemistry of Plants*, vol. 15, Marcus, A., (ed.), Academic Press, Inc., San Diego, CA, pp. 297–345 (1989).

Smith, R., et al., "Shoot Apex Explant for Transformation", *Plant Physiol. (Suppl.)*, 86, Abstract No. 646, p. 108 (1988).

Soberon, X., et al., "Construction and Characterization of New Cloning Vehicles. IV. Deletion Derivatives of pBR322 and pBR325", *Gene*, 9, 287–305 (1980).

Spencer, T.M., et al., "Bialaphos Selection of Stable Transformations from Maize Cell Culture", *Theor. Appl. Genet.*, 79, 625–631 (May 1990).

Spencer, T.M., et al., "Fertile Transgenic Maize", Abstracts, 7th Annual Meeting of the Mid–Atlantic Plant Molecular Biology Society, University of Maryland, College Park, MD, p. 30 (Aug. 16–17, 1990).

Spencer. T.M., et al., "Selection of Stable Transformants from Maize Suspension Cultures using the Herbicide Bialophos", Poster Presentation, FASEB Plant Gene Expression Conference, Copper Mountain, CO (Aug. 8, 1989).

Sprague, G.F., et al., "Corn Breeding", In: *Corn and Corn Improvement*, 2nd Edition, Sprague, G.F., (ed.), American Society of Agronomy, Inc., Madison, WI, pp. 305, 320–323 (1977).

Steimel, D., "Corn Breeders Stalk Perfect Hybrid", *Rockford Register Star*, (Aug. 6, 1990).

Steimel, D., "New Gun Will Custom–Design Corn: Breeding Technique Expected by End of 90's Will Let Crop Grow Without Pesticides or Much Water", (Apr. 1990).

Thompson, C., et al., "Characterization of the Herbicide–Resistance Gene bar from *Streptomyces hygroscopicus*", *EMBO J.*, 6, 2519–2523 (1987).

Tomes, D.T., "Status of Corn Transformation", 26th Annual Corn Breeders School, Meeting Proceedings, University of Illinois, Champaign, IL, p. 7–8 (Feb. 26–27, 1990).

Tomes, D.T., et al., "Transgenic Tobacco Plants and Their Progeny Derived by Microprojectile Bombardment of Tobacco Leaves", *Plant Mol. Biol.*, 14, 261–268 (Feb. 1990).

Twell, D., et al., "Transient Expression of Chimeric Genes Delivered into Pollen by Microprojectile Bombardment", *Plant Physiol.*, 91, 1271–1274 (1989).

Ulian, E., et al., "Transformation of Plants via the Shoot Apex", *In Vitro Cell. Dev. Biol.*, 9, 951–954 (1988).

Usami, S., et al., "Absence in Monocotyledonous Plants of the Diffusable Plant Factors including T–DNA Circularization and vir Gene Expression in Agrobacterium", *Mol. Gen. Genet.*, 209, 221–226 (1987).

Vasil, I.K., et al., "Culture of Protoplasts Isolated from Embryogenic Cell Suspension Cultures of Sugarcane and Maize", *IAPTC Abstracts*, p. 443 (1986).

Vasil, V., et al., "Isolation and Maintenance of Embryogenic Cell Suspension Cultures of Gramineae", In: *Cell Culture and Somatic Cell Genetics of Plants*, vol. I, Academic Press, pp. 152–158 (1984).

Vasil, V., et al., "Plant Regeneration from Friable Embryonic Callus and Cell Suspension Cultures of *Zea mays* L.", *J. Plant Physiol.*, 124, 399–408 (1986).

Walbot, V., et al., "Molecular Genetics of Corn", In: *Corn and Corn Improvement*, 3rd Edition, Sprague, G.F., et al., (eds.), American Society of Agronomy, Inc., Madison, WI, pp. 389–430 (1988).

Waldron, C., et al., "Resistance to Hygromycin B", *Plant Mol. Biol.*, 5, 103–108 (1985).

Wang, Y., et al., "Transient Expression of Foreign Genes in Rice, Wheat, and Soybean Cells Following Particle Bombardment", *Plant Mol. Biol.*, 11, 433–439 (1988).

Weising, K., et al., "Foreign Genes in Plants: Transfer, Structure, Expression and Applicatioins", *Ann. Rev. Genet.*, 22, 421–478 (1988).

White, J., et al., "A Cassette Containing the bar Gene of *Streptomyces hygroscopicus*: a Selectable Marker for Plant Transformation", *Nuc. Acids Res.*, 18, 1062 (1989).

Whitely, H.R., et al., "The Molecular Biology of Parasporal Crystal Body Formation in *Bacillus thuringiensis*", *Ann. Rev. Microbiol.*, 40, 549–576 (1986).

Yang, H., et al., "Production of Kanamycin Resistant Rice Tissues Following DNA Uptake into Protoplasts", *Plant Cell Rep.*, 7, 421–425 (1988).

Yanisch–Perron, C., et al., "Improved M13 Phage Cloning Vectors and Host Strains: Nucleotide Sequences of the M13mp18 and pUC19 Vectors", *Gene*, 33, 103–119 (1985).

Yugari, Y., et al., "Coordinated End–Product Inhibition in Lysine Synthesis in *Escherichia coli*", *Biochem. Biophys. Acta*, 62, 612–614 (1962).

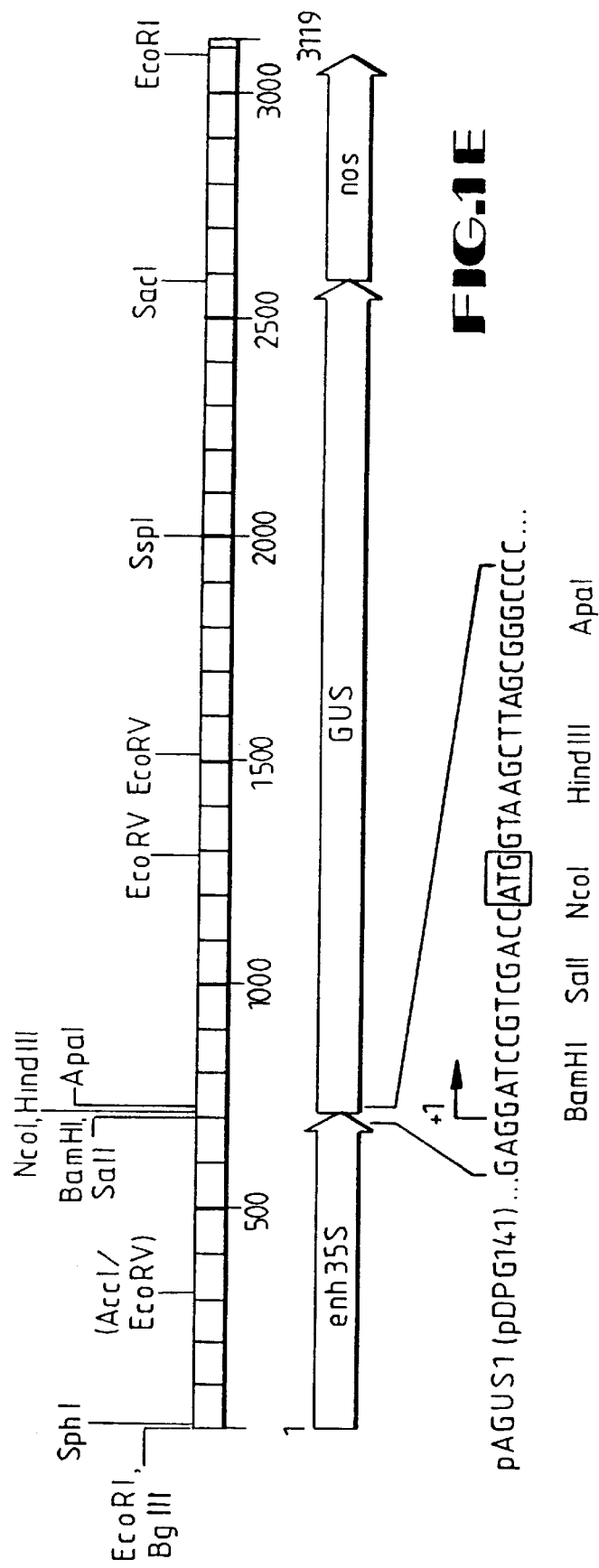

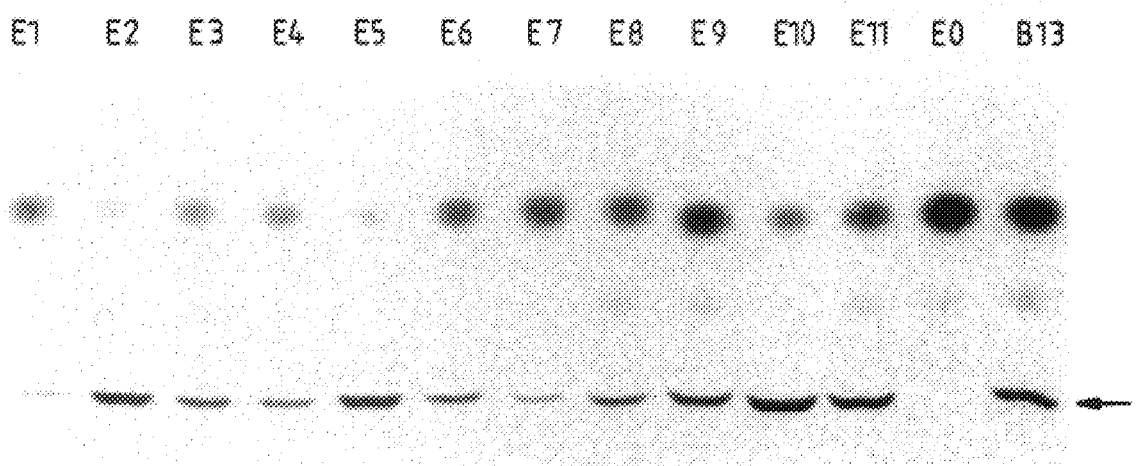

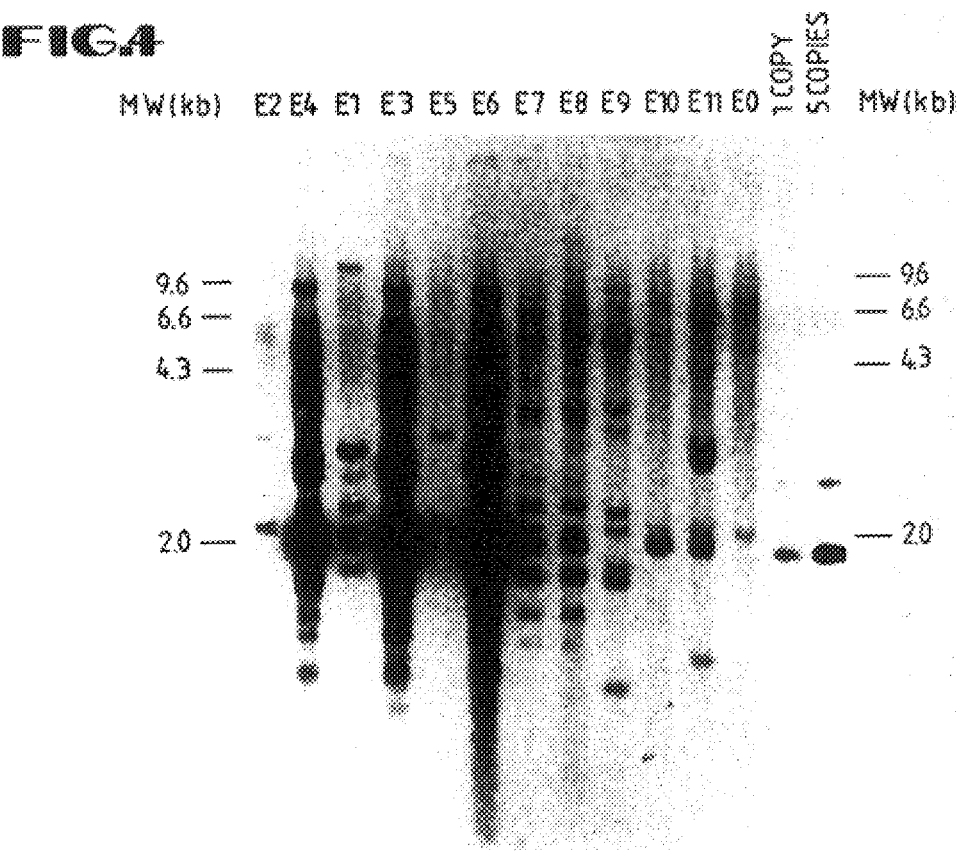

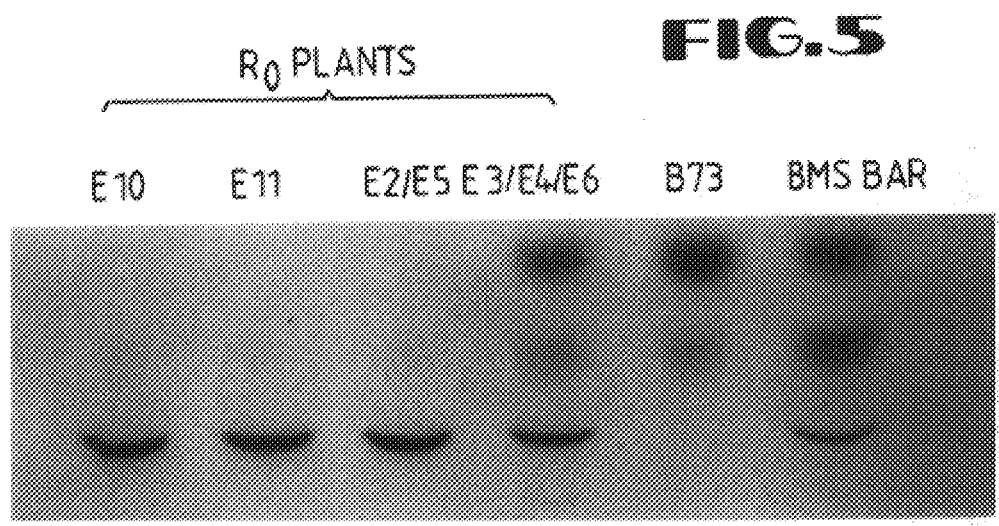

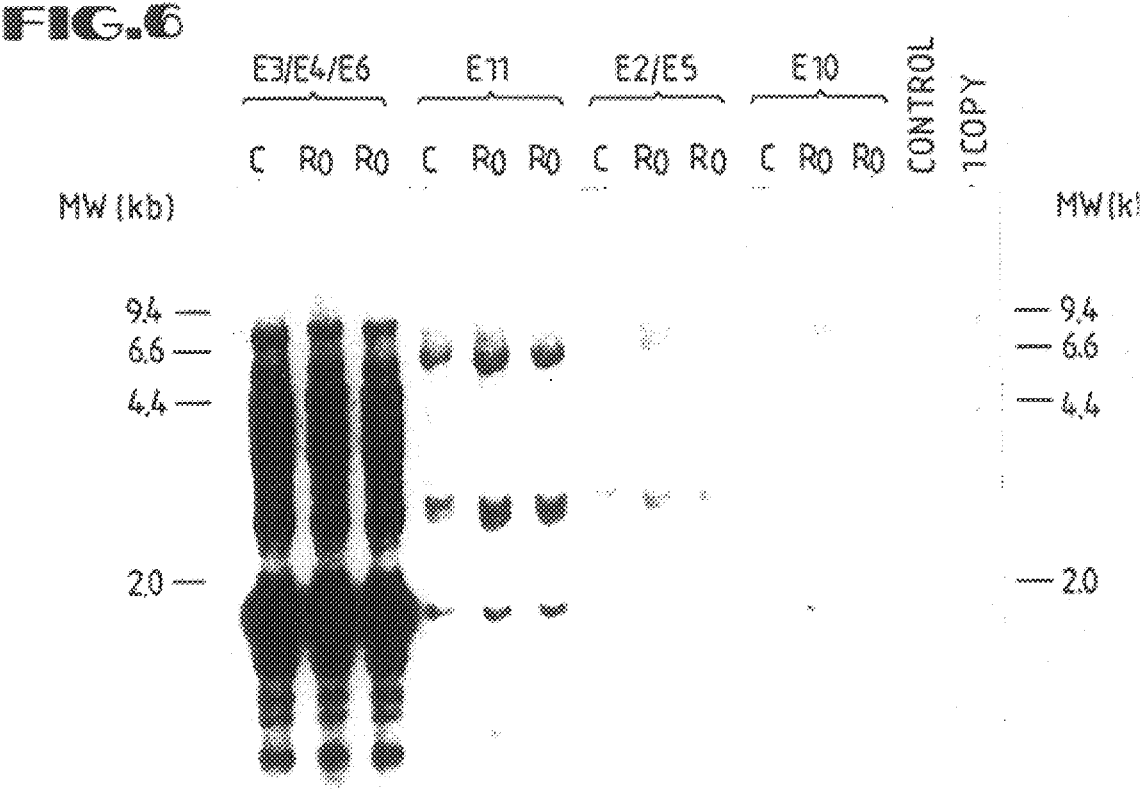

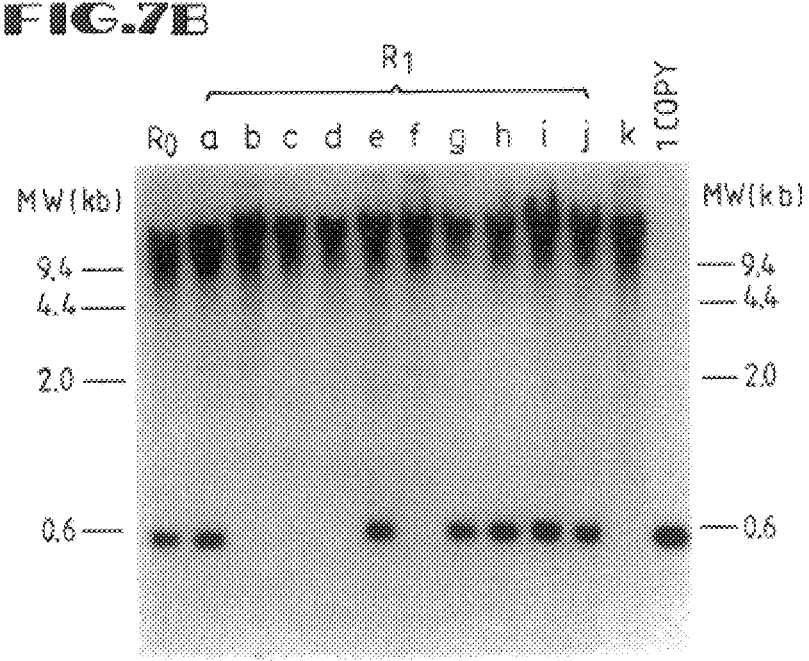

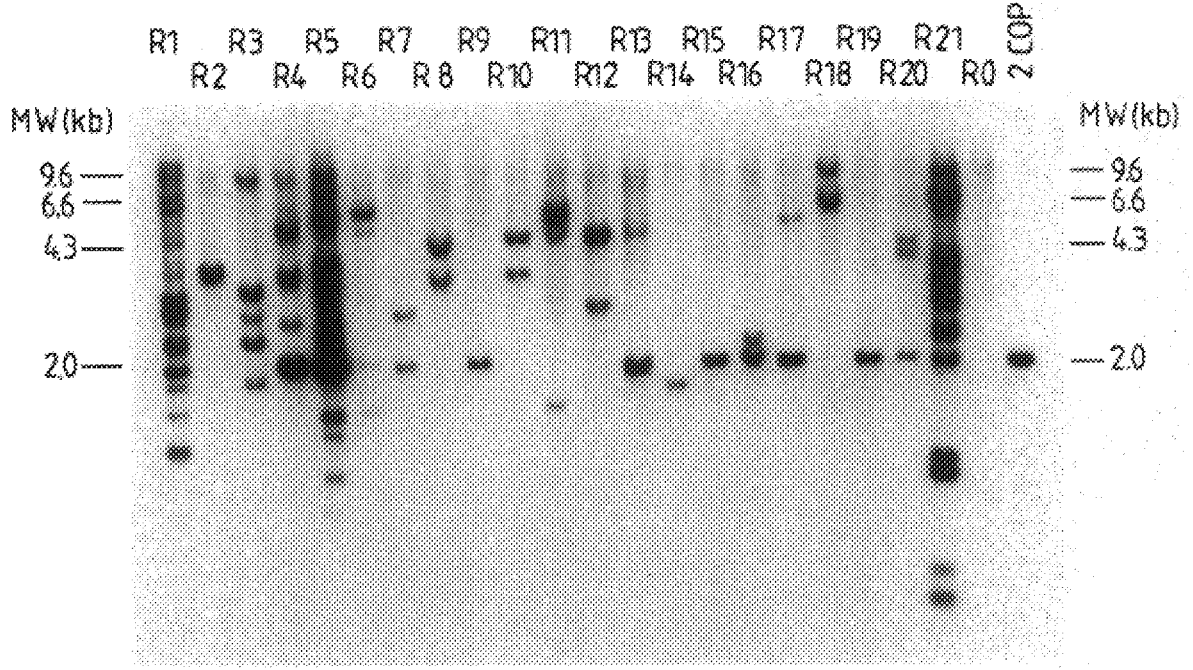

METHODS AND COMPOSITIONS FOR THE PRODUCTION OF STABLY TRANSFORMED FERTILE MONOCOT PLANTS AND CELLS THEREOF

This application is a Continuation of U.S. Ser. No. 07/565,844, filed on Aug. 9, 1990, now issued as U.S. Pat. No. 5,550,318, which is a Continuation-in-part of U.S. Ser. No. 07/513,298, filed on Apr. 17, 1990, now abandoned.

BACKGROUND OF THE INVENTION

1. Field of the Invention

The present invention relates to reproducible systems for genetically transforming monocotyledonous plants such as maize, to methods of selecting stable genetic transformants from suspensions of transformed cells, and to methods of producing fertile plants from the transformed cells. Exemplary transformation methods include the use of microprojectile bombardment to introduce nucleic acids into cells, and selectable and/or screenable marker systems, for example, genes which confer resistance (e.g., antibiotic, herbicide, etc.), or which contain an otherwise phenotypically observable trait. In other aspects, the invention relates to the production of stably transformed and fertile monocot plants, gametes and offspring from the transgenic plants.

2. Description of the Related Art

Ever since the human species emerged from the hunting-gathering phase of its existence, and entered an agricultural phase, a major goal of human ingenuity and invention has been to improve crop yield and to alter and improve the characteristics of plants. In particular, man has sought to alter the characteristics of plants to make them more tasty and/or nutritious, to produce increased crop yield or render plants more adaptable to specific environments.

Up until recent times, crop and plant improvements depended on selective breeding of plants with desirable characteristics. Initial breeding success was probably accidental, resulting from observation of a plant with desirable characteristics, and use of that plant to propagate the next generation. However, because such plants had within them heterogenous genetic complements, it was unlikely that progeny identical to the parent(s) with the desirable traits would emerge. Nonetheless, advances in controlled breeding have resulted from both increasing knowledge of the mechanisms operative in hereditary transmission, and by empirical observations of results of making various parental plant crosses.

Recent advances in molecular biology have dramatically expanded man's ability to manipulate the germplasm of animals and plants. Genes controlling specific phenotypes, for example specific polypeptides that lend antibiotic or herbicide resistance, have been located within certain germplasm and isolated from it. Even more important has been the ability to take the genes which have been isolated from one organism and to introduce them into another organism. This transformation may be accomplished even where the recipient organism is from a different phylum, genus or species from that which donated the gene (heterologous transformation).

Attempts have been made to genetically engineer desired traits into plant genomes by introduction of exogenous genes using genetic engineering techniques. These techniques have been successfully applied in some plant systems, principally in dicotyledonous species. The uptake of new DNA by recipient plant cells has been accomplished by various means, including Agrobacterium infection (32), polyethylene glycol (PEG)-mediated DNA uptake (25), electroporation of protoplasts (17) and microprojectile bombardment (23). Unfortunately, the introduction of exogenous DNA into monocotyledonous species and subsequent regeneration of transformed plants has proven much more difficult than transformation and regeneration in dicotyledonous plants. Moreover, reports of methods for the transformation of monocotyledons such as maize, and subsequent production of fertile maize plants, have not been forthcoming. Consequently, success has not been achieved in this area and commercial implementation of transformation by production of fertile transgenic plants has not been achieved. This failure has been particularly unfortunate in the case of maize, where there is a particularly great need for methods for improving genetic characteristics.

Problems in the development of genetically transformed monocotyledonous species have arisen in a variety of general areas. For example, there is generally a lack of methods which allow one to introduce nucleic acids into cells and yet permit efficient cell culture and eventual regeneration of fertile plants. Only limited successes have been noted. In rice, for example, DNA transfer has only recently been reported using protoplast electroporation and subsequent regeneration of transgenic plants (41). Furthermore, in maize, transformation using protoplast electroporation has also been reported (see, e.g., 17).

However, recovery of stably transformed plants has not been reproducible. A particularly serious failure is that the few transgenic plants produced in the case of maize have not been fertile (38). While regeneration of fertile corn plants from protoplasts has been reported (37, 39), these reported methods have been limited to the use of non-transformed protoplasts. Moreover, regeneration of plants from protoplasts is a technique which carries its own set of significant drawbacks. Even with vigorous attempts to achieve fertile, transformed maize plants, reports of success in this regard have not been forthcoming.

A transformation technique that circumvents the need to use protoplasts is microprojectile bombardment. Although transient expression of a reporter gene was detected in bombarded tobacco pollen (47), stable transformation by microprojectile bombardment of pollen has not been reported for any plant species. Bombardment of soybean apical meristems with DNA-coated gold particles resulted in chimeric plants containing transgenic sectors. Progeny containing the introduced gene were obtained at a low frequency (27). Bombardment of shoot meristems of immature maize embryos resulted in sectors of tissue expressing a visible marker, anthocyanin, the synthesis of which was triggered by the introduction of a regulatory gene (46). An analysis of cell lineage patterns in maize (28) suggests that germline transformation of maize by such an approach may be difficult.

A second major problem in achieving successful monocot transformation has resulted from the lack of efficient marker gene systems which have been employed to identify stably transformed cells. Marker gene systems are those which allow the selection of, and/or screening for, expression products of DNA. For use as assays for transformed cells, the selectable or screenable products should be those from genetic constructs introduced into the recipient cells. Hence, such marker genes can be used to identify stable transformants.

Of the more commonly used marker gene systems are gene systems which confer resistance to aminoglycosides such as kanamycin. While kanamycin resistance has been used successfully in both rice (51) and corn protoplast systems (38), it remains a very difficult selective agent to use in monocots due to high endogenous resistance (19). Many monocot species, maize, in particular, possess high endogenous levels of resistance to aminoglycosides. Consequently, this class of compounds cannot be used reproducibly to distinguish transformed from non-transformed tissue. New methods for reproducible selection of or screening for transformed plant cells are therefore needed.

Accordingly, it is clear that improved methods and/or approaches to the genetic transformation of monocotyledonous species would represent a great advance in the art. Furthermore, it would be of particular significance to provide novel approaches to monocot transformation, such as transformation of maize cells, which would allow for the production of stably transformed, fertile corn plants and progeny into which desired exogenous genes have been introduced. Furthermore, the identification of marker gene systems applicable to monocot systems such as maize would provide a useful means for applying such techniques generally. Thus, the development of these and other techniques for the preparation of stable genetically transformed monocots such as maize could potentially revolutionize approaches to monocot breeding.

SUMMARY OF THE INVENTION

The present invention addresses one or more of the foregoing or other shortcomings in the prior art by providing methods and compositions for the preparation of stably transformed, monocotyledonous cells and subsequent regeneration of fertile, transgenic plants and progeny, particularly maize.

It is therefore a particular object of the present invention to provide techniques that will allow one to prepare transgenic, fertile monocots such as maize which are preferably diploid and which have been stably transformed through the introduction of a desired gene into its genome.

The present invention thus relates generally to methods for the production of transgenic plants. As used herein, the term transgenic plants is intended to refer to plants that have incorporated exogenous genes or DNA sequences, including but not limited to genes or DNA sequences which are perhaps not normally present, genes not normally transcribed and translated ("expressed") in a given cell type, or any other genes of DNA sequences which one desires to introduce into the non-transformed plant, such as genes which may normally be present in the non-transformed plant but which one desires to have altered expression.

Exemplary genes which may be introduced include, for example, DNA sequences or genes from another species, or even genes or sequences which originate with or are present in the same species, but are incorporated into recipient cells by genetic engineering methods rather than classical reproduction or breeding techniques. However, the term exogenous, is also intended to refer to genes which are not normally present in the cell being transformed, or perhaps simply not present in the form, structure, etc., as found in the transforming DNA segment or gene, or genes which are normally present yet which one desires, e.g., to have over-expressed. Thus, the term "exogenous" gene or DNA is intended to refer to any gene or DNA segment that is introduced into a recipient cell, regardless of whether a similar gene may already be present in such a cell.

An initial step in the production of fertile transgenic plants is the obtaining of a DNA composition, e.g., vectors, plasmids, linear DNA fragments, and the like, a component of which is to be delivered to recipient monocotyledonous cells. DNA segments for use in transforming such cells will, of course, generally comprise the gene or genes which one desires to introduce into the cells. These genes can further include structures such as promoters, enhancers, polylinkers, or even regulatory genes as desired.

The construction of vectors which may be employed in practicing the present invention is generally within the skill of the art. (See generally, refs 79, 80). Preferred constructs will generally include a plant promoter such as the CaMV 35S promoter (68), or others such as CaMV 19S (69), nos (70), Adh (71), sucrose synthase (72), those associated with the R gene complex (96), or even tissue specific promoters such as root cell promoters (73) and tissue specific enhancers (74). Constructs will also include the gene of interest along with a 3' end such as that from Tr7 or nos (75), or the like. Regulatory elements such as Adh intron 1 (76), sucrose synthase intron (77) or TMV omega element (78), may further be included where desired.

Certain elements may find utility when incorporated into genomes, even without an associated expressible gene. For example, transposons such as Ac, Ds or Mu are elements which can insert themselves into genes and cause unstable mutations. This instability apparently results from subsequent excision of the element from the mutant locus during plant or seed development. For a review covering the use of transposon elements, see references 56 and 57. These elements, particularly Ac, may be introduced in order to inactivate (or activate) and thereby "tag" a particular trait. Once tagged, the gene with this trait may be cloned, e.g., using the transposon sequence as a PCR primer together with PCR gene cloning techniques (58,59). Once identified, the entire gene(s) for the particular trait, including control or regulatory regions where desired, may be isolated, cloned and manipulated as desired prior to re-introduction.

Another possible element which may be introduced is a matrix attachment region element (MAR), such as the chicken lysozyme A element (61), which can be positioned around an expressible gene of interest to effect an increase in overall expression of the gene and diminish position dependent effects upon incorporation into the plant genome (61, 62).

The generation and use of recipient cells is believed to be an important aspect of the invention. As used herein, the term "recipient cell" is intended to refer to monocot cells that are receptive to transformation and subsequent regeneration into stably transformed, fertile monocot plants. The inventors thus propose that not all cells present in a population of cells subjected to transforming events will be "recipient" to successful transformation and regeneration. However, it is proposed that through the application of the techniques disclosed herein, one will be enabled to obtain populations which contain sufficient numbers of recipient cells to allow for successful stable transformation and regeneration.

Certain techniques are disclosed which may enrich for recipient cells. For example, it is believed that Type II callus development, followed by manual selection and culture of friable, embryogenic tissue, results in an enrichment of recipient cells. Suspension culturing, particularly using the media disclosed in Table I herein, may also improve the ratio of recipient to non-recipient cells in any given population. In fact, it is proposed that media such as MS which has a high ammonia/nitrate ratio is counterproductive to the generation of recipient cells in that it promotes loss of morphogenic capacity. N6 media on the other hand has a somewhat lower ammonia/nitrate ratio, and contains micronutrients such a molybdenum and manganese, and may promote the generation of recipient cells by maintaining cells in a proembryonic state capable of sustained divisions.

Manual selection of recipient cells, e.g., by selecting embryogenic cells from the surface of a Type II callus, is one means employed by the inventors in an attempt to enrich for recipient cells prior to culturing (whether cultured on solid media or in suspension). The preferred cells may be those located at the surface of a cell cluster, and may further be identifiable by their lack of differentiation, their size and dense cytoplasm. It is proposed that the preferred cells will generally be those cells which are less differentiated, or not yet committed to differentiation. Thus, one may wish to identify and select those cells which are cytoplasmically dense, evacuolated with a high nucleus to cytoplasm ratio (e.g., determined by cytological observations), small size (e.g., 10–20 µm), and capable of sustained divisions and proembryo formation.

It is proposed that other possible means of identifying such cells might be through the use of dyes such as Evan's blue which is excluded by cells with relatively non-permeable membranes (embryogenic cells tend to have relatively non-permeable membranes). In contrast, Evan's blue tends to be taken up by relatively differentiated cells such as rooty cells and snake cells (so-called due to their snake-like appearance).

Other possible means of identifying recipient cells include the use of isozyme markers of embryogenic cells, such as glutamate dehydrogenase, which can be detected by cytochemical stains (81). However, it is believed that the use of isozyme markers such as glutamate dehydrogenase may lead to some degree of false positives from non-embryogenic cells such as rooty cells which nonetheless have a relatively high metabolic activity.

Additionally, the inventors propose that cryopreservation may effect the development of, or perhaps select for, recipient cells. If such a selection occurs upon cryopreservation, it may be due to a selection against highly vacuolated, non-embryogenic cells, which are perhaps somewhat selectively killed during cryopreservation.

The frequency of occurrence of cells receiving DNA is believed to be low. Moreover, it is most likely that not all recipient cells receiving DNA segments will result in a transformed cell wherein the DNA is stably integrated into the plant genome and/or expressed. Some may show only initial and transient gene expression. However, it is proposed that certain cells from virtually any monocot species may be stably transformed through the application of the techniques disclosed herein.

The most preferred monocot will be the cereals such as maize. With respect to maize, the inventors propose that many of the techniques of the invention will be applicable to maize varieties in general, whether inbred, elite inbred or hybrid varieties. It should be pointed out, though, that not all cell lines developed out of a particular variety or cross will necessarily show the same degree of stable transformability. For example, the present invention is exemplified through the use of A188×B73 cell lines developed by standard techniques out of an A188×B73 cross. The lines identified as SC716 and SC82 are examples of cells lines which were developed from an A188×B73 cross as described hereinbelow. However, a number of other cell lines developed from the same cross have not as yet proven to be stably transformable. Thus, stable transformability may not be immediately apparent with some lines even from the same cross. (2 out of about 12 A188×B73 lines have proved to be stably transformable and yield fertile transgenic plants; about 16% of the lines). Thus, where one desires to prepare transformants to a particular cross or variety, it will generally be desirable to develop several cell lines from the particular cross or variety (e.g., 8 to 10), and subject all of the lines so developed to the transformation protocols hereof.

In order to improve the ability to identify transformants, one may desire to employ a selectable or screenable marker gene as, or in addition to, the expressible gene of interest. Marker genes code for phenotypes that allow cells which express the marker gene to be distinguished from cells that do not have the marker. Such genes may encode either a selectable or screenable marker, depending on whether the marker confers a trait which one can select for by chemical means, i.e., through the use of a selective agent (e.g., an herbicide, antibiotic, or the like), or whether it is simply a trait that one can identify through observation or testing (e.g., the R-locus trait). of course, many examples of suitable marker genes are known to the art and can be employed in the practice of the invention.

Possible selectable markers for use in connection with the present invention include but are not limited to a neo gene (82) which codes for kanamycin resistance and can be selected for using kanamycin, G418, etc.; a bar gene which codes for bialaphos resistance; a mutant EPSP synthase gene (67) which encodes glyphosate resistance; a nitrilase gene which confers resistance to bromoxynil (83); a mutant acetolactate synthase gene (ALS) which confers imidazolinone or sulphonylurea resistance (60); or a methotrexate resistant DHFR gene (95). Where a mutant EPSP synthase gene is employed, additional benefit may be realized through the incorporation of a suitable chloroplast transit peptide (CTP; see ref. 94).

Exemplary screenable markers include a β-glucuronidase or uidA gene (GUS) which encodes an enzyme for which various chromogenic substrates are known; an R-locus gene, which encodes a product that regulates the production of anthocyanin pigments (red color) in plant tissues (59); a β-lactamase gene (98), a gene which encodes an enzyme for which various chromogenic substrates are known (e.g., PADAC, a chromogenic cephalosporin); a luciferase gene (84); a xylE gene (54) which encodes a catechol dioxygenase that can convert chromogenic catechols; an α-amylase gene (85); a tyrosinase gene (55) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins detectable, e.g., by ELISA, small active enzymes detectable in extracellular solution (e.g., α-amylase, β-lactamase, phosphinothricin transferase), or proteins which are inserted or trapped in the cell wall (such as proteins which include a leader sequence such as that found in the expression unit of extensin or tobacco PR-S).

Of course, in light of this disclosure, numerous other possible selectable and/or screenable marker genes will be apparent to those of skill in the art. Therefore, the foregoing discussion is intended to be exemplary rather than exhaustive. Although the present disclosure is exemplified in detail through the use of the bar and/or GUS genes, the applicable techniques for making and using any other screenable or selectable marker gene will be within the skill in the art in light of the present disclosure.

An illustrative embodiment of marker genes capable of being used in systems to select transformants is the bar gene from Streptomyces, such as from the hygroscopicus species. The bar gene codes for phosphinothricin acetyl transferase (PAT) that inactivates the active ingredient in the herbicide bialaphos, phosphinothricin (PPT). PPT inhibits glutamine synthetase, (29, 47) causing rapid accumulation of ammonia and cell death. Success in use of this selective system in the case of monocots was unexpected because of the major difficulties which have been encountered in transformation of cereals (36).

Where one desires to employ a bialaphos resistance gene in the practice of the invention, the inventors have discovered that a particularly useful gene for this purpose is the bar gene obtainable from species of Streptomyces (ATCC No. 21,705). The cloning of the bar gene has been described (29, 45) as has the use of the bar gene in the context of plants other than monocots (10, 11). However, in light of the techniques disclosed herein and the general recombinant techniques which are known in the art, the introduction and use of any of the foregoing or other genes is now possible.

The use of a gene from the maize R gene complex is proposed as a particularly useful screenable marker. The R gene complex in maize encodes a protein that acts to regulate the production of anthocyanin pigments in most seed and plant tissue. Maize strains can have one or as many as four R alleles which combine to regulate pigmentation in a developmental and tissue specific manner. The present inventors have applied a gene from the R gene complex to maize transformation because it is viable, it is a naturally occurring product in maize, and it is visually screenable without the need for additional assays. Thus, an R gene introduced into such cells will cause the expression of a red pigment and, if stably incorporated, can be visually scored as a red sector. If a maize line is dominant for the enzymatic intermediates in the anthocyanin biosynthetic pathway (C2, A1, A2, Bz1 and Bz2), but recessive at the R locus, any cell from that line can be employed as a recipient for transformation. Exemplary lines include rg-Stadler in Wisconsin 22 and TR112, a K55 derivative which is r-g, b, P1.

The inventors further propose that R gene regulatory regions may be employed in chimeric constructs in order to provide mechanisms for controlling the expression of chimeric genes. More diversity of phenotypic expression is known at the R locus than at any other locus (63). It is contemplated that regulatory regions obtained from regions 5' to the structural R gene could be very valuable in directing the expression of genes for, e.g., insect resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bol3). Sn is a dominant member of the R gene complex and is functionally similar to the R and B loci in that Sn controls the tissue specific deposition of anthocyanin pigments in certain seedling and plant cells. Therefore, its phenotype is similar to R.

The choice of the particular DNA segments to be delivered to the recipient cells will often depend on the purpose of the transformation. One of the major purposes of transformation of crop plants is to add some commercially desirable, agronomically important traits to the plant. Such traits include, but are not limited to, herbicide resistance, increased yields, insect and disease resistance, physical appearance, food content and makeup, etc. For example, one may desire to incorporate one or more genes encoding herbicide resistance. The bar and glyphosate tolerant EPSP synthase genes are good examples. A potential insect resistance gene which can be introduced includes the *Bacillus thuringiensis* crystal toxin gene (86), which may provide resistance to pests such as lepidopteran or coleopteran. Protease inhibitors may also provide resistance (64). Moreover, the expression of juvenile hormone esterase directed towards specific insect pests may also have insecticidal activity, or perhaps cause cessation of metamorphosis (65).

Genes encoding proteins characterized as having potential insecticidal activity, such as the cowpea trypsin inhibitor (CpTI; 88) may find use as a rootworm deterrent;

genes encoding avermectin (89,90) may prove particularly useful as a corn rootworm deterrent. Furthermore, genes encoding lectins may, additionally or alternatively, confer insecticide properties (e.g., barley, wheat germ agglutinin, rice lectins, see ref. 91), while others may confer antifungal properties (e.g., UDA (stinging nettle lectin), hevein, chitinase, see refs. 92, 93).

It is proposed that benefits may be realized in terms of increased resistance to cold temperatures through the introduction of an "antifreeze" protein such as that of the Winder Flounder (87).

Ultimately, the most desirable "traits" for introduction into a monocot genome may be homologous genes or gene families which encode a desired trait (e.g., increased yield per acre) and which are introduced under the control of novel promoters or enhancers, etc., or perhaps even homologous or tissue specific (e.g., root specific) promoters or control elements.

The invention thus contemplates that particular benefits may be realized by the transformation of plant cells with any expressible gene, and is not intended to be limited to the use of marker genes. As used herein, an "expressible gene" is any gene that is capable of being translated into a protein, expressed as a trait of interest, or the like, etc., and is not limited to selectable, screenable or non-selectable marker genes. The invention also contemplates that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

In certain embodiments, recipient cells are selected following growth in culture. Where employed, cultured cells will preferably be grown either on solid supports or in the form of liquid suspensions. In either instance, nutrients may be provided to the cells in the form of media, and environmental conditions controlled. There are many types of tissue culture media comprising amino acids, salts, sugars, hormones and vitamins. Most of the media employed in the practice of the invention will have some similar components (see, e.g., Table 1 herein below), the media differ in the composition and proportions of their ingredients depending on the particular application envisioned. For example, various cell types usually grow in more than one type of media, but will exhibit different growth rates and different morphologies, depending on the growth media. In some media, cells survive but do not divide.

Various types of media suitable for culture of plant cells have been previously described. Examples of these media include, but are not limited to the N6 medium described by Chu, et al. (5) and the MS media (30). In an exemplary embodiment for preparation of recipient cells, the inventors have modified these media (see, Table 1). A preferred hormone for such purposes is dicamba or 2,4-D. However, other hormones may be employed, including NAA, NAA +2,4-D or perhaps even picloram. Modifications of these and other basic media may facilitate growth of recipient cells at specific developmental stages.

An exemplary embodiment for culturing recipient corn cells in suspension cultures includes using embryogenic cells in Type II callus, selecting for small (10–30μ) isodiametric, cytoplasmically dense cells, growing the cells in suspension cultures with hormone containing media, subculturing into a progression of media to facilitate development of shoots and roots, and finally, hardening the plant and readying it metabolically for growth in soil. For use in transformation, suspension culture cells may be cryopreserved and stored for periods of time, thawed, then used as recipient cells for transformation. It is proposed that cryopreservation may serve to enrich for or promote the development of recipient cells. The inventors propose that there is a narrow temporal window in which cultured cells retain their regenerative ability, thus, it is believed that they must be preserved at or before that temporal period if they are to be used for future transformation and regeneration.

An illustrative embodiment of cryopreservation methods comprises the steps of slowly adding cryoprotectants to suspension cultures to give a final concentration of 10% dimethyl sulfoxide, 10% polyethylene glycol (6000MW), 0.23M proline, and 0.23M glucose. The mixture is then cooled to –35° C. at 0.5° C. per minute. After an isothermal period of 45 minutes, samples are placed in liquid N2. (Modification of methods of Withers and King (49); and Finkle, et al.(15)). To reinitiate suspension cultures from cryopreserved material, cells may be thawed rapidly and pipetted onto feeder plates similar to those described by Rhodes, et al. (38).

One embodiment of cultured plant cells that can serve as recipient cells for transforming with desired DNA segments, such as those which comprise expressible genes, includes corn cells, more specifically, cells from *Zea mays* L. Somatic cells are of various types. Embryogenic cells are one example of somatic cells which may be induced to regenerate a plant through embryo formation. Non-embryogenic cells are those which will typically not respond in such a fashion. An example of non-embryogenic cells are certain Black Mexican Sweet (BMS) corn cells, and these have been successfully transformed by microprojectile bombardment using the neo gene followed by selection with the aminoglycoside, kanamycin (22). However, this BMS culture was not found to be regenerable, and general use of kanamycin may be hampered by endogenous resistance of maize (19).

Other recipient cell targets include, but are not limited to, meristem cells, Type I and II calli and gametic cells such as microspores and pollen. Pollen, as well as its precursor cells, microspores, may be capable of functioning as recipient cells for genetic transformation, or as vectors to carry foreign DNA for incorporation during fertilization. Direct pollen transformation would obviate the need for cell culture. Meristematic cells (i.e., plant cells capable of continual cell division and characterized by an undifferentiated cytological appearance, normally found at growing points or tissues in plants such as root tips, stem apices, lateral buds, etc.) may represent another type of recipient plant cell. Because of their undifferentiated growth and capacity for organ differentiation and totipotency, a single transformed meristematic cell could be recovered as a whole transformed plant. In fact, it is proposed that embryogenic suspension cultures may be an in vitro meristematic cell system, retaining an ability for continued cell division in an undifferentiated state, controlled by the media environment.

The development of embryogenic maize calli and suspension cultures useful in the context of the present invention, e.g., as recipient cells for transformation, has been described in U.S. Ser. No. 06/877,033, filed Jun. 7 1986, incorporated herein by reference.

There are many methods for introducing transforming DNA segments into cells, but not all are suitable for delivering DNA to plant cells. Suitable methods are believed to include virtually any method by which DNA can be introduced into a cell, such as by Agrobacterium infection or direct delivery of DNA such as, for example, by PEG-mediated transformation, by electroporation or by acceleration of DNA coated particles, etc. Acceleration methods are generally preferred and include, for example, microprojectile bombardment and the like. Electroporation has been used to transform corn protoplasts (17).

An example of a method for delivering transforming DNA segments to plant cells is microprojectile bombardment. In this method, non-biological particles may be coated with nucleic acids and delivered into cells by a propelling force. Exemplary particles include those comprised of tungsten, gold, platinum, and the like.

A particular advantage of microprojectile bombardment, in addition to it being an effective means of reproducibly stably transforming monocots, is that neither the isolation of protoplasts (8) nor the susceptibility of Agrobacterium infection is required. An illustrative embodiment of a method for delivering DNA into maize cells by acceleration is a Biolistics Particle Delivery System, which can be used to propel particles coated with DNA through a screen, such as a stainless steel or Nytex screen, onto a filter surface covered with corn cells cultured in suspension. The screen disperses the tungsten-DNA particles so that they are not delivered to the recipient cells in large aggregates. It is believed that without a screen intervening between the projectile apparatus and the cells to be bombarded, the projectiles aggregate and may be too large for attaining a high frequency of transformation. This may be due to damage inflicted on the recipient cells by projectiles that are too large.

For the bombardment, cells in suspension are preferably concentrated on filters. Filters containing the cells to be bombarded are positioned at an appropriate distance below the macroprojectile stopping plate. If desired, one or more screens are also positioned between the gun and the cells to be bombarded. Through the use of techniques set forth herein one may obtain up to 1000 or more clusters of cells transiently expressing a marker gene ("foci") on the bombarded filter. The number of cells in a focus which express the exogenous gene product 48 hours post-bombardment often range from 1 to 10 and average 2 to 3.

After effecting delivery of exogenous DNA to recipient cells by any of the methods discussed above, a preferred step is to identify the transformed cells for further culturing and plant regeneration. This step may include assaying cultures directly for a screenable trait or by exposing the bombarded cultures to a selective agent or agents.

An example of a screenable marker trait is the red pigment produced under the control of the R-locus in maize. This pigment may be detected by culturing cells on a solid support containing nutrient media capable of supporting growth at this stage, incubating the cells at, e.g., 18° C. and greater than 180 $\mu$E m$^{-2}$ sec$^{-1}$, and selecting cells from colonies (visible aggregates of cells) that are pigmented. These cells may be cultured further, either in suspension or on solid media.

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene Conferring resistance to the selective agent used, will grow and divide in culture. Sensitive cells will not be amenable to further culturing.

To use the bar-bialaphos selective system, bombarded cells on filters are resuspended in nonselective liquid medium, cultured (e.g., for one to two weeks) and transferred to filters overlaying solid medium containing from 1–3 mg/l bialaphos. While ranges of 1–3 mg/l will typically be preferred, it is proposed that ranges of 0.1–50 mg/l will find utility in the practice of the invention. The type of filter for use in bombardment is not believed to be particularly crucial, and can comprise any solid, porous, inert support.

Cells that survive the exposure to the selective agent may be cultured in media that supports regeneration of plants. An example of suitable media is a modification of MS media (Table 1). Tissue is maintained on a basic media with hormones for about 2–4 weeks, then transferred to media with no hormones. After 2–4 weeks, shoot development will signal the time to transfer to another media.

Regeneration typically requires a progression of media whose composition has been modified to provide the appropriate nutrients and hormonal signals during sequential developmental stages from the transformed callus to the more mature plant. Developing plantlets are transferred to soil, and hardened, e.g., in an environmentally controlled chamber at about 85% relative humidity, 600 ppm $CO_2$, and 250 microeinsteins m$^{-2}$·s$^{-1}$ of light. Plants are preferably matured either in a growth chamber or greenhouse. Regeneration will typically take about 3–12 weeks. During regeneration, cells are grown on solid media in tissue culture vessels. An illustrative embodiment of such a vessel is a petri dish. Regenerating plants are preferably grown at about 19° to 28° C. After the regenerating plants have reached the stage of shoot and root development, they may be transferred to a greenhouse for further growth and testing.

To confirm the presence in the regenerating plants of traits delivered to the recipient cells through the application of exogenous DNA, alone or in conjunction with marker genes, assays for expression of said genes may be performed, e.g., by testing parts of the regenerated plants. Exemplary parts which may be assayed are leaves. A typical transformant assay includes contacting regenerating plants or extracts of plants with a substrate that is acted upon by the transforming gene product. At this stage of development, the plants will not be lethally affected by such an assay. Removal of small portions of the plants does not cause their death or interfere with further development.

In one study, $R_o$ plants were regenerated from transformants of an A188xB73 suspension culture line (SC82) transformants, and these plants exhibited a phenotype expected of the genotype of hybrid A188xB73 from which the callus and culture were derived. The plants were similar in height to seed-derived A188 plants (3–5 ft tall) but had B73 traits such as anthocyanin accumulation in stalks and prop roots, and the presence of upright leaves. It would also be expected that some traits in the transformed plants would differ from their source, and indeed some variation will likely occur.

In an exemplary embodiment, the proportion of regenerating plants derived from transformed callus that successfully grew and reached maturity after transfer to the greenhouse was 97% (73 of 76). In one example, at least 50 viable progeny were recovered from $R_o$ plants. $R_o$ plants in the greenhouse were tested for fertility by backcrossing the transformed plants with seed-derived plants by pollinating the $R_o$ ears with pollen from seed derived B73 plants and this resulted in kernel development. Note, however, that kernels on transformed plants may require embryo rescue due to cessation of kernel development and premature senescence of plants.

To rescue developing embryos, they are excised from surface-disinfected kernels 10–20 days post-pollination and cultured. An embodiment of media used for culture at this stage comprises MS salts, 2% sucrose, and 5.5 g/l agarose. In an illustrative embodiment of embryo rescue, large embryos (defined as greater than 3 mm in length) are germinated directly on an appropriate media. Embryos smaller than that were cultured for one week on media containing the above ingredients along with $10^{-5}$M abscisic acid and then transferred to hormone-free medium for germination.

Progeny may be recovered from the transformed plants and tested for expression of the exogenous expressible gene by localized application of an appropriate substrate to plant parts such as leaves. In the case of bar transformed plants, it was found that transformed parental plants ($R_o$) and their progeny ($R_1$) exhibited no bialaphos-related necrosis after localized application of the herbicide Basta to leaves, if there was functional PAT activity in the plants as assessed by an in vitro enzymatic assay. In one study, of 28 progeny ($R_1$) plants tested, 50% (N=14) had PAT activity. All PAT positive progeny tested contained bar, confirming that the presence of the enzyme and the resistance to bialaphos were associated with the transmission through the germline of the marker gene. The nonchimeric nature of the callus and the parental transformants (RO) was suggested by germline transmission and the identical Southern blot hybridization patterns and intensities of the transforming DNA in callus, $R_o$ plants and $R_1$ progeny that segregated for the transformed gene.

Genomic DNA may be isolated from callus cell lines and plants to determine the presence of the exogenous gene through the use of techniques well known to those skilled in the art. Note, that intact sequences will not always be present, presumably due to rearrangement or deletion of sequences in the cell.

The inventors have been successful in producing fertile transgenic monocot plants (maize) where others have failed. Aspects of the methods of the present invention for producing the fertile, transgenic corn plants comprise, but are not limited to, development of suspension cultures of recipient cells using media conducive to specific growth patterns, choice of selective systems that permit efficient detection of transformation; modifications of acceleration methods to introduce genetic vectors with exogenous DNA into cells; invention of methods to regenerate plants from transformed cells at a high frequency; and the production of fertile transgenic plants capable of surviving and reproducing.

DEFINITIONS

Callus—Proliferating mass of cells or tissue in vitro.

Type I—A compact, slow growing, heteromorphic callus (embryogenic/organogenic) which retains meristematic activity in regions of organized tissue.

Type II—A friable, fast growing embryogenic callus composed of aggregates of small isodiametric cells with dense cytoplasm. Often contains small embryoids attached to the underlying callus by a suspensor.

Embryogenic Callus—A type of callus capable of differentiating into somatic embryos.

Germinal Cells (Gametes)—Cells of an organism which are capable of transferring their genetic information to the next generation.

Genotype—The genetic complement of an organism.

Heterologous DNA—DNA from a source different than that of the recipient cell.

Homologous DNA—DNA from the same source as that of the recipient cell.

Hybrid—Progeny resulting from a cross between parental lines.

Inbred Lines—Organisms that are genetically homogeneous (homozygous) resulting from many generations of self crossing.

In Vitro—In the laboratory.

In Vivo—In the living organism.

Monocot—Plants having a single cotyledon (the first leaf of the embryo of seed plants); examples include cereals such as maize, rice, wheat, oats and barley.

Non-Embryogenic Callus—A type of callus composed of undifferentiated, often highly vacuolated cells which are unable to be induced to form embryos.

Phenotype—Traits exhibited by an organism resulting from the interaction of genotype and environment.

Protoplast—Plant cells exclusive of the cell walls.

Somatic Cells—Body cells of an organism, exclusive of germinal cells.

Transformation—Acquisition of new genetic coding sequences by the incorporation of added (exogenous) DNA.

Transgenic—Organisms (plants or animals) into which new DNA sequences are integrated.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 3. Phosphinothricin acetyl transferase (PAT) activity in embryogenic SC82 callus transformants designated E1–E11 and a nonselected control (EO). 25 µg of protein extract were loaded per lane. B13 is a BMS-bar transformant. BMS is Black Mexican Sweet corn. Activities of the different transformants varied approximately 10 fold based on the intensities of the bands.

FIG. 4. Integration of the bar gene in bialaphos-resistant SC82 callus isolates E1–E11. DNA gel blot of genomic DNA (4 µg/digest) from E1–E11 and a nonselected control (EO) digested with EcoRI and HindIII. The molecular weights in kb are shown on the left and right. The blot was hybridized with $^{32}$P-labeled bar from pDPG165 (~25×10$^6$ Cerenkov cpm). Lanes designated 1 and 5 copies refer to the diploid genome and contain 1.9 and 9.5 pg respectively of the 1.9 kb bar expression unit released from pDPG165 with EcoRI and HindIII.

FIG. 5. PAT Activity in Protein Extracts of $R_o$ Plants. Extracts from one plant derived from each of the four transformed regenerable callus lines from a suspension culture of A188×B73, SC82 (E10, E11, E2/E5, and E3/E4/E6) were tested for PAT activity (The designations E2/E5 and E3/E4/E6 represent transformed cell lines with identical DNA gel blot hybridization patterns; the isolates were most likely separated during the culturing and selection process.) Protein extracts from a nontransformed B73 plant and a Black Mexican Sweet (BMS) cell culture bar transformant were included as controls. Approximately 50 micrograms of total protein was used per reaction.

FIG. 6. DNA Gel Blot Analysis of Genomic DNA from Transformed Callus and Corresponding $R_o$ Plants Probed with bar. Genomic DNA was digested with EcoRI and HindIII, which released the 1.9 kb bar expression unit (CaMV 35S promoter-bar-Tr7 3'-end) from pDPG165, the plasmid used for microprojectile bombardment transformation of SC82 cells, and hybridized to bar. The molecular weights in kb are shown on the left and right. Lanes designated E3/E4/E6, E11, E2/E5, and E10 contained 5 µg of either callus (C) or $R_o$ plant DNA. The control lane contained DNA from a nontransformed A188×B73 plant. The lane designated "1 copy" contained 2.3 pg of the 1.9 kb EcoRI/HindIII fragment from pDPG165 representing one copy per diploid genome.

DESCRIPTION OF THE PREFERRED EMBODIMENTS

Figure 1A:
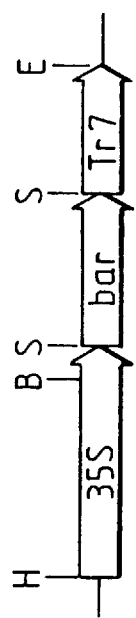
FIG. 1. Schematic representation of plasmids (vectors) used in bombardment experiments. The plasmids have been named (A) pDPG165 which contains bar, and (B) pDPG208 which contains uidA (the gene which encodes β-glucuronidase (GUS)). Letters designate the locations of various restriction sites, locations which may be cleaved by restriction endonucleases, E, EcoRI; H, HindIII; B, BamHI; S, SmaI. A more detailed map of pDPG165 is shown in (C), of pDPG208 in (D). In (E) is shown a restriction map of pAGUS1, also known as pDPG141, in which a the 5'-noncoding and 5'-coding sequences were modified to incorporate the Kozak consensus sequence and a HindIII restriction site. The sequence shown is SEQ ID NO:1. In (F) is shown a restriction map of pDPG237, a plasmid which contains Sn:bol3 cDNA, and in (G) is shown a map of pDPG232, a plasmid which incorporates Rsn cDNA along with a 35S promoter and a Tr7 3' end.

For the first time, fertile transgenic maize plants have been produced, opening the door to new vistas of crop improvement based on in vitro genetic transformation. The inventors have succeeded where others have failed by combining and modifying numerous steps in the overall process leading from somatic cell to transgenic plant. Although the methods disclosed herein are part of a unified process, for illustrative purposes they may be subdivided into: culturing cells to be recipients for exogenous DNA; cryopreserving recipient cells; constructing vectors to deliver the DNA to cells; delivering DNA to cells; assaying for successful transformations; using selective agents if necessary to isolate stable transformants; regenerating plants from transformants; assaying those plants for gene expression and for identification of the exogenous DNA sequences; determining whether the transgenic plants are fertile; and producing offspring of the transgenic plants. The invention also relates to transformed maize cells, transgenic plants and pollen produced by said plants.

A. Tissue Culture

Tissue culture requires media and controlled environments. "Media" refers to the numerous nutrient mixtures that are used to grow cells in vitro, that is, outside of the intact living organism. The medium is usually a suspension of various categories of ingredients (salts, amino acids, hormones, sugars, buffers) that are required for growth of most cell types. However, each specific cell type requires a specific range of ingredient proportions for growth, and an even more specific range of formulas for optimum growth. Rate of cell growth will also vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar and Gelgro are specific types of solid support that are suitable for growth of plant cells in tissue culture.

Some cell types will grow and divide either in liquid suspension or on solid media. As disclosed herein, maize cells will grow in suspension, but regeneration of plants requires transfer from liquid to solid media at some point in development. The type and extent of differentiation of cells in culture will be affected not only by the type of media used and by the environment, for example, pH, but also by whether media is solid or liquid. Table 1 illustrates the composition of various media useful for creation of recipient cells and for plant regeneration.

B. Culturing Cells in Suspension to be Recipients for Transformation

It is believed by the inventors that the ability to prepare and cryopreserve suspension cultures of maize cells is an important aspect of the present invention, in that it provides a means for reproducibly and successfully preparing cells for transformation. The studies described below set forth techniques which have been successfully applied by the inventors to generate transformable and regenerable suspension cultures of maize cells. A variety of different types of media have been developed by the inventors and employed in carrying out various aspects of the invention, including in particular, the development of suspension cultures. The following table, Table 1, sets forth the composition of the media preferred by the inventors for carrying out these aspects of the invention.

TABLE 1

Illustrative Embodiments of Tissue Culture Media Which are Used for Type II Callus Development, Development of Suspension Cultures and Regeneration of Plant Cells (Specifically Maize Cells)

| Medium Id. Number | MS* | N6 | Sucrose | Optimal pH | Other Components** |
|---|---|---|---|---|---|
| 52 | + | – | 2% | 6.0 | 0.25 mg thiamine<br>1 mg 2,4-D<br>10$^{-7}$M ABA<br>Bactoagar |
| 101 | +<br>v | – | 3% | 6.0 | 100 mg myo-inositol<br>Bactoagar |
| 142 | +<br>v | – | 6% | 6.0 | 5 mg BAP<br>0.186 mg NAA<br>0.175 mg IAA<br>0.403 mg 2-IP<br>200 mg myo-inositol<br>Bactoagar |

TABLE 1-continued

Illustrative Embodiments of Tissue Culture
Media Which are Used for Type II Callus
Development, Development of Suspension
Cultures and Regeneration of Plant Cells
(Specifically Maize Cells)

| Medium Id. Number | MS* | N6 | Sucrose | Optimal pH | Other Components** |
|---|---|---|---|---|---|
| 163 | +v | – | 3% | 6.0 | 3.3 mg dicamba<br>100 mg myo-inositol<br>Bactoagar |
| 171 | +v | – | 3% | 6.0 | 0.25 mg 2,4-D<br>10 mg BAP<br>100 mg myo-inositol<br>Bactoagar |
| 173 | +v | – | 6% | 6.0 | 5 mg BAP<br>0.186 mg NAA<br>0.175 mg IAA<br>0.403 mg 2-IP<br>$10^{-5}$M ABA<br>200 mg myo-inositol<br>Bactoagar |
| 177 | +v | – | 3% | 6.0 | 0.25 mg 2,4-D<br>10 mg BAP<br>$10^{-5}$M ABA<br>100 mg myo-inositol<br>Bactoagar |
| 201 | – | +v | 2% | 5.8 | 25 mM proline<br>1 mg 2,4-D<br>100 mg casein hydrolysate<br>Gelgro$^R$ |
| 205 | – | +v | 2% | 5.8 | 25 mM proline<br>0.5 mg 2,4-D<br>100 mg casein hydrolysate<br>Gelgro$^R$ |
| 227 | – | +v | 2% | 5.8 | 25 mM proline<br>13.2 mg dicamba<br>100 mg casein hydrolysate<br>Gelgro$^R$ |
| 401 | + | – | 3% | 6.0 | 0.25 mg thiamine<br>1 mg 2,4-D<br>2 mg NAA<br>200 mg casein hydrolysate<br>500 mg K sulfate<br>100 mg myo-inositol<br>400 mg K phosphate (monobasic) |
| 402 | + | – | 3% | 6.0 | 0.25 mg thiamine<br>25 mM proline<br>1 mg 2,4-D<br>200 mg casein hydrolysate<br>500 mg K sulfate<br>400 mg K phosphate (monobasic)<br>100 mg myo-inositol |
| 409 | + | – | 3% | 6.0 | 0.25 mg thiamine<br>25 mM proline<br>10 mg dicamba<br>200 mg casein hydrolysate<br>500 mg K sulfate<br>400 mg K phosphate (monobasic)<br>100 mg myo-inositol |
| 501 | – | – | 2% | 5.7 | Clark's ***<br>Gelgro$^R$ |

*Basic MS medium described in reference 30. The medium described in ref. 30 is typically modified by decreasing the NH$_4$NO$_3$ from 1.64 g/l to 1.55 g/l, and omitting the pyridoxine HCl, nicotinic acid, myo-inositol and glycine.
+ = present; – = absent; v = vitamins
**NAA = Napthol Acetic Acid
IAA = Indole Acetic Acid
2-IP = 2, isopentyl adenine
2,4-D = 2, 4-Dichlorophenoxyacetic Acid
BAP = 6-benzyl aminopurine
ABA = abscisic acid
*** Basic medium described in reference 6

EXAMPLE 1

Initiation of the Suspension Culture GII (A188XB73)716 (designated SC716) for Use in Transformation This Example describes the development of a maize suspension culture, designated SC716, which was employed in various of the transformation studies described hereinbelow. The Type II tissue used to initiate the cell suspension was derived from immature embryos of A188×B73 plated onto N6-based medium with 1 mg/ml 2,4-D (201; see Table 1). A Type II callus was initiated by visual selection of fast growing, friable embryogenic cells. The suspension was initiated within 6 months after callus initiation. Tissue chosen from the callus to initiate the suspension consisted of very undifferentiated Type II callus, the characteristics of this undifferentiated tissue are the earliest stages of embryo development along with the soft, friable, undifferentiated tissue underlying it.

Approximately one gram of tissue was added to 20 mls of liquid medium. In this example, the liquid medium was medium 402 to which different slow-release hormone capsule treatments were added (see Example 12 below). These capsule treatments included 2,4-D, NAA, 2,4-D plus NAA, and 2 NAA capsules. One flask was initiated for each of the different 402 media plus hormone combinations. Every 7 days each culture was subcultured into fresh medium by transferring a small portion of the cellular suspension to a new flask.

This involved swirling the original flask to suspend the cells (which tend to settle to the bottom of the culture vessel), tilting the flask on its side and allowing the denser cells and cell aggregates to settle slightly. One ml of packed cells was then drawn off from this pool of settled cells together with 4 mls of conditioned medium. A sterile ten ml, wide tip, pipet was used for this transfer (Falcon 7304). Any very large aggregates of cells which would not pass easily through the pipet tip were excluded. If a hormone capsule was present, it was also transferred to the new flask.

After approximately 7 weeks, the loose embryogenic cell aggregates began to predominate and fragment in each of the cultures, reaching a state referred to as "dispersed." The treatment which yielded the highest proportion of embryogenic clusters was the 402 medium plus a NAA capsule. After the cultures became dispersed and were growing at a fast rate, doubling approximately every two to three days as determined by increase in packed cell volume, a one ml packed cell inoculum from each culture was transferred into 401 medium using a ten ml narrow tip pipet (Falcon 7551). These transfers were performed about every 3½ days. An inoculum from the 402 plus 2,4-D plus NAA capsules culture was also used to initiate a culture in 409 medium (402 minus 2,4-D and plus 10mg/l dicamba) either with or without 1 ml coconut water (Gibco 670–8130AG).

The most dispersed cultures were cryopreserved after 2 weeks, 2 months or 5 months.

The culture grown on 409 with coconut water was brought out of cryopreservation eight months later and thawed, cultured for two weeks on solid 201 culture medium using BMS as a feeder layer (38) and transferred to media 409 without coconut water. The culture was maintained by subculturing twice weekly, using 409 media, by the method described above.

EXAMPLE 2

Initiation of the Suspension Culture (A188×B73)82 (designated SC82) for Use in Transformation This Example describes the development of another cell line employed in various of the transformation studies set forth below, termed SC82. In the development of SC82, inoculum for suspension culture initiation was visually selected from a Type II callus that was derived from immature embryos plated on a N6-based medium containing 13.2 mg/l dicamba (227) (Table 1). The suspension culture was initiated within 3 months of initiation of the Type II callus. Small amounts (50–100 mg) of callus distinguishable by visual inspection because of its highly proembryonic morphology, were isolated from more mature or organized structures and inoculated into a 50 ml flask containing 5 mls of filter-sterilized conditioned medium from the various GII (A188×B73) 716 suspension cultures (402 medium with four types of capsule treatments and 409 medium).

After one week, this 5 ml culture was sieved through a 710 micron mesh and used to inoculate 20 mls of corresponding fresh and filter-sterilized conditioned medium from the established GII (A188×B73) 716 cultures in 150 ml flasks. After one week or more of growth, two mls of packed cells were subcultured to fresh media by the method described above. The suspension culture maintained on 409 by this method was then cryopreserved within 3 months. The original cell line, which was maintained on 409 (not a reinoculated cryopreserved culture) was used in experiments 1 and 2 months later which resulted in stable transformation and selection (see Table 2 below). The cryopreserved culture was used for experiment 6 (see Table 2 below).

C. Slow Release Plant Hormone Capsules

Studies following the fate of radioactively labelled plant hormones (2,4-D and NAA) showed that within two days corn cells absorb most of the auxins present in suspension culture media. This problem of hormone depletion can be overcome by spiking the cultures with a small amount of auxin every other day. However, spiking cultures is very time consuming when done on a large scale and also increases the risk of contamination as the culture vessels must be opened frequently. Slow release plant hormone capsules were developed to overcome these problems. In summary, these capsules comprise a plant hormone, usually in a crystalline state, encapsulated in a silicone matrix surrounded by a silicone limiting membrane. The rate of hormone release is controlled by the size of the diffusible area and the thickness of the membrane. They have the advantages of 1) supplying hormones at an acceptable and predictable rate (e.g., 20–100 $\mu$g/20 ml culture media/day, 2) they are of a convenient size (e.g., 0.5–1.5 cm in length) for use in liquid or solid culture medium, 3) they are very durable and easily sterilized by autoclaving, and 4) they can be stored dry until needed.

The present formulation involves the controlled release of a plant hormone or selective agent for a plant tissue culture from an inner matrix containing crystals of the desired agent through an outer diffusion limiting membrane. A preferred embodiment of the formulation is to mix 30% dry crystals of the desired agent with 70% (w/w) room temperature vulcanizing (RTV) silicone which is then injected into silicone tubing having an appropriate diameter and wall thickness for the desired release rate of the desired agent. (The preferred agents for employing in connection with the slow release capsules are 2,4-D and NAA, and the preferred dimensions are 0.062" ID×0.125" OD).

The RTV silicone is then polymerized at room temperature or at a higher temperature to accelerate the vulcanization process. Following vulcanization of the inner matrix, the tubing is cut to desired lengths and the ends sealed with RTV silicone. The preferred lengths for use in connection with the present invention are about 0.5 cm. After the end seals have polymerized, the resulting capsules can either be stored, as is, or autoclaved for 15 minutes on a fast exhaust cycle and stored indefinitely in a sterile form. Prior to use the capsules may be equilibrated to establish a stable diffusion gradient across the membrane, or used directly without equilibration.

Another formulation for a much lower release rate is to enclose crystals of a desired substance suspended in a liquid such as water or silicone oil in a relatively nonpermeable tubing such as Nylon-11. The release rate from this reservoir can then be regulated by drilling various size holes in the tubing and gluing a silicone window over the hole with silicone medical adhesive. Once again the capsules can be sterilized by autoclaving and stored dry until use.

An exemplary technique employed by the inventors for preparing slow release hormone capsules is as follows:

1. Two grams of Dow Corning MDX-4-4210 medical grade elastomer and 0.2 grams of Dow Corning MDX-4-4210 curing agent were weighed into a 10 ml syringe, the bottom of which was capped with a plastic cap.
2. Six-hundred mg of 2,4-D (or NAA), from which lumps have been removed by sieving through a 411$\mu$ stainless steel sieve, was added to the same syringe and thoroughly mixed with the elastomer and curing agent.
3. The 10 ml syringe and its contents were then degassed for ½ hr in a vacuum centrifuge to remove bubbles.
4. Dow Corning Silastic medical grade silicone tubing (0.062" ID×0.125" OD) of medium durometer (50 Shore A) was preswelled 10 to 30 minutes by soaking in acetone.
5. The plastic cap was removed from the end of the 10 ml syringe and the degassed silicone-2,4-D mixture was extruded into the preswollen tubing from which excess acetone had been removed by blowing a stream of air briefly through it.
6. Both ends of the filled tubing were then clamped shut and the tubing heated at 50 degrees (the boiling point of acetone=56.5 degrees) overnight to accelerate the polymerization.
7. The tubing was then cut into 0.5 cm lengths.
8. The ends of the tubing sections were sealed with Dow Corning Type A medical adhesive and allowed to dry for 24 hr.
9. The finished capsules are autoclaved dry for 15–20 min and stored dry until use.
10. Before use the capsules may be preequilibrated for 48 hr by shaking in 25 ml of sterile 1 to 10 mM KHCO$_3$, or added to cultures without equilibration.

D. Cryopreservation Methods

Cryopreservation is important not only because it allows one to maintain and preserve a cell culture for future use, but it also is believed by the inventors that this may be a means for enriching for recipient cells.

Cell suspensions were cryopreserved using modifications of methods previously reported (15,49). The cryopreservation protocol comprised adding a pre-cooled (0° C.) concentrated cryoprotectant mixture dropwise over a period of one hour while stirring the cell suspension, which was also maintained at 0° C. during this period. The volume of added cryoprotectant was equal to the initial volume of the cell suspension (1:1 addition), and the final concentration of cryoprotectant additives was 10% dimethyl sulfoxide, 10% polyethylene glycol (6000 MW), 0.23M proline and 0.23M glucose. The mixture was allowed to equilibrate at 0° C. for 30 minutes, during which time the cell suspension/cryoprotectant mixture was divided into 1.5 ml aliquot (0.5 ml packed cell volume) in 2 ml polyethylene cryo-vials. The tubes were cooled at 0.5° C./minute to −8° C. and held at this temperature for ice nucleation.

Once extracellular ice formation had been visually confirmed, the tubes were cooled at 0.5° C./minute from −8° to −35° C. They were held at this temperature for 45 minutes (to insure uniform freeze-induced dehydration throughout the cell clusters). At this point, the cells had lost the majority of their osmotic volume (i.e. there is little free water left in the cells), and they could be safely plunged into liquid nitrogen for storage. The paucity of free water remaining in the cells in conjunction with the rapid cooling rates from −35° to −196° C. prevented large organized ice crystals from forming in the cells. The cells are stored in liquid nitrogen, which effectively immobilizes the cells and slows metabolic processes to the point where long-term storage should not be detrimental.

Thawing of the extracellular solution was accomplished by removing the cryo-tube from liquid nitrogen and swirling it in sterile 42° C. water for approximately 2 minutes. The tube was removed from the heat immediately after the last ice crystals had melted to prevent heating the tissue. The cell suspension (still in the cryoprotectant mixture) was pipetted onto a filter, resting on a layer of agarose-immobilized BMS cells (the feeder layer which provided a nurse effect during recovery). Dilution of the cryoprotectant occurred slowly as the solutes diffused away through the filter and nutrients diffused upward to the recovering cells. Once subsequent growth of the thawed cells was noted, the growing tissue was transferred to fresh culture medium. The cell clusters were transferred back into liquid suspension medium as soon as sufficient cell mass had been regained (usually within 1 to 2 weeks). After the culture was reestablished in liquid (within 1 to 2 additional weeks), it was used for transformation experiments. When necessary, previously cryopreserved cultures may be frozen again for storage.

E. DNA segments Comprising Exogenous Genes

As mentioned previously, there are several methods to construct the DNA segments carrying DNA into a host cell that are well known to those skilled in the art. The general construct of the vectors used herein are plasmids comprising a promoter, other regulatory regions, structural genes, and a 3' end.

DNA segments encoding the bar gene were constructed into a plasmid, termed pDPG165, which was used to introduce the bialaphos resistance gene into recipient cells (see FIGS. 1A and C). The bar gene was cloned from *Streptomyces hygroscopicus* (53) and exists as a 559-bp Sma I fragment in plasmid pIJ4101. The sequence of the coding region of this gene is identical to that published (45). To create plasmid pDPG165, the Sma I fragment from pIJ4104 was ligated into a pUC19-based vector containing the Cauliflower Mosaic Virus (CaMV) 35S promoter (derived from pBI221.1. provided by R. Jefferson, Plant Breeding Institute, Cambridge, England), a polylinker, and the transcript 7 (Tr7) 3' end from Agrobacterium tumefaciens (3' end provided by D. Stalker, Calgene, Inc., Davis, Calif.).

An additional vector encoding GUS, pDPG208, (FIGS. 1B and D) was used in these experiments. It was constructed using a 2.1 kb BamHI/EcoRI fragment from pAGUS1 (provided by J. Skuzeski, University of Utah, Salt Lake City, Utah) containing the coding sequence for GUS and the nos 3'-end from Agrobacterium tumefaciens. In pAGUS1 the 5'-noncoding and 5'-coding sequences for GUS were modified to incorporate the Kozak consensus sequence (24) and to introduce a new HindIII restriction site 6 bp into the coding region of the gene (see FIG. 1E). The 2.1 kb BamHI/EcoRI fragment from pAGUS1 was ligated into a 3.6 kb BamHI/EcoRI fragment of a pUC19-based vector pCEV1 (provided by Calgene, Inc., Davis, Calif.). The 3.6 kb fragment from pCEV1 contains pUC19 and a 430 bp 35S promoter from cauliflower mosaic virus adjacent to the first intron from maize Adh1.

In terms of a member of the R gene complex for use in connection with the present invention, the most preferred vectors contain the 35S promoter from Cauliflower mosaic virus, the first intron from maize Adh1, the Kozak consensus sequence, Sn:bol3 cDNA, and the transcript 7 3' end from *Agrobacterium tumefaciens*. One such vector prepared by the inventors is termed pDPG237. To prepare pDPG237 (see FIG. 1F), the cDNA clone of Sn:bol3 was obtained from S. Dellaporta (Yale University, USA). A genomic clone of Sn was isolated from genomic DNA of Sn:bol3 which had been digested to completion with HindIII, ligated to lambda arms and packaged in vitro. Plaques hybridizing to two regions of cloned R alleles, R-nj and R-sc (97) were analyzed by restriction digest. A 2 kb Sst-HincII fragment from the pSn7.0 was used to screen a cDNA library established in lambda from RNA of light-irradiated scutellar nodes of Sn:bol3. The sequence and a restriction map of the cDNA clone was established.

Figure 1B:
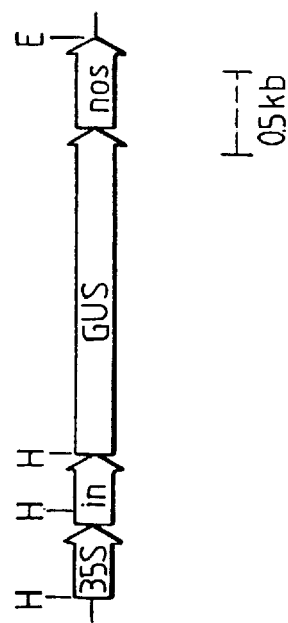
Figure 1C:
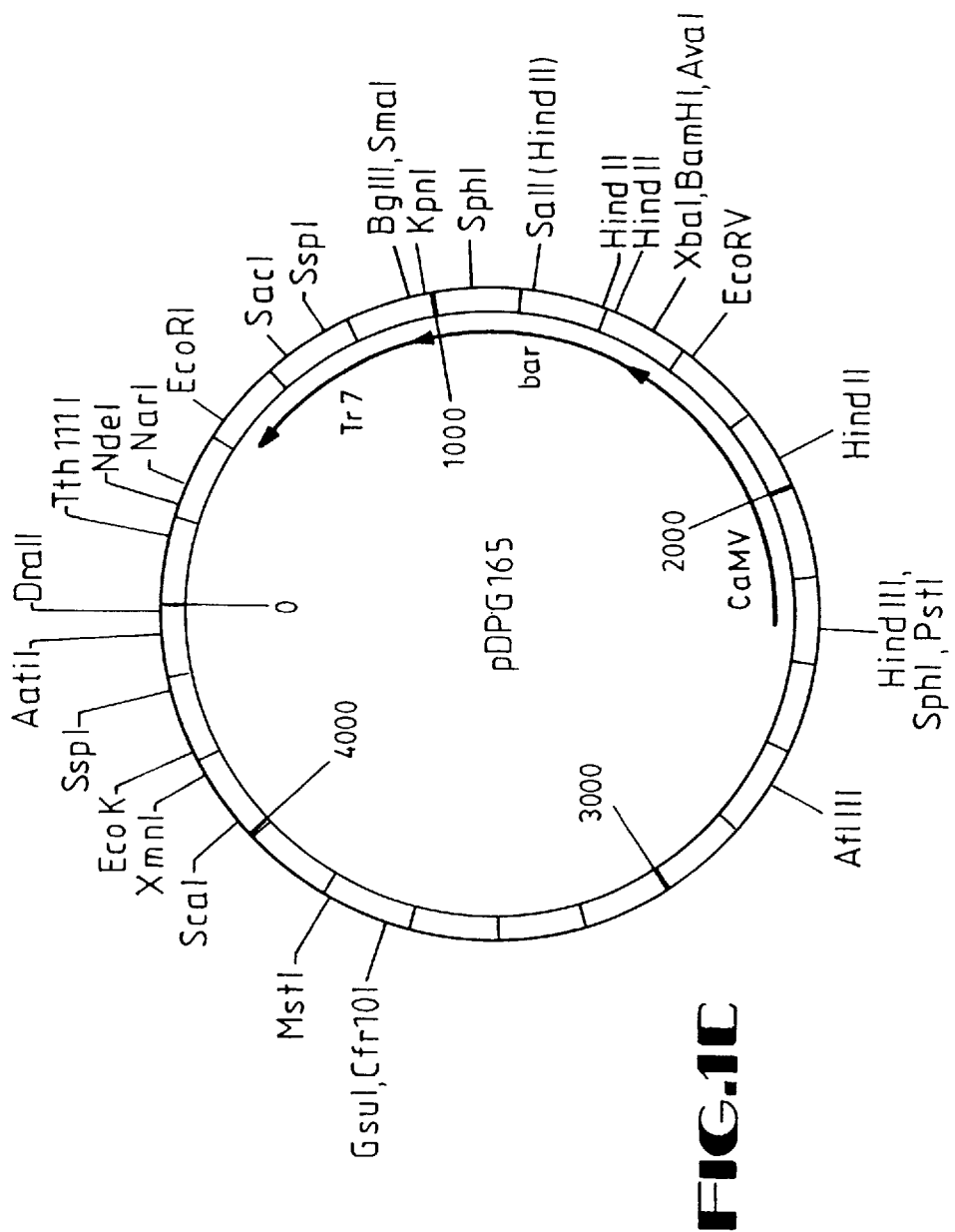
Figure 1D:
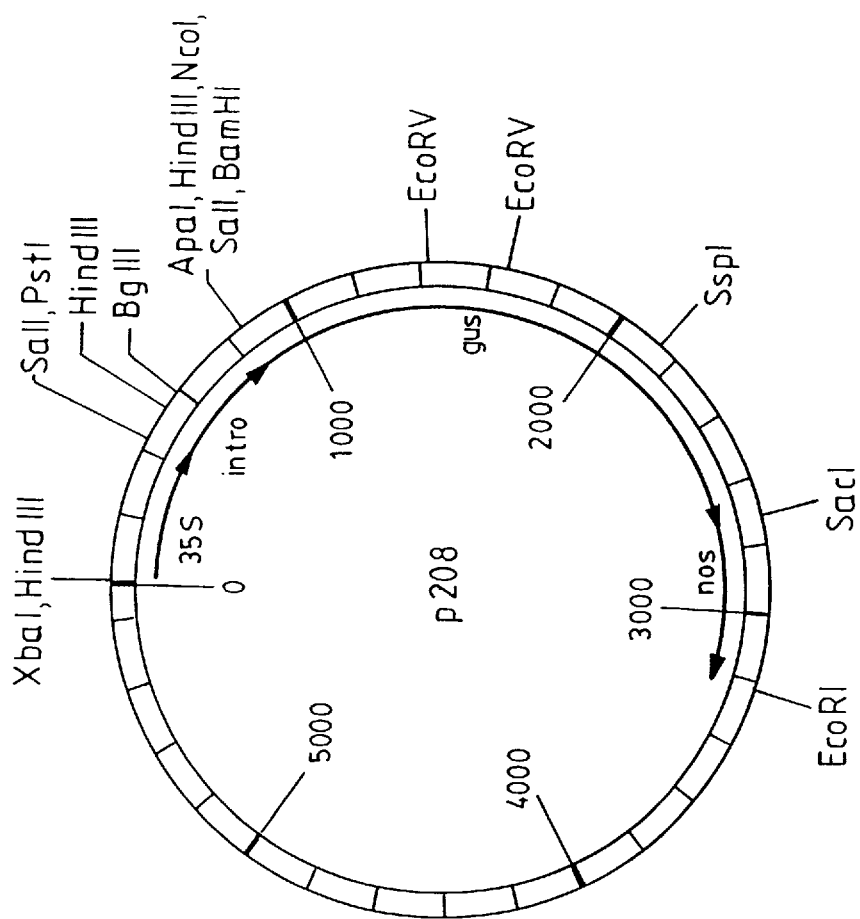

The cDNA clone was inserted into the same plant expression vector described for pDPG165, the bar expression vector (see above), and contains the 35S Cauliflower mosaic virus promoter, a polylinker and the transcript 7 3' end from *Agrobacterium tumefaciens*. This plasmid, pPDG232, was made by inserting the cDNA clone into the polylinker region; a restriction map of pDPG232 is shown in FIG. 1G. The preferred vector, pDPG237, was made by removing the cDNA clone and Tr7 3' end from pDPG232, with AvaI and EcoRI and ligating it with a BamHI/EcoRI fragment from pDPG208. The ligation was done in the presence of a BamHI linker as follows:(SEQ ID NO:2 and SEQ ID NO:3)

GATCCGTCGACCATGGCGCTTCAAGCTTC
GCAGCTGGTACCGCGAAGTTCGAAGGGCT

Figure 1F:
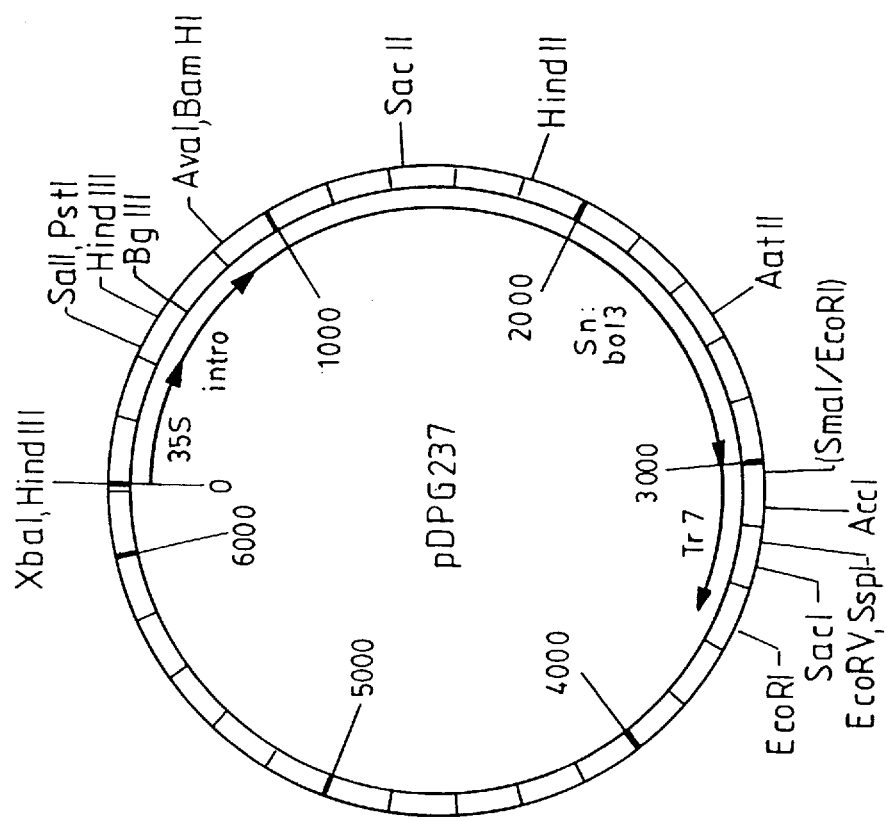
Figure 1G:
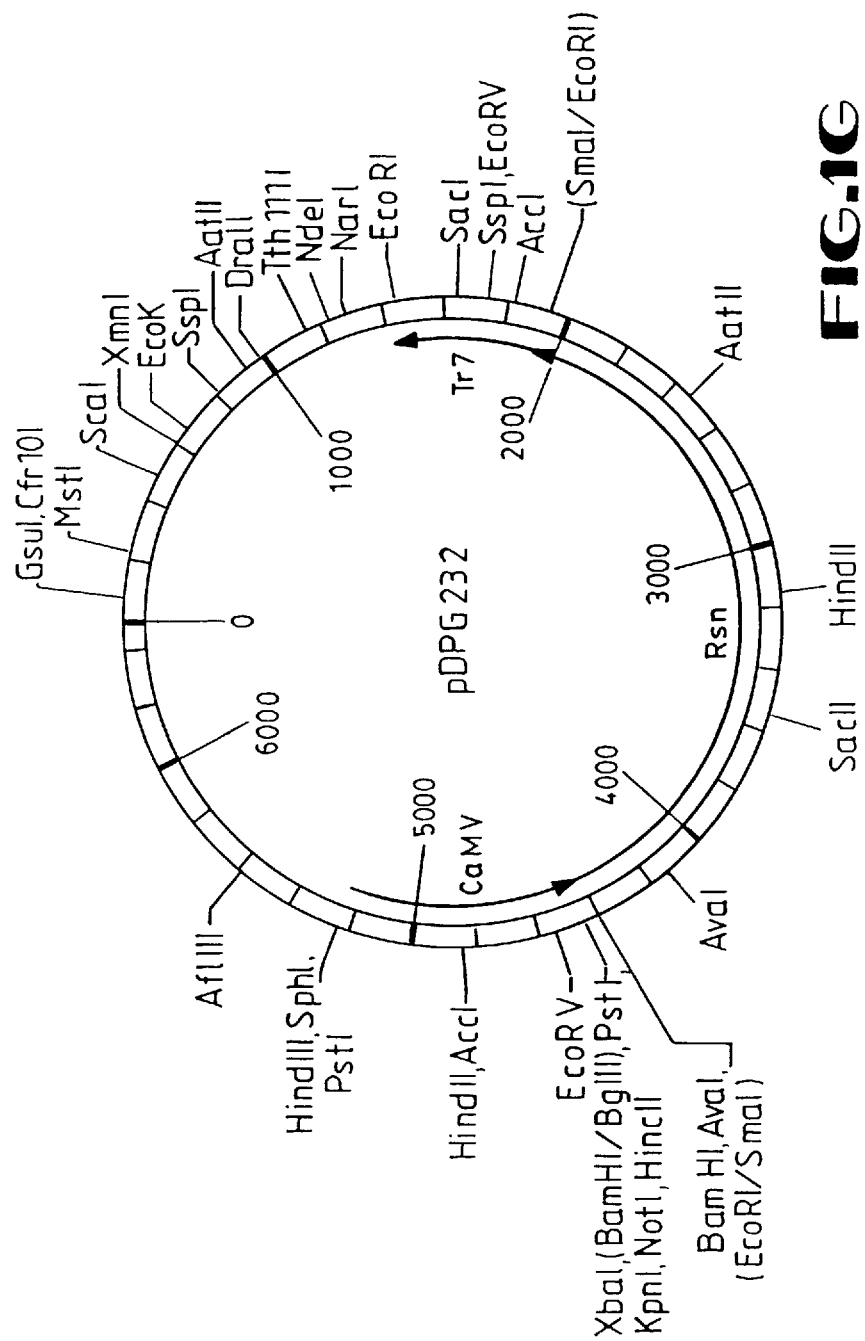

The final construct of pDPG237 contained a Cauliflower mosaic virus 35S promoter, the first intron of Adh1 , Kozak consensus sequence, the BamHI linker, cDNA of Sn:Bol3, and the Tr7 3' end and is shown in FIG. 1F.

Additional vectors have been prepared using standard genetic engineering techniques. For example, a vector, designated pDPG128, has been constructed to include the neo coding sequence (neomycin phosphotransferase (APH(3')-II)). Plasmid pDPG128 contains the 35S promoter from CaMV, the neomycin phosphotransferase gene from Tn5 (66) and the Tr7 terminator from *Agrobacterium tumefaciens*. Another vector, pDPG154, incorporates the crystal toxin gene and was also prepared by standard techniques. Plasmid pDPG154 contains the 35S promoter, the entire coding region of the crystal toxin protein of *Bacillus thuringiensis* var. kurstaki HD 263, and the Tr7 promoter.

Various tandem vectors have also been prepared. For example, a bar/aroA tandem vector was constructed by ligating a blunt-ended 3.2 kb DNA fragment containing a mutant EPSP synthase aroA expression unit (93) to NdeI-cut pDPG165 that had been blunted and dephosphorylated (NdeI introduces a unique restriction cut approximately 200 bp downstream of the Tr7 3'-end of the bar expression unit). Transformants having aroA in both orientations relative to bar were identified.

F. Preferred Methods of Delivering DNA to Cells

A preferred DNA delivery system that does not require protoplast isolation or introduction of Agrobacterium DNA is microprojectile bombardment (8,23). There are several potential cellular targets for microprojectile bombardment to produce fertile transgenic plants: pollen, microspores, meristems, and cultured embryogenic cells are but a few examples. Germline transformation in maize has not been previously reported by bombardment of any of these types.

One of the newly emerging techniques for the introduction of exogenous DNA constructs into plant cells involves the use of microprojectile bombardment. The details of this technique and its use to introduce exogenous DNA into various plant cells are discussed in Klein, 1989, Wang, et al., 1988 and Christou, et al., 1988 (22,50,8). One method of determining the efficiency of DNA delivery into the cells via microprojectile bombardment employs detection of transient expression of the enzyme β-glucuronidase (GUS) in bombarded cells. For this method, plant cells are bombarded with a DNA construct which directs the synthesis of the GUS enzyme.

Apparati are available which perform microprojectile bombardment. A commercially available source is an apparatus made by Biolistics, Inc. (now DuPont), but other microprojectile or acceleration methods are within the scope of this invention. Of course, other "gene guns" may be used to introduce DNA into cells.

Several modifications of the microprojectile bombardment method were made by the inventors. For example, stainless steel mesh screens were introduced below the stop plate of the bombardment apparatus, i.e., between the gun and the cells. Furthermore, modifications to existing techniques were developed by the inventors for precipitating DNA onto the microprojectiles.

EXAMPLE 3

Microprojectile Bombardment

For bombardment, friable, embryogenic Type-II callus (1) was initiated from immature embryos essentially as set forth above in Examples 1 and 2. The callus was initiated and maintained on N6 medium (5) containing 2 mg/l glycine, 2.9 g/l L-proline, 100 mg/l casein hydrolysate, 13.2 mg/l dicamba or 1 mg/l 2,4-D, 20 g/l sucrose, pH 5.8, solidified with 2 g/l Gelgro (ICN Biochemicals). Suspension cultures initiated from these callus cultures were used for bombardment.

In the case of SC82, suspension culture SC82 was initiated from Type-II callus maintained in culture for 3 months. SC82 cells (see Example 1) were grown in liquid medium for approximately 4 months prior to bombardment (see Table 2, experiments #1 and #2). SC82 cells were also cryopreserved 5 months after suspension culture initiation, stored frozen for 5 months, thawed and used for bombardment (experiment #6).

In the case of suspension culture SC716 (see Example 2), it was initiated from Type-II callus maintained 5 months in culture. SC716 cells were cultured in liquid medium for 5 months, cryopreserved for 8 months, thawed, and used two months later in bombardment experiments #4 and #5. SC94 was initiated from 10 month old Type-II callus; and cultured in liquid medium for 5 months prior to bombardment (experiment #3).

Prior to bombardment, recently subcultured suspension culture cells were sieved through 1000 μm stainless steel mesh. From the fraction of cell clusters passing through the sieve, approximately 0.5 ml packed cell volume (PCV) was pipetted onto 5 cm filters (Whatman #4) and vacuum-filtered in a Buchner funnel. The filters were transferred to petri dishes containing three 7 cm filters (Whatman #4) moistened with 2.5 ml suspension culture medium.

The dish containing the filters with the immobilized cell suspensions was positioned 6 cm below the lexan plate used to stop the nylon macroprojectile. With respect to the DNA, when more than a single plasmid was used, plasmid DNA was precipitated in an equimolar ratio onto tungsten particles (average diameter approximately 1.2 μm, GTE Sylvania) using a modification of the protocol described by Klein, et al. (1987). In the modified procedure, tungsten was incubated in ethanol at 65 degrees C. for 12 hours prior to being used for precipitation. The precipitation mixture included 1.25 mg tungsten particles, 25 μg plasmid DNA, 1.1 M $CaCl_2$ and 8.7 mM spermidine in a total volume of 575 μl. After adding the components in the above order, the mixture was vortexed at 4° C. for 10 min, centrifuged (500×G) for 5 min and 550 μl of supernatant was decanted. From the remaining 25 μl of suspension, 1 μl aliquots were pipetted onto the macroprojectile for bombardment.

Each plate of suspension cells was bombarded twice at a vacuum of 28 inches Hg. In bombarding the embryogenic suspensions of A188×B73 and A188×B84, 100 μm or 1000 μm stainless steel screens were placed about 2.5 cm below the stop plate in order to increase the number of foci while decreasing their size and also to ameliorate injury to the bombarded tissue. After bombardment, the suspension cells and the supporting filter were transferred onto solid medium or the cells were scraped from the filter and resuspended in liquid culture medium.

Cells from embryogenic suspension cultures of maize were bombarded with the bar-containing plasmid pDPG165 alone or in combination with a plasmid encoding GUS, pDPG208 (FIG. 1). In experiments in which a GUS plasmid was included, two of the filters containing bombarded cells were histochemically stained 48h post-bombardment. The total number of foci (clusters of cells) per filter transiently expressing GUS was at least 1000. In two separate studies designed to quantitate transiently expressing cells (using an SC82 (A188×B73) suspension culture), the mean number and standard deviation of GUS-staining foci per filter was 1472+/−211 and 2930+/−(n=3 and 4, respectively). The number of cells in individual foci that expressed GUS averaged 2–3 (range 1–10). Although histochemical staining can be used to detect cells transformed with the gene encoding GUS, those cells will no longer grow and divide after staining. For detecting stable transformants and growing them further, e.g., into plants, selective systems compatible with viability are required.

G. Methods of Identifying Transformed Cells

It is believed that DNA is introduced into only a small percentage of cells in any one experiment. In order to provide a more efficient system for identification of those cells receiving DNA and integrating it into their genomes, therefore, one may desire to employ a means for selecting those cells that are stably transformed. One exemplary embodiment of such a method is to introduce into the host cell, a marker gene which confers resistance to some agent, e.g. an antibiotic or herbicide. The potentially transformed cells are then exposed to the agent. In the population of surviving cells are those cells wherein generally the resistance-conferring gene has been integrated and expressed at sufficient levels to survive. Cells may be tested further to confirm stable integration of the exogenous DNA. Using embryogenic suspension cultures, stable transformants are recovered at a frequency of approximately 1 per 1000 transiently expressing foci. A specific embodiment of this procedure is shown in Example 5.

One of the difficulties in cereal transformation, e.g., corn, has been the lack of an effective selective agent for transformed cells, from totipotent cultures (36). Stable transformants were recovered from bombarded nonembryogenic Black Mexican Sweet (BMS) maize suspension culture cells, using the neo gene and selection with the aminoglycoside, kanamycin (22). This approach is limited because many monocots are insensitive to high concentrations of aminoglycosides (12,19). The stage of cell growth, duration of exposure and concentration of the antibiotic, may be critical to the successful use of aminoglycosides as selective agents to identify transformants (26,51,52). In addition, use of the aminoglycosides, kanamycin or G418, to select stable transformants from embryogenic maize cultures, in the inventors' experience, often results in the isolation of resistant calli that do not contain the neo gene.

One herbicide which has been suggested in resistance studies is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (33). Inhibition of GS in plants by PPT causes the rapid accumulation of ammonia and death of the plant cells.

The organism producing bialaphos also synthesizes an enzyme phosphinothricin acetyl transferase (PAT) which is encoded by the bar gene. The use of the herbicide resistance gene encoding phosphinothricin acetyl transferase (PAT) is referred to in DE 3642 829 A wherein the gene is isolated from *Streptomyces viridochromogenes*. This enzyme acetylates the free amino group of PPT preventing auto-toxicity (45). The bar gene has been cloned (29,45) and expressed in transgenic tobacco, tomato and potato plants (10) and Brassica (11). In previous reports, some transgenic plants which expressed the resistance gene were completely resistant to commercial PPT and bialaphos in greenhouses.

PCT Application No. WO 87/00141 refers to the use of a process for protecting plant cells and plants against the action of glutamine synthetase inhibitors. This application also refers to the use of such of a process to develop herbicide resistance in determined plants. The gene encoding resistance to the herbicide BASTA (Hoechst phosphinothricin) or Herbiace (Meiji Seika bialaphos) was said to be introduced by Agrobacterium infection into tobacco (*Nicotiana tabacum* cv Petit Havan SR1), potato (*Solanum tuberosum* cv Benolima) and tomato (*Lycopersicum esculentum*) and conferred on plants resistance to application of herbicides.

An exemplary embodiment of vectors capable of delivering DNA to plant host cells is the plasmid, pDPG165. This plasmid is illustrated in FIG. 1A and 1C. A very important component of this plasmid for purposes of genetic transformation is the bar gene which acts as a marker for selection of transformed cells.

EXAMPLE 4

Selection of bar Transformants Using Bialaphos

The suspension culture (designated SC82) used in the initial experiments (see Example 3) was derived from embryogenic Type-II callus of A188×B73. Following bombardment (see Example 3), cells on filters were resuspended in nonselective liquid medium, cultured for 1 to 2 weeks and transferred to filters overlaying solid medium containing 1 or 3 mg/l bialaphos. The degree of inhibition of tissue growth during selection was dependent upon the density of the cells on the filter and on the concentration of bialaphos used. At the density plated (0.5 PCV/filter), the growth of the cells cultured on 1 mg/l bialaphos was only partially inhibited (~30–50% of nonselected growth) and after 3 to 4 weeks much of this tissue was transferred as discrete clumps (~5 mm in diameter) to identical medium. On medium containing 3 mg/l bialaphos, the growth of cells on the original selection filter was severely inhibited (~10% of nonselected growth) and selection was carried out without removing the tissue from the original filter.

Figure 2A:
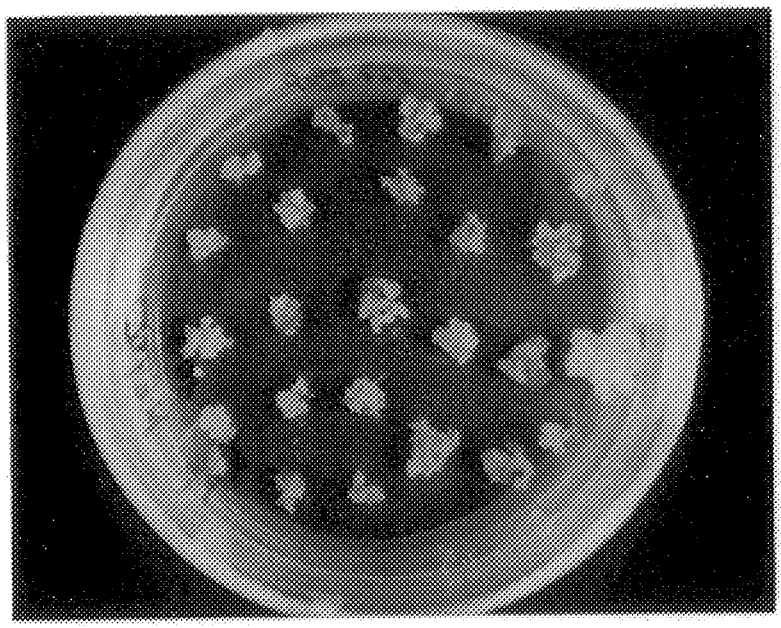
FIG. 2. Appearance of cell colonies which emerge on selection plates with bialaphos. Such colonies appear 6–7 weeks after bombardment. (A) SC82 bialaphos-resistant colony selected on 1 mg/l bialaphos. (B) Embryogenic SC82 bialaphos-resistant callus selected and maintained on 1 mg/l bialaphos.
Figure 2B:
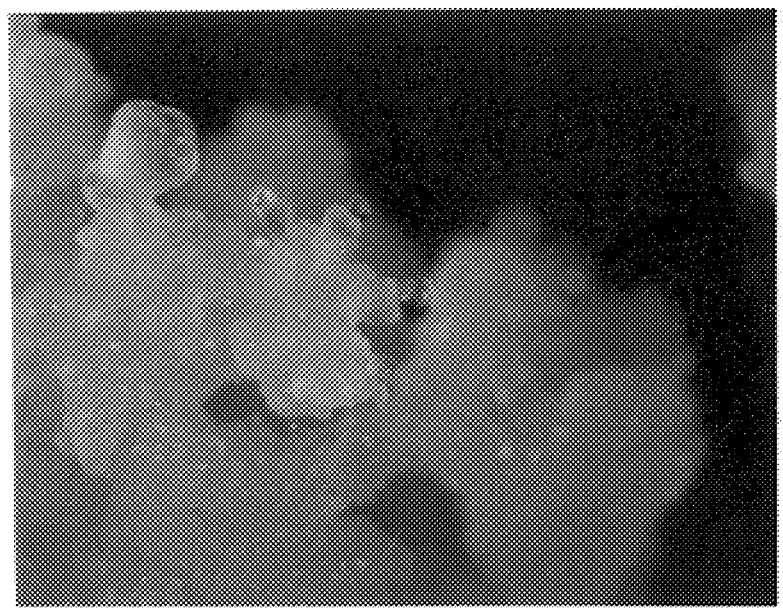

Using either selection protocol (1 or 3 mg/l bialaphos), resistant cell colonies emerged on the selection plates of SC82 bombarded with pDPG165 approximately 6 to 7 weeks after bombardment (FIG. 2A). Bialaphos-resistant calli were maintained and expanded on selection medium. Much of this tissue was embryogenic (FIG. 2B). No colony growth occurred on plates to which cells were added from suspension cultures on which no transforming attempts were made. These are controls which confirm the prediction that cells without the bar gene are not resistant to bialaphos.

Colonies on solid supports are visible groups of cells formed by growth and division of cells plated on such support. Colonies can be seen in FIG. 2A on a petri dish. In this figure, the cells capable of growth are those that are resistant to the presence of the herbicide bialaphos, said resistance resulting from integration and expression of the bar gene. Exposure of cells was to 1 mg/l bialaphos. FIG. 2B is a magnification showing the morphology of one bialaphos-resistant culture maintained on selection media indicating that growth is embryogenic.

As a confirmation that the cells forming the colonies shown in FIG. 2 had indeed incorporated the bar gene and were expressing it, bialaphos-resistant callus lines were analyzed for activity of the bar gene product, phosphinothricin acetyl transferase (PAT), by thin-layer chromatography. Protein extracts from eleven callus lines (E1–11) isolated from SC82 bombardment experiments contained PAT activity as shown in FIG. 3 and activity levels varied approximately 10-fold among the isolates.

Still further and more direct confirmation of the presence of the bar gene was obtained by analysis of the genomic DNA of potential transformants by DNA gel blots (FIG. 4). The sources of DNA which were electrophoresed through the gel were the bialaphos-resistant callus lines designated E1–E11 and a non-selected control, EO. (FIG. 1 indicates the cleavage sites of those enzymes within the bar gene plasmid.) After the DNA was electrophoresed through the gel and transferred to nylon membranes, the resulting blot was hybridized with a 32P-labeled bar gene sequence from the plasmid pDPG165. The radioactivity used per blot was approximately $25\times10^6$ Cerenkov cpm. The lane in FIG. 4 designated "1" and "5" copies contain 1.9 and 9.5 pg respectively of the 1.9 kb bar expression unit released from the plasmid pDPG165 by application of the EcoRI and HindIII enzymes; these amounts represent about 1 and 5 copies per diploid genome.

Genomic DNA from all eleven bialaphos-resistant isolates contained bar-hybridizing sequences as shown in FIG. 4. The hybridization in all isolates to a fragment migrating slightly larger than 2 kb may be due to contaminating pUC19 sequences contained in this bar probe preparation; no such hybridization occurred in subsequent experiments using the same genomic DNA and a different preparation of the bar probe. Hybridization to a 1.9 kb fragment in eight of the eleven isolates indicated that these isolates contained intact copies of the 1.9 kb bar expression unit. The estimated copy numbers of the intact unit ranged from one or two (E1, E7, E8, E10, E11) to approximately 20 (E3, E4, E6). Hybridization with the bar probe in isolates E2 and E5 occurred only to a single, higher molecular weight fragment (~3 kb).

To establish that the PAT coding sequence was intact in isolates E2 and E5, genomic DNA was digested with SmaI, which releases a 559 bp fragment containing the PAT structural gene (FIG. 1A), and subjected to DNA gel blot analysis using 32P-labeled bar. This analysis confirmed the presence of a single intact copy of bar. Expression of PAT in these isolates may not be dependent on the 35S promoter or the Tr7 3' end. The hybridization patterns of some of the isolates were identical (E2 and E5; E7 and E8; E3, E4, and E6); therefore, it is probable that some isolates did not arise from independent transformation events but represent transformants that were separated during selection.

Seven hybridization patterns were unique, likely representing seven independent single-cell transformation events. The patterns and intensities of hybridization for the seven transformants were unchanged during four months in culture, providing evidence for the stability of the integrated sequences. The seven independent transformants were derived from two separate bombardment experiments. Four independent transformants representing isolates E2/E5, E3/E4/E6, E1 and E7/E8, were recovered from a total of four original filters from bombardment experiment #1 and the three additional independent transformants, E9, E10, and E11, were selected from tissue originating from six bombarded filters in experiment #2. These data are summarized in Table 2.

bar-hybridizing sequences and levels of PAT expression were comparable to the studies described above.

EXAMPLE 5

Integration of the Bar Gene into Cell Lines Derived from the SC716 Suspension Culture Bombardment studies and subsequent analyses were also performed on the A188×B73 suspension culture, termed SC716 (see Example 1). The resultant transformed plant cells were analyzed for integration of bar genes. To carry out this analysis, genomic DNA was obtained from R1–R21 isolates; 6 $\mu$g of DNA was digested with the restriction endonucleases EcoRI and HindIII, and DNA gel blot analysis was performed using the bar gene as probe. In FIG. 9, molecular weights in kb are shown to the right and left. The untransformed control is designated "R0," and the last column to the right contains the equivalent of two copies of the bar gene expression unit per diploid genome. For the DNA load used, two copies the bar expression unit per diploid genome is 5.7 pg of the 1.9 kb EcoRI/Hind fragment from the plasmid pDPG165. The DNA separated on the gel blot was hybridized to a $^{32}$P-labeled bar probe. The label activity in the hybridization was approximately 10×10$^6$ Cerenkov cpm. In A, the presence of an intact bar expression unit is inferred from the hybridization of the bar probe to a 1.9 kb band in the gel.

EXAMPLE 6

Assays for Integration and Expression of GUS

SC716 transformants discussed in Example 5, were further analyzed for integration and expression of the gene encoding GUS. As determined by histochemical assay, four of the SC716 transformants (R5, R7, R16, and R21) had detectable GUS activity 3 months post-bombardment. Expression patterns observed in the four coexpressing callus lines varied. The number of cells with GUS activity within any given transformant sampled ranged from ~5% to ~90%

TABLE 2

Summary of Maize Transformation Experiments

| Exp. # | Culture Bombarded | # of Filters Bombarded | # of Independent bar Transformants Recovered | # with Intact bar Expression Units | # with GUS Coding Sequence | # with GUS Activity | Cointegration Frequency (%) | Coexpression Frequency (%) |
|---|---|---|---|---|---|---|---|---|
| 1 | SC82   | 4  | 4  | 3  | n.a. |   |         |         |
| 2 | SC82   | 6  | 3  | 2  | n.a. |   |         |         |
| 3 | SC94   | 10 | 8  | 6  | n.a. |   |         |         |
| 4 | SC716* | 8  | 13 | 8  | 11   | 3 | 85      | 23      |
| 5 | SC716* | 8  | 7  | 4  | 6    | 1 | 86      | 14      |
| 6 | SC82*  | 4  | 19 | 17 | 13   | 3 | 68      | 16      |
|   | Totals | 40 | 54 | 40 | 30   | 7 | 77(30/39) | 18(7/39) |

Figure 9B:
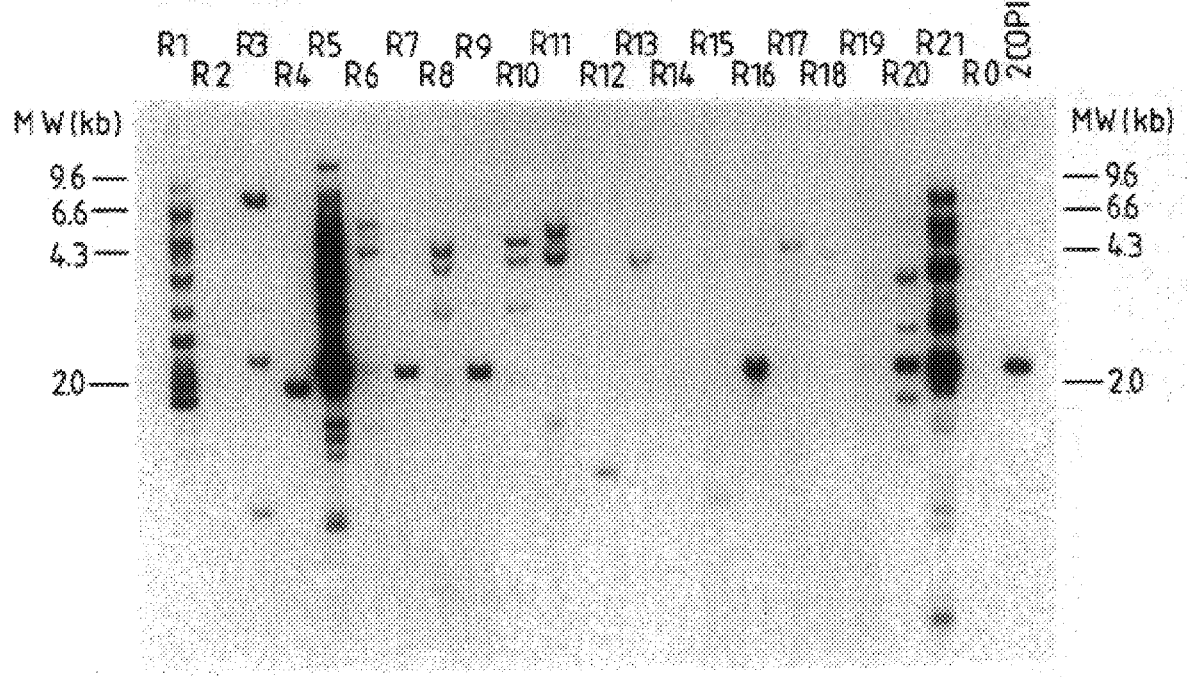
FIG. 9. Integration of exogenous genes in bialaphos-resistant SC716 isolates R1–R21. (A) DNA gel blot of genomic DNA (6 μg/digest) from transformants isolated from suspension culture of A188×B73 (SC716), designated R1–R21, were digested with EcoRI and HindIII and hybridized to $^{32}$P-labeled bar probe (~10×10$^6$ Cerenkov cpm). Molecular weight markers in kb are shown on the left and right. Two copies of the bar expression unit per diploid genome is 5.7 pg of the 1.9 kb EcoRI/Hind fragment from pDPG165. (B) The blot from A was washed and hybridized with $^{32}$P-labelled GUS probe (~35×10$^6$ Cerenkov cpm). Two copies of the 2.1 kb GUS-containing EcoRI/HindIII fragment from pDPG208 is 6.3 pg.

*culture reinitiated from cryopreserved cells
n.a. not applicable; only pDPG165 DNA used or cotransformation analysis not done Studies with other embryogenic suspension cultures produced similar results. Using either an SC82 culture that was reinitiated from cryopreserved cells (experiment #6) or an A188×B84 (SC94) suspension culture (experiment #3), numerous independent transformants were recovered (19 and 18 respectively; Table 2). All transformants contained the bar gene and expressed PAT. The copy number of and, in addition, the level of GUS activity within those cells varied. The cointegration frequency was determined by washing the genomic blot hybridized with bar (FIG. 9A) and probing with $^{32}$P-labeled GUS sequence as shown in FIG. 9B. EcoRI and HindIII, which excise the bar expression unit from pDPG165, also release from pDPG208 a 2.1 kb fragment containing the GUS coding sequence and the nos 3' end (FIG. 1B).

Seventeen of the independent bar transformants contained sequences that hybridized to the GUS probe; three, R2, R14 and R19 did not. Transformants in which GUS activity was detected (R5, R7, R16 and R21) had intact copies of the 2.1 kb EcoRI/HindIII fragment containing the GUS structural gene (FIG. 9B). Transformants that contained large numbers of fragments that hybridized to bar (R1, R5, R21) also contained comparable number of fragments that hybridized to the gene encoding GUS (FIGS. 9A and B). This observation is consistent with those reported using independent plasmids in PEG-mediated transformation of A188 X BMS protoplasts (Lyznik, et al., 1989) and in studies conducted by the inventors involving bombardment-mediated transformation of BMS suspension cells.

H. Co-Transformation

Co-transformation may be achieved using a vector containing the marker and another gene or genes of interest. Alternatively, different vectors, e.g., plasmids, may contain the different genes of interest, and the plasmids may be concurrently delivered to the recipient cells. Using this method, the assumption is made that a certain percentage of cells in which the marker has been introduced, have also received the other gene(s) of interest. As can be seen in the following examples, not all cells selected by means of the marker, will express the other genes of interest which had been presented to the cells concurrently. For instance, in Example 7, successful cotransformation occurred in 17/20 independent transformants (see Table 2), coexpression occurred in 4/20. In some transformants, there was variable expression among transformed cells.

EXAMPLE 7

Figure 8:
FIG. 8. Histochemical determination of GUS activity in bar-transformed SC82 callus line Y13. This bialaphos-resistant callus line, Y13, which contained intact GUS coding sequences was tested for GUS activity three months post-bombardment. In this figure, differential staining of the callus was observed.

Co-Integration and Co-Expression of the Bar Gene and the GUS Gene to Cell Lines Derived from the SC82 Suspension Culture Of the bialaphos-resistant isolates selected from a reinitiation of cryopreserved SC82 cells transformed with separate plasmids (as described for SC716), nineteen independent transformants were selected in this experiment (experiment #6, Table 2). The frequency of cointegration and coexpression in those isolates was similar to that described for SC716 isolates (Table 2). The pattern of GUS staining in these transformants varied in a manner similar to that described for coexpressing SC716 transformants. A transformant, Y13, which contained intact GUS coding sequence, exhibited varying levels of GUS activity as shown in FIG. 8. This type of expression pattern has been described previously in cotransformed BMS cells (Klein, et al., 1989). Variable activity detected in the cells from a single transformant may be attributed to unequal penetration of the GUS substrate, or differential expression, methylation, or the absence of the gene in some cells.

These results show that both the bar gene and the GUS gene are present in some of the cells bombarded with the two plasmids containing these genes. Co-transformation has occurred. In the cotransformation examples described herein and summarized in Table 2, cotransformation frequency of the non-selected gene was 77%; coexpression frequency was 18%.

I. Regeneration of Plants From Transformed Cells

For use in agriculture, transformation of cells in vitro is only one step toward commercial utilization of these new methods. Plants must be regenerated from the transformed cells, and the regenerated plants must be developed into full plants capable of growing crops in open fields. For this purpose, fertile corn plants are required. The invention disclosed herein is the first successful production of fertile maize plants (e.g., see FIG. 11A) from transformed cells.

During suspension culture development, small cell aggregates (10–100 cells) are formed, apparently from larger cell clusters, giving the culture a dispersed appearance. Upon plating these cells to solid media, somatic embryo development can be induced, and these embryos can be matured, germinated and grown into fertile seed-bearing plants. The characteristics of embryogenicity, regenerability, and plant fertility are gradually lost as a function of time in suspension culture. Cryopreservation of suspension cells arrests development of the culture and prevents loss of these characteristics during the cryopreservation period.

One efficient regeneration system involves transfer of embryogenic callus to MS (Murashige and Skoog, 1962) medium containing 0.25 mg/l 2,4-dichlorophenoxyacetic acid and 10.0 mg/l 6-benzyl-aminopurine. Tissue was maintained on this medium for approximately 2 weeks and subsequently transferred to MS medium without hormones (Shillito, et al., 1989). Shoots that developed after 2–4 weeks on hormone-free medium were transferred to MS medium containing 1% sucrose and solidified with 2 g/l Gelgro$^R$ in Plant Con$^R$ containers where rooting occurred.

Another successful regeneration scheme involved transfer of embryogenic callus to N6 (Chu, et al., 1975) medium containing 6% sucrose and no hormones (Armstrong and Green, 1985) for two weeks followed by transfer to MS medium without hormones as described above. Regeneration was performed at 25° C. under fluorescent lights (250 microeinsteins·m$^{-2}$·s$^{-1}$). After approximately 2 weeks developing plantlets were transferred to soil, hardened off in a growth chamber (85% relative humidity, 600 ppm $CO_2$, 250 microeinsteins·m$^{-2}$·s$^{-1}$), and grown to maturity either in a growth chamber or the greenhouse.

Regeneration of plants from transformed cells requires careful attention to details of tissue culture techniques. One of the major factors is the choice of tissue culture media. There are many media which will support growth of plant cells in suspension cultures, but some media give better growth than others at different stages of development. Moreover, different cell lines respond to specific media in different ways. A further complication is that treatment of cells from callus initiation through transformation and ultimately to the greenhouse as plants, requires a multivariate approach. A progression consisting of various media types, representing sequential use of different media, is needed to optimize the proportion of transformed plants that result from each cell line. Table 3 illustrates sequential application of combinations of tissue culture media to cells at different stages of development. Successful progress is ascertained by the total number of plants regenerated.

TABLE 3

Plants to Soil From Bombardment of SC716 (Expts 1, 2; Table 2).
REGENERATION MEDIA PROGRESSIONS

| Cell Line | 227b 101 | 227b 171 101 | 227b 201b 171 101 | 227b 52 171 101 | 227b 163 171 191 | 227b 205 171 101 | 227b 173 101 | 227b 201b 173 101 | 227b 205 173 101 | 227b 163 173 101 | 227b 177 101 | 227b 201b 177 101 | # PLANTS TO SOIL |
|---|---|---|---|---|---|---|---|---|---|---|---|---|---|
| CONTROLS | | | | | | | | | | | | | |
| A01C-11 | X | 4 | X | X | X | X | 2 | X | X | X | X | X | 6* |
| A01C-01 | X | 7 | X | X | X | X | 27 | X | X | X | X | X | 34* |
| TOTAL CONTROLS | X | 11 | X | X | X | X | 29 | X | X | X | X | X | 40* |
| TRANSFORMED | | | | | | | | | | | | | |
| A01C-11 | X | X | X | 0 | 0 | 0 | X | X | 0 | 0 | X | X | 0 |
| A01C-12 | X | 2 | X | 0 | 0 | 0 | X | X | 0 | 0 | X | X | 2 |
| A01C-13 | X | 5 | 1 | 4 | 0 | 0 | 1 | 1 | 1 | 1 | X | X | 14* |
| A01C-14 | X | 2 | X | 0 | 0 | 0 | X | X | 1 | 0 | X | X | 3* |
| A01C-15 | X | 28 | 0 | 12 | 7 | 1 | 23 | 13 | 0 | 0 | 0 | 0 | 84* |
| A01C-17 | X | 7 | 0 | 0 | 0 | 0 | 17 | 0 | 0 | 0 | 0 | 0 | 24 |
| A01C-18 | X | 12 | 0 | 0 | X | 0 | 21 | 10 | 0 | X | 2 | 0 | 45* |
| A01C-19 | X | 0 | X | X | 0 | X | 0 | X | X | 0 | X | 0 | 0 |
| A01C-20 | X | 10 | X | 0 | 0 | X | 0 | X | X | 0 | X | 0 | 10* |
| A01C-21 | X | 0 | X | X | X | X | 0 | X | X | X | X | 0 | 0 |
| A01C-24 | 2 | 4 | 0 | 0 | 0 | 0 | 6 | 5 | 0 | 0 | 0 | 0 | 17* |
| A01C-25 | X | 9 | X | X | 0 | 0 | 1 | X | 0 | 0 | X | X | 10 |
| A01C-27 | X | 0 | X | X | X | X | 10 | X | X | X | X | 0 | 10* |
| TOTAL COMBINED | 2 | 79 | 1 | 16 | 7 | 1 | 79 | 29 | 2 | 1 | 2 | 0 | 219* |
| CONTROLS | X | 11 | X | X | X | X | 29 | X | X | X | X | X | 40* |
| TRANSFORMED | 2 | 79 | 1 | 16 | 7 | 1 | 79 | 29 | 2 | 1 | 2 | 0 | 219* |
| TOTAL | 2 | 90 | 1 | 16 | 7 | 1 | 108 | 29 | 2 | 1 | 2 | 0 | 259* | x = Regeneration not attempted by this route.
* = More plants could have been taken to soil.
201b = 201 with 1 mg/1 bialophos.
227b = 227 with 1 mg/1 bialophos.

It can be seen that using the same group of media, cell lines will vary in their success rates (number of plants) (Table 3). There was also variation in overall success rate, line AO1–15 yielding the greatest number of plants overall. (It should be noted, however, that because tissue was limiting not all combinations of media were used on all lines, therefore, overall comparisons are limited.)

A preferred embodiment for use on cell lines in general, at least initially, is the combination shown in the second column under the regeneration media progression (media 227, 171, 101, 501). Media 227 is a good media for the selective part of the experiments, for example, to use for growth of callus in the presence of bialaphos. This media contains the hormone dicamba. NAA and 2,4-D are hormones in other media. In liquid media, these are usually encapsulated for controlled release (see Example 12 hereinbelow).

Thus, it can be seen from Table 1 that the various media are modified so as to make them particularly applicable to the development of the transformed plant at the various stages of the transformation process. For example, subculture of cells in media 171 after applying the selective agent, yields very small embryos. Moreover, it is believed that the presence of BAP in the media facilitates development of shoots. Myo-inositol is believed to be useful in cell wall synthesis. Shoot elongation and root development proceeds after transfer to media 101. 101 and 501 do not contain the hormones that are required for earlier stages of regeneration.

Transfer of regenerating plants is preferably completed in an agar-solidified media adapted from a nutrient solution developed by Clark (1982; ref. 6), media 501. The composition of this media facilitates the hardening of the developing plants so that they can be transferred to the greenhouse for final growth as a plant. The salt concentration of this media is significantly different from that of the three media used in the earlier stages, forcing the plant to develop its own metabolic pathways. These steps toward independent growth are required before plants can be transferred from tissue culture vessels (e.g. petri dishes, plant cans) to the greenhouse.

Approximately 50% of transformed callus lines derived from the initial SC82 and SC716 experiments were regenerable by the routes tested. Transgenic plants were regenerated from four of seven independent SC82 transformants and ten of twenty independent SC716 transformants.

Regeneration of thirteen independently, transformed cell lines and two control lines of SC716 was pursued. Regeneration was successful from ten of thirteen transformants. Although a total of 458 plantlets were regenerated, due to time and space constraints only 219 transformed plants (representing approximately 48% of the total number of regenerants) were transferred to a soilless mix (see below). Approximately 185 plants survived. Twelve regeneration protocols were investigated and the number of plants regenerated from each route has been quantified (Table 3). There appeared to be no significant advantage to maturing the tissues on 201, 52, 163, or 205 (see Table 1 for media codes) prior to transfer to medium 171 or 173. The majority of the plants were generated by subculturing embryogenic callus directly from 227 to either 171 or 173. These plantlets developed roots without addition of exogenous auxins, and plantlets were then transferred to a soilless mix, as was necessary for many of the transformants regenerated from SC82.

The soilless mix employed comprised Pro Mix, Micromax, Osmocote 14—14—14 and vermiculite. Pro Mix is a commercial product used to increase fertility and porosity as well as reduce the weight of the mixture. This is the bulk material in the mixture. Osmocote is another commercial product that is a slow release fertilizer with a nitrogen-phosphorus-potassium ratio of 14:14:14. Micromax is another commercial fertilizer that contains all of the essential micronutrients. The ratio used to prepare the soilless mix was: 3 bales (3 ft$^3$ each) Pro Mix; 10 gallons (vol.) vermiculite; 7 pounds Osmocote; 46 ml Micromax. The soilless mix may be supplemented with one or two applications of soluble Fe to reduce interveinal chlorosis during early seedling and plant growth.

Regeneration of transformed SC82 selected cell lines yielded 76 plants transferred to the soilless mix, and 73 survived. The plants were regenerated from six bialaphos-resistant isolates, representing four of seven clonally independent transformants. Eighteen protocols were used successfully to regenerate the seventy six plants (Table 4). Differences in morphology between cell lines deemed some protocols more suitable than others for regeneration.

solidified with Gelgro. Plantlets which were slow to develop roots were treated with 3 μl droplets of 0.3% IBA at the base of the shoot to stimulate rooting. Plants with well developed root systems were transferred to a soilless mix and grown in controlled environmental chambers from 5–10 days, prior to transfer to the greenhouse.

Figure 10A:
FIG. 10. Functional Expression of Introduced Genes in Transformed $R_o$ and $R_1$ Plants. (A) Basta$^R$ resistance in transformed $R_o$ plants. A Basta$^R$ solution was applied to a large area (about 4×8 cm) in the center of leaves of non-transformed A188×B73 plant (left) and a transgenic Ro E3/E4/E6 plant (right). (B) Basta$^R$ resistance in transformed $R_1$ plants. Basta$^R$ was also applied to leaves of four $R_1$ plants; two plants without bar (left) and two plants containing bar (right). The herbicide was applied to $R_1$ plants in 1 cm circles to four locations on each leaf, two on each side of the midrib. Photographs were taken six days after application. (C) GUS activity in leaf tissue of a transgenic $R_o$ plant. Histochemical determination of GUS activity in leaf tissue of a plant regenerated from cotransformed callus line Y13 (right) and a nontransformed tissue culture derived plant (left). Bar=1 cm. (D) Light micrograph of the leaf segment from a Y13 plant shown in (C), observed in surface view under bright field optics. GUS activity was observed in many cell types throughout the leaf tissue (magnification= 230 X). (E) Light micrograph as in (D) of control leaf.

J. Assays for Integration of Exogenous DNA and Expression of DNA in $R_o$ $R_1$ Plants Studies were undertaken to determine the expression of the transformed gene(s) in transgenic $R_o$ and $R_1$ plants. Functional activity of PAT was assessed by localized application of a commercial herbicide formulation containing PPT to leaves of SC82 $R_o$ and $R_1$ plants. No necrosis was observed on leaves of $R_o$ plants containing either high levels (E2/E5), or low levels (E3/E4) of PAT. Herbicide-treated E3/E4/E6 and control leaves are shown in FIG. 10A. Herbicide was also applied to leaves of E2/E5 progeny segregating for bar. As demonstrated in FIG. 10B, leaves of $R_1$ plants expressing bar exhibited no necrosis six days after application of the herbicide while $R_1$ plants without bar developed necrotic lesions. No necrosis was observed on transformed leaves up to 30 days post-application.

Twenty-one $R_o$ plants, representing each of the four regenerable transformed SC82 callus lines, were also analyzed for expression of the bar gene product, PAT, by thin-layer chromatographic techniques. Protein extracts

TABLE 4

EFFECTS OF PROGRESSION OF MEDIA ON THE NUMBER OF PLANTS REGENERATED (SC82)*

| CELL LINE | 227B 142 101 501 | 227B 173 101 501 | 227B 171 101 501 | 227B 227A 205 101 501 | 227B 227A 209 101 501 | 227B 227A 173 101 501 | 227B 171 473 101 501 | 227B 52 173 101 501 | 227B 52 173 101 501 | 227B 52 171 101 501 | 227B 201B 171 173 101 501 | 227B 201B 173 101 501 | 227B 201B 227B 178 101 501 | 227B 201B 205 171 101 501 | 227B 201B 227B 177 101 501 | 227B 201B 205 1 177 101 501 | 227B 201B 201B 1 178 101 501 | 227B 201B 201B 52 171 101 501 | # OF PLANTS |
|---|---|---|---|---|---|---|---|---|---|---|---|---|---|---|---|---|---|---|---|
| B3-14-4 | 1 | X | 14 | X | X | X | 1 | 1 | X | 2 | X | X | 5 | X | 5 | X | X | X | 29 |
| B3-14-9 | X | X | 1 | 1 | X | 4 | 1 | X | X | X | X | X | X | 1 | X | 1 | X | X | 9 |
| B3-14-7 | X | X | X | X | X | X | X | X | X | 6 | 2 | X | X | X | X | X | 1 | 9 |
| B3-14-6 | X | X | X | X | 1 | X | X | X | X | X | X | X | X | X | X | X | X | X | 1 |
| B3-14-3 | X | X | X | X | X | X | X | X | X | X | X | X | X | X | X | X | X | X | 0 |
| B3-14-2 | X | X | X | X | X | X | X | X | X | X | X | X | X | X | X | X | X | X | 0 |
| B3-14-1 | X | X | X | X | X | X | X | X | X | X | X | X | X | X | X | X | X | X | 0 |
| B3-14-5 | X | X | X | X | X | X | X | X | X | X | X | X | X | X | X | X | X | X | 0 |
| B3-13-5 | X | X | X | X | X | X | X | X | X | X | X | X | X | X | X | X | X | X | 0 |
| B3-13-2 | X | 1 | 13 | X | X | X | 3 | 2 | 2 | X | X | X | X | X | 1 | X | X | X | 22 |
| B3-13-1 | X | 3 | X | 1 | X | X | X | X | 1 | X | X | X | X | X | X | 1 | X | X | 6 |
| TOTAL | 1 | 4 | 28 | 2 | 1 | 4 | 5 | 3 | 3 | 2 | 6 | 2 | 5 | 1 | 6 | 1 | 1 | 1 | 76 |

* = See table 1 for media codes.
X = This media progression was either attempted and unsuccessful or not attempted.
227A = 227 with $10^{-7}$ M ABA.
227B = 227 with 1 mg/l bialaphos.

Prior to regeneration, the callus was transferred to either a) an N6-based medium containing either dicamba or 2,4-D or b) an MS-based medium containing 2,4-D. These steps allowed further embryoid development prior to maturation. Most of the maturation media contained high BAP levels (5–10 mg/l) to enhance shoot development and cause proliferation. An MS-based medium with low 2,4-D (0.25 mg/l) and high BAP (10 mg/l), as described by Shillito, et al., 1989, was found to be quite effective for regeneration.

Likewise, an MS-based medium containing 1 μm NAA, 1 μm IAA, 2 μm 2-IP, and 5 mg/l BAP (modified from Congar, et al., 1987) also promoted plant regeneration of these transformants. After plantlets recovered by any of the regenerative protocols had grown to five cm, they were transferred to a nutrient solution described by Clark, 1982, which was from the leaves of the plants were tested. PAT activity of one plant regenerated from each callus line is shown in FIG. 5.

All 21 plants tested contained PAT activity. Furthermore, activity levels were comparable to levels in the callus lines from which the plants were regenerated. The nontransformed plant showed no PAT activity (no band is in the expected position for acetylated PPT in the autoradiograph from the PAT chromatogram). A band appears in the BMS lane that is not in lanes containing protein extracts from the plant leaves. This extra band was believed to be an artifact.

As another method of confirming that genes had been delivered to cells and integrated, genomic (chromosomal) DNA was isolated from a nontransformed plant, the four regenerable callus lines and from two $R_o$ plants derived from each callus line. FIG. 6 illustrates results of gel blot analysis of genomic DNA from the four transformed calli (C) and the $R_o$ plants derived from them. The transformed callus and all plants regenerated from transformed callus contained sequences that hybridized to the bar probe, indicating the presence of DNA sequences that were complementary to bar. Furthermore, in all instances, hybridization patterns observed in plant DNA were identical in pattern and intensity to the hybridization profiles of the corresponding callus DNA.

DNA from E3/E4/E6 callus and the desired $R_o$ plants contained approximately twenty intact copies of the 1.9 kb bar expression unit (Cauliflower Mosaic Virus 35S promoter-bar-Agrobacterium transcript 7 3'-end) as well as numerous other bar-hybridizing fragments. E11 callus and plant DNA contained 1–2 copies of the intact expression unit and 5–6 additional non-intact hybridizing fragments. E10 callus and plants contained 1–2 copies of the intact bar expression unit. E2/E5 DNA contained a single fragment of approximately 3 kb that hybridized to the probe. To confirm that the hybridizing sequence observed in all plants were integrated into the chromosomal DNA, undigested genomic DNA from one plant derived from each independent transformant was analyzed by DNA gel blot hybridization. Hybridization to bar was observed only in high molecular weight DNA providing evidence for the integration of bar into the maize genome.

Figure 10B:
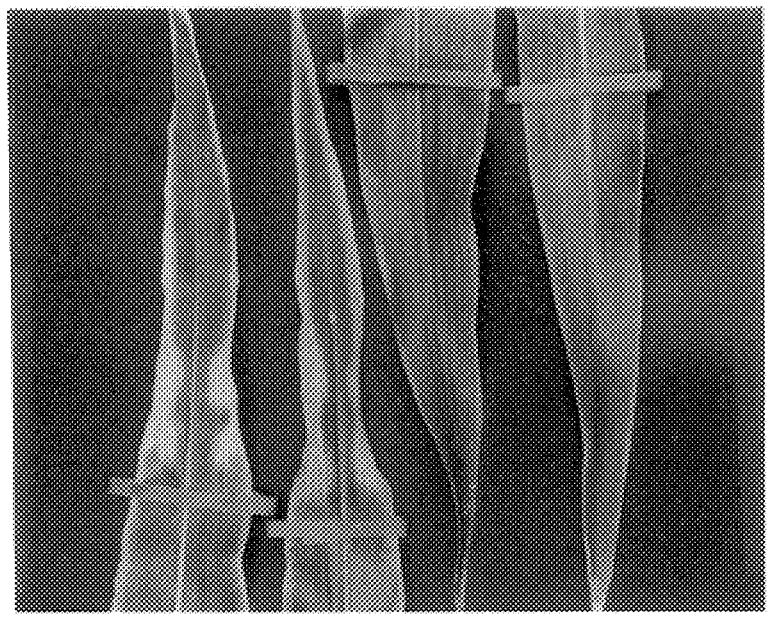
Figure 10C:
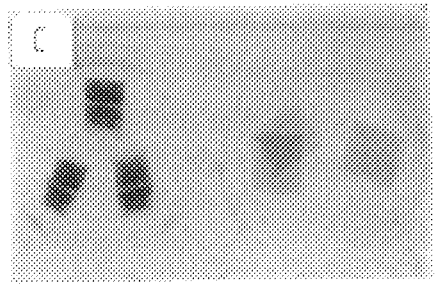
Figure 10D:
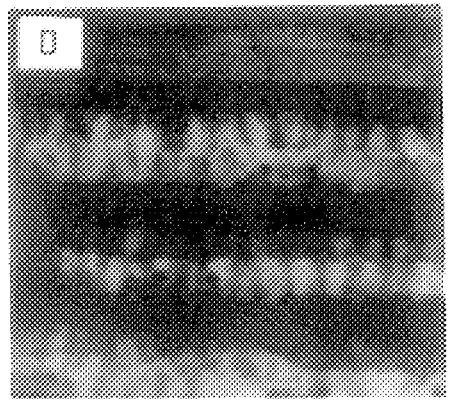
Figure 10E:
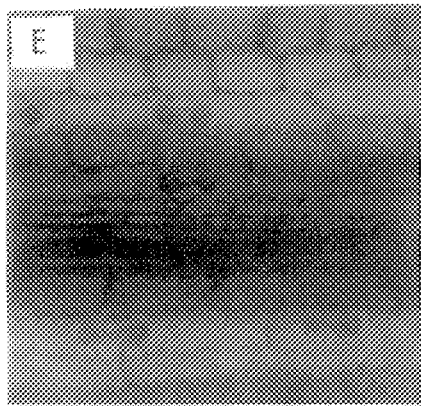

Plants were regenerated from the coexpressing callus line, Y13, shown in FIG. 8. Plants regenerated from Y13 (experiment #6, Table 2) were assayed for GUS activity and histochemically stained leaf tissue from one plant is shown in FIGS. 10C, D, E. Numerous cell types including epidermal, guard, mesophyll and bundle sheath cells stained positive for GUS activity. Staining intensity was greatest in the vascular bundles. Although all leaf samples from the regenerated plants tested (5/5) expressed the nonselected gene, some non-expressing leaf sectors were also observed. Leaf tissue extracts from three Y13 and three control plants were also assayed for GUS activity by fluorometric analysis (Jefferson, 1987). Activity detected in two opposing leaves from each of three Y13 plants tested was at least 100-fold higher than that in control leaves.

EXAMPLE 8

General Methods for Assays

A method to detect the presence of phosphinothricin acetyl transferase (PAT) activity is to use thin layer chromatography.

An example of such detection is shown in FIG. 5 wherein various protein extracts prepared from homogenates of potentially transformed cells, and from control cells that have neither been transformed nor exposed to bialaphos selection, are assayed by incubation with PPT and $^{14}C$-Acetyl Coenzyme A. 25 µg of protein extract were loaded per lane. The source in lanes E1-E11 were SC82 transformants; B13 is a BMS (Black Mexican Sweet corn nonembryogenic) bar transformant. E0 is a nonselected, nontransformed control.

As can be seen at the position indicated by the arrow (the position expected for the mobility of $^{14}C$-N-AcPPT), all lanes except the nontransformed control have activities with the appropriate mobility. Variation in activity among the transformants was approximately 10 fold, as demonstrated by the relative intensity of the bands. The results of this assay provide confirmation of the expression of the bar gene which codes for PAT. For analysis of PAT activity in plant tissue, 100–200 mg of leaf tissue was extracted in sintered glass homogenizers and assayed as described previously.

GUS activity was assessed histochemically as described using 5-bromo-4-chloro-3-indolyl glucuronide (Jefferson, 1987); tissue was scored for blue cells 18–24 h after addition of substrate. Fluorometric analysis was performed as described by Jefferson (1987) using 4-methyl umbelliferyl glucuronide.

DNA gel blot analysis was performed as follows. Genomic DNA was isolated using a procedure modified from Shure, et al., 1983. Approximately 1 gm callus tissue was ground to a fine powder in liquid N2 using a mortar and pestle. Powdered tissue was mixed thoroughly with 4 ml extraction buffer (7.0M urea, 0.35M NaCl, 0.05M Tris-HCl pH 8.0, 0.01M EDTA, 1% sarcosine). Tissue/buffer homogenate was extracted with 4 ml phenol/chloroform. The aqueous phase was separated by centrifugation, passed through Miracloth, and precipitated twice using 1/10 volume of 4.4M ammonium acetate, pH 5.2 and an equal volume of isopropanol. The precipitate was washed with 70% ethanol and resuspended in 200–500 µl TE (0.01M Tris-HCl, 0.001M EDTA, pH 8.0). Plant tissue may also be employed for the isolation of DNA using the foregoing procedure.

Genomic DNA was digested with a 3-fold excess of restriction enzymes, electrophoresed through 0.8% agarose (FMC), and transferred (Southern, 1975) to Nytran (Schleicher and Schuell) using 10×SCP (20×SCP: 2M NaCl, 0.6M disodium phosphate, 0.02M disodium EDTA). Filters were prehybridized at 65° C. in 6×SCP, 10% dextran sulfate, 2% sarcosine, and 500 µg/ml heparin (Chomet, et al., 1987) for 15 min. Filters were hybridized overnight at 65° C. in 6×SCP containing 100 µg/ml denatured salmon sperm DNA and $^{32}P$-labeled probe. The 0.6 kb SmaI fragment from pDPG165 and the 1.8 kb BamHI/EcoRI fragment from pCEV5 were used in random priming reactions (Feinberg and Vogelstein, 1983; Boehringer-Mannheim) to generate labeled probes for detecting sequences encoding PAT or GUS, respectively. Filters were washed in 2×SCP, 1% SDS at 65° C. for 30 min. and visualized by autoradiography using Kodak XAR5 film. Prior to rehybridization with a second probe, the filters were boiled for 10 min. in distilled $H_2O$ to remove the first probe and then prehybridized as described above.

EXAMPLE 9

Herbicide Application

The herbicide formulation used, Basta TX$^R$, contains 200 g/l glufosinate, the ammonium salt of phosphinothricin. Young leaves were painted with a 2% Basta solution (v/v) containing 0.1% (v/v) Tween-20. The prescribed application rate for this formulation is 0.5–1%.

In FIG. 10A, Basta$^R$ solution was applied to a large area (about 4×8 cm) in the center of leaves of a nontransformed A188×B73 plant (left) and a transgenic $R_o$ E3/E4/E6 plant (right). In FIG. 10B, Basta was also applied to leaves of four $R_1$ plants; two plants without bar and two plants containing bar. The herbicide was applied to $R_1$ plants in 1 cm circles to four locations on each leaf, two on each side of the midrib. Photographs were taken six days after application.

K. Fertility of Transgenic Plants

To recover progeny the regenerated, genetically transformed maize plants (designated $R_o$), were backcrossed with pollen collected from nontransformed plants derived from seeds, and progeny (designated $R_1$) that contained and expressed bar were recovered.

An important aspect of this invention is the production for the first time of fertile, genetically transformed maize plants ($R_o$) and progeny ($R_1$). These were regenerated from embryogenic cells that were transformed. $R_1$ plants are those resulting from backcrossing of $R_o$ plants.

Pollination of transgenic $R_o$ ears with non-transformed B73 pollen resulted in kernel development. In addition, kernels developed from pistillate flowers on male inflorescences that were pollinated with non-transformed B73 pollen. Kernels on transformed $R_o$ plants from SC82 developed normally for approximately 10–14 days post-pollination but after this period the kernels ceased development and often collapsed. Most plants exhibited premature senescence at this time. A total of 153 kernels developed sporadically on numerous plants (see Table 5): 8 of 37 E2/E5 plants, 2 of 22 E10 plants, and 3 of 6 E11 plants. Viable progeny were recovered by embryo rescue from 11 E2/E5 plants and one E10 plant.

was analyzed by DNA gel blot hybridization for the presence of bar as shown in FIG. 7B. The six progeny tested that expressed PAT contained a single copy of bar identical in mobility to that detected in callus and $R_o$ plants; the four PAT-negative progeny tested did not contain bar-hybridizing sequences. In one series of assays, the presence of the bar gene product in 18 of 36 progeny indicates a 1:1 segregation of the single copy of bar found in E2/E5 $R_o$ plants and is consistent with inheritance of PAT expression as a single dominant trait. A dominant pattern of inheritance would indicate the presence in the plant of at least one copy of the gene coding for PAT. The single progeny recovered from an E10 $R_o$ plant tested positive for PAT activity.

It was determined that the methods disclosed in this invention resulted in transformed $R_o$ and $R_1$ plants that produced functionally active PAT. This was determined by

TABLE 5

Regenerated Plants ($R_o$) and progeny ($R_1$)

| Exp # | Culture Bombarded | # of Independent bar Transformants Recovered | # of Regenerable Transformed Callus Lines | # of $R_o$ Plants | # Reaching Maturity | # of $R_o$ Producing Kernels | # of Kernels Recovered | # of $R_1$ Plants |
|---|---|---|---|---|---|---|---|---|
| 1, 2 | SC82 | 7 | 4 | 76 | 73 | 23 | 153 | 40 |
| 4, 5 | SC716 | 20 | 10 | 219 | (35) | (9) | (51) | (31) |
| 3 | SC94 | 8 | 2ᵃ | 11ᵃ | (0) | (0) | (0) | (0) |
| 6 | SC82 | 19 | 4ᵃ | 23ᵃ | (0) | (0) | (0) | (0) |

ᵃRegeneration in progress.
() Experiment still in progress, data still being collected.

SC716 $R_o$ plants were also backcrossed with seed-derived B73 plants. To date, from the 35 mature SC716 $R_o$ plants nine plants (representing four independent callus lines) yielded 51 kernels, 31 of which produced vigorous $R_1$ seedlings (Table 5). Most kernels that developed on SC716 plants did not require embryo rescue. Kernels often developed for 30–40 days on the plant and some were germinated in soil. The remaining seed was germinated on MS-based medium to monitor germination and transferred to soil after a few days. In addition to the improved kernel development observed on SC716 $R_o$ plants relative to SC82 $R_o$ plants, pollen dehisced from anthers of several SC716 plants and some of this pollen germinated in vitro (Pfahler 1967). Transmission of the foreign gene has occurred both through SC716 $R_1$ ears and using SC716 $R_1$-derived pollen on non-transformed ears.

Figure 11A:
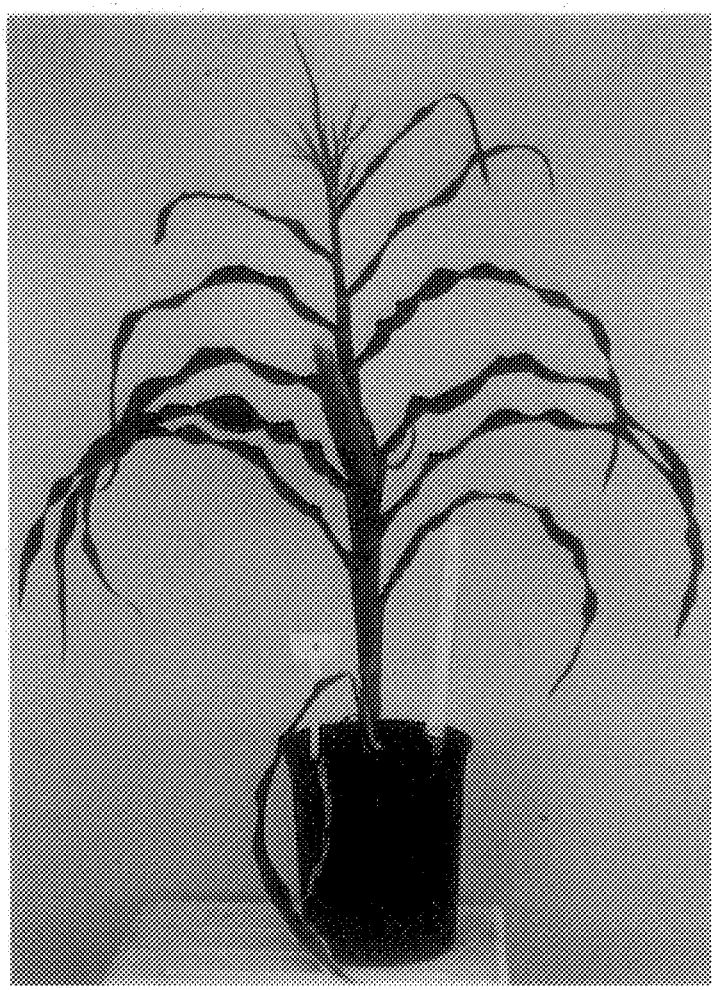
FIG. 11. Mature $R_o$ Plant, Developing Kernels and Progeny. (A) Mature transgenic $R_o$ plant regenerated from an E2/E5 callus. (B) Progeny derived from an E2/E5 plant by embryo rescue; segregant bearing the resistance gene on the right, and lacking the gene on the left. (C) Using pollen from transformed $R_1$ plants to pollinate B73 ears, large numbers of seed have been recovered. (D) A transformed ear from an $R_1$ plant crossed with pollen from a non-transformed inbred plant.
Figure 11B:
Figure 11C:
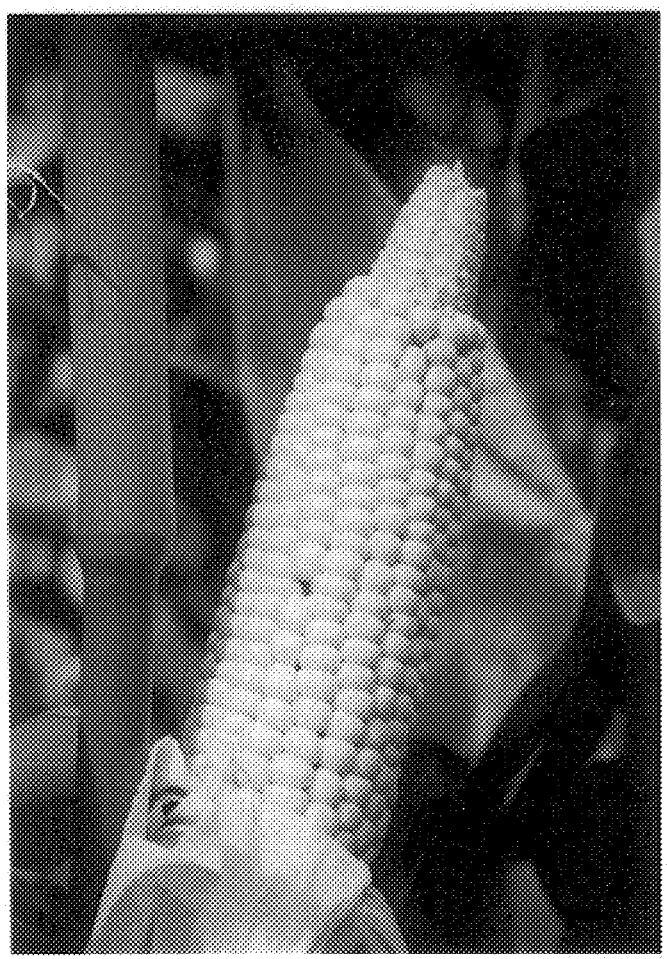
Figure 11D:
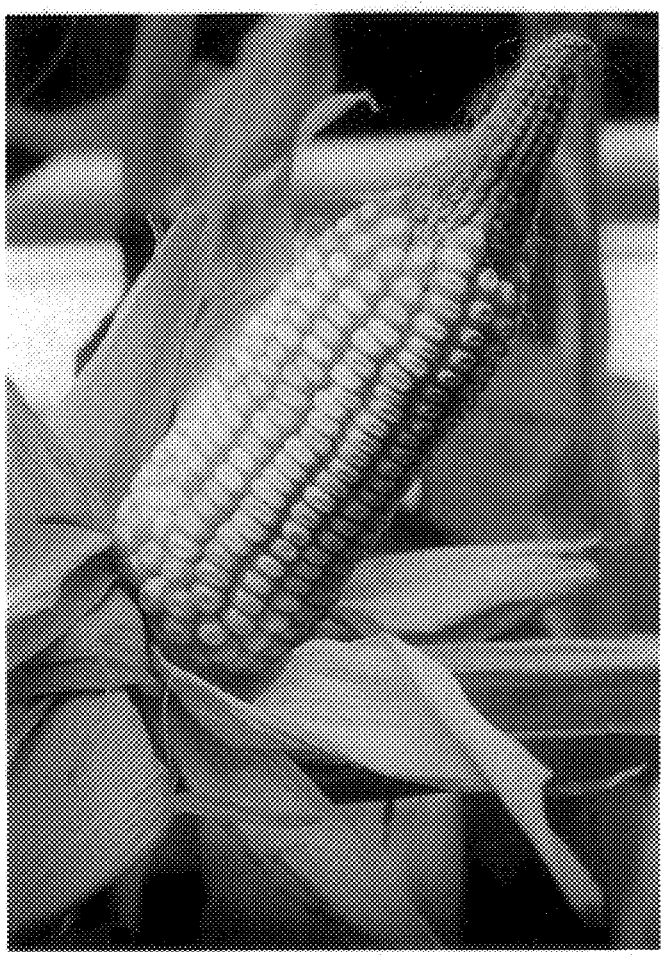

Pollen obtained from transformed $R_1$ plants has now been successfully employed to pollinate B73 ears and a large number of seeds have been recovered (see FIG. 11C). Moreover, a transformed ear from an $R_1$ plant crossed with pollen from a non-transformed inbred plant is shown in FIG. 11D. The fertility characteristics of the $R_1$ generation has been confirmed both from a standpoint of the pollen's ability to fertilize non-transformed ears, and the ability of $R_1$ ears to be fertilized by pollen from non-transformed plants.

EXAMPLE 10

Analysis of Progeny ($R_1$) of Transformed $R_o$ Plants for PAT and bar

Figure 7A:
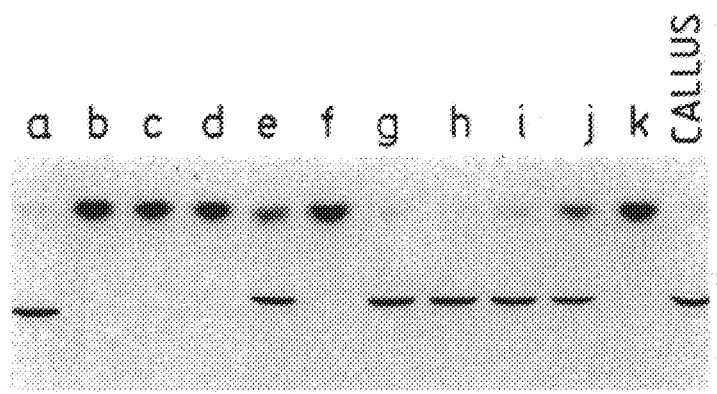
FIG. 7. PAT Activity and DNA Gel Blot Analysis of Segregating Progeny of E2/E5 $R_o$ Plants. (A) Analysis of PAT activity in ten progeny (lanes a–j) and a nontransformed control plant (lane k). Lanes designated a, b–h, i, and j contained protein extracts from progeny of separate parental $R_o$ plants. The lane designated callus contained protein extract from E2/E5 callus. Approximately 25 micrograms of total protein were used per reaction. (B) DNA gel blot analysis of genomic DNA isolated from the ten progeny analyzed in A. Genomic DNA (5 µg/lane) was digested with SmaI, which releases a 0.6 kb fragment containing bar from pDPG165, and hybridized with bar probe. The lane designated $R_o$ contained DNA from the $R_o$ parent of progeny a. The lane designated 1 copy contained pDPG165 digested with SmaI to represent approximately 1 copy of the 0.6 kb fragment per diploid genome (0.8 pg).

A total of 40 progeny of E2/E5 $R_o$ plants were analyzed for PAT activity, ten of which are shown in FIG. 7A. Of 36 progeny which were assayed, 18 had PAT activity. Genomic DNA from the same ten progeny analyzed for PAT activity applying Basta (PPT) to the leaves of plants and determining whether necrosis (tissue destruction) resulted from this application. If functionally active PAT is produced by the plants, the leaf tissue is protected from necrosis. No necrosis was observed on $R_o$ plants expressing high levels of PAT (E2/E5) or on plants expressing low levels (E3/E4/E6) (FIG. 10A).

Herbicide was also applied to leaves of $R_1$ progeny segregating for bar. In these studies, no necrosis was observed on $R_1$ plants containing and expressing bar, however, necrosis was observed on those $R_1$ plants lacking the bar gene. This is shown in FIG. 10B.

Segregation of bar did not correlate with the variability in phenotypic characteristics of $R_1$ plants such as plant height and tassel morphology. In FIG. 9B, the plant on the right contains bar, the plant on the left does not. In addition, most of the $R_1$ plants were more vigorous than the $R_o$ plants.

Of the 23 $R_1$ seedlings recovered to date from the SC716 transformants, ten of 16 had PAT activity. PAT activity was detected in four of ten progeny from $R_o$ plants representing callus line R18 and six of six progeny from $R_o$ plants representing callus line R9.

L. Embryo Rescue

In cases where embryo rescue was required, developing embryos were excised from surface disinfected kernels 10–20 days post-pollination and cultured on medium containing MS salts, 2% sucrose and 5.5 g/l Seakem agarose. Large embryos (>3 mm) were germinated directly on the medium described above. Smaller embryos were cultured for approximately 1 week on the above medium containing $10^{-5}$M abscisic acid and transferred to hormone-free medium for germination. Several embryos became bacterially contaminated; these embryos were transferred to medium containing 300 μg/ml cefoxitin. Developing plants were subsequently handled as described for regeneration of $R_o$ plants.

EXAMPLE 11

Embryo Rescue

Viable progeny, recovered from seven SC82 E2/E5 plants and one SC82 E10 plant, were sustained by embryo rescue. This method consisted of excising embryos from kernels that developed on $R_o$ plants. Embryos ranged in size from about 0.5 to 4 mm in length. Small embryos were cultured on maturation medium containing abscisic acid while larger embryos were cultured directly on germination medium. Two of the approximately forty viable progeny thus far recovered from SC82 $R_o$ plants are shown in FIG. 11B.

M. Phenotype of Transgenic Plants

Most of the $R_o$ plants regenerated from SC82 transformants exhibited an A188×B73 hybrid phenotype. Plants were similar in height to seed derived A188 plants (3–5 feet) but had B73 traits such as anthocyanin accumulation in stalks and prop roots, and the presence of upright leaves. Many plants, regardless of the callus line from which they were regenerated, exhibited phenotypic abnormalities including leaf splitting, forked leaves, multiple ears per node, and coarse silk. Although many of the phenotypic characteristics were common to all $R_o$ plants, some characteristics were unique to plants regenerated from specific callus lines. Such characteristics were exhibited regardless of regeneration route and the time spent in culture during regeneration.

Nontransformed control plants were not regenerated from this culture and, therefore, cannot be compared phenotypically. Pistillate flowers developed on tassels of one E11 (1/6), several E10 (3/22) and almost one-third of the E2/E5 (12/37) plants with a range of three to approximately twenty ovules per tassel. Primary and secondary ears developed frequently on most E2/E5, E10, and E11 plants; a mature E2/E5 plant is shown in FIG. 11A. Anthers rarely extruded from the tassels of plants regenerated from SC82 transformants and the limited number of anthers which were extruded did not dehisce pollen. Some phenotypic characteristics observed were unique to plants regenerated from a specific callus line such as the lack of ears on E3/E4/E6 plants and a "grassy" phenotype (up to 21 lone narrow leaves) exhibited by all E11 plants.

All SC82 plants senesced prematurely; leaf necrosis began approximately two weeks after anthesis. The $R_o$ plants regenerated from SC82 transformed cell lines have tended to senesce prematurely; typically before the developing kernels were mature. This has necessitated the use of embryo rescue to recover progeny ($R_1$ generation). Segregation of bar in the $R_1$ generation does not correlate with the variability in phenotypic characteristics of $R_1$ plants such as plant height and tassel morphology. In FIG. 11B, the plant on the right contains bar, the plant on the left does not. In addition, most of the $R_1$ plants are more vigorous than the $R_o$ plants. Transformed progeny (R1) have now also begun to yield kernels and R2 plantlets have been recovered.

Of 219 plants regenerated from 10 independent SC716 transformants, approximately 35 have reached maturity (Table 5). The SC716 plants did not exhibit the phenotypic differences which characterized the individual callus lines of SC82. These plants were more uniform and abnormalities less frequent. The phenotype of these plants closely resembled that of control plants regenerated from a SC716 cryopreserved culture which was not bombarded. Plant height ranged from three to six feet with the majority of the plants between five and six feet. Most mature plants produced large, multi-branched tassels and primary and secondary ears. Pistillate flowers also developed on tassels of several SC716 plants. Although anther extrusion occurred at approximately the same low frequency as in the SC82 plants, a small amount of pollen dehisced from some extruded anthers. For most of the SC716 plants that reached maturity, senescence did not commence until at least 30 days after anthesis. The improved characteristics of SC716 plants over SC82 plants indicate that differences between the suspension cultures may be responsible.

While the invention is susceptible to various modifications and alternative forms, specific embodiments thereof have been shown by way of example in the drawings and herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

REFERENCES

The references listed below are incorporated herein by reference to the extent that they supplement, explain, provide a background for, or teach methodology, techniques, and/or compositions employed herein.

Reference 1. Armstrong C. L., Green C. E. (1985). *Planta* 164:207–214.

Reference 2. Bottino P. J., (1975). *Botany* 15:1–16.

Reference 3. Carlsson J., Drevin H., Axen R. (1978). *Biochem J.* 173:723.

Reference 4. Chomet P. S., Wessler S., Dellaporta S. L. (1978). *EMBO J* 6:295–302.

Reference 5. Chu C. C., Wang C. C., Sun C. S., Hsu C., Yin K. C., Chu C. Y., Bi F. Y. (1975). *Scientia Sinica* 18:659–668.

Reference 6. Clark, R. (1982). *J. of Plant Nutrition* 5:1039.

Reference 7. Comai L., Gacciotti D., Hiatt W. R., Thompson G., Rose R. E., Stalker D. (1985). *Nature* 317:741–744; Conger, B. V., Novak, F. J., Afza, R., Erdelsky, K. (1987), *Plant Cell Rep* 6:345–347

Reference 8. Cristou P., McCabe D. E., Swain W. F. (1988). *Plant Physiol* 87:671–674.

Reference 9. DE 3642 B29 A

Reference 10. De Block, M., Botterman J., Vandiwiele M., Dockx J., Thoen C., Gossele V, Movva N. R., Thompson C., Van Montagu M., Leemans J. (1987). *EMBO J.* 6:2513–2518; see also PCT Publication number WO 87/05629, published Sep. 24, 1987.

Reference 11. De Block, M., Botterman J., Vandiwiele M., Dockx J., Thoen C., Gossele V, Movva N. R., Thompson C., Van Montagu M., Leemans J. (1989). *Plant Physiol* 91:694–701.

Reference 12. Dekeyser R., Claes B., Marichal M., Van Montagu M., Caplan A. (1989). *Plant Physiol* 90:217–223.

Reference 13. Delannay X., LaVallee B. J., Proksch R. K., Fuchs R. L., Sims S.R., Greenplate J. R., Marrone P. G., Dodson R. B., Augustine J. J., Layton J. G., Fischhoff D. A. (1989). *Bio/Technol* 7:1265–1269.

Reference 14. Feinberg A. P., Vogelstein B. (1983). *Anal Biochem* 132:6–13.

Reference 15. Finkle B. J., Ulrich J. M., Rains W., Savarek S. J. (1985). *Plant Sci* 42:133–140.

Reference 16. Fischhoff D. A., Bowdish K. S., Perlak F. J., Marrone P. G., McCormick S. M., Niedermeyer J.

G., Dean D. A., Kusano-Kretzmer K., Mayer E. M., Rochester D. E., Rogers S. G., Fraley R. T. *Bio/Technol* 5:807–813.

Reference 17. Fromm M. E., Taylor L. P., Walbot V. (1986). *Nature* 312:791–793.

Reference 18. Haughn G. W., Smith J., Mazur B., Somerville, C. (1988). *Mol Gen Genet* 211:266–271.

Reference 19. Hauptmann R. M., Vasil V., Ozias-Aikins P., Tabaeizadeh Z., Rogers S. G., Fraley R. T., Horsch R. B., Vasil I. K. (1988). *Plant Physiol* 86:602–606.

Reference 20. IPRF European Patent Application No. 90033A

Reference 21. Jefferson R. A. (1987). *P1 Mol Biol Repr* 5:387–405.

Reference 22. Klein T. M., Kornstein L., Sanford J. C., Fromm M. E. (1989). *Plant Physiol* 91:440–444.

Reference 23. Klein T. M., Kornstein L., Sanford J. C., Fromm M. E. (1987). *Nature* 327:70–73.

Reference 24. Kozak M. (1984). *Nucl Acids Res* 12:857–872.

Reference 25. Lorz H., Baker B., Schell J. (1985). *Mol Gen Genet* 199:178–182.

Reference 26. Lyznik L. A., Ryan R. D., Ritchie S. W., Hodges T. K. (1989). *Plant Mol Biol* 13:151–16.

Reference 27. McCabe D. E., Swain W. F., Martinell B. J., Cristou P. (1988). *Bio/Technol* 6:923–926.

Reference 28. McDaniel C. N., Poethig R. S. (1988). *Planta* 175:13–22.

Reference 29. Murakami T., Anzai H., Imai S., Satoh A., Nagaoka K., Thompson C. J. (1986). *Mol Gen Genet* 205:42–50.

Reference 30. Murashige T., Skoog F. (1962). *Physiol Plant* 15:473–497.

Reference 31. Nelson R. S., McCormick S. M., Delannay X., Dube P., Layton J., Anderson E. J., Kaniewska M., Proksch R. K., Horsch R. B., Rogers S. G., Fraley R. T. Beachy R.N. (1988). *Bio/Technol* 6:403–409.

Reference 32. Nester, E. W. et al., (1984). *Ann. Rev. Plant Physiol* 35:387–413.

Reference 33. Ogawa, Y. et al (1973). *Sci. Rep., Meija Seika* 13:42–48.

Reference 34. PCT No. WO 87/-00141

Reference 35. Pfahler P. L. (1967). *Can J. Bot* 45:836–845.

Reference 36. Potrykus I. (1989) *Trends Biotechnol* 7:269–273.

Reference 37. Prioli L. M., Sondahl M. R. (1989). *Bio/Technol* 7:589–594.

Reference 38. Rhodes C. A., Pierce D. A., Mettler I. J., Mascarenhas D., Detmer J. J. (1988). *Science* 240:204–207.

Reference 39. Shillito R. D., Carswell G. K., Johnson C. M., DiMaio J. J., Harms C. T. (1989). *Bio/Technol* 7:581–587.

Reference 40. Shah D. M., Horsch R. B., Klee H. J., Kishore G. M., Winter J. A., Tumer N.E., Hironaka C. M., Sanders P. R., Gasser C. S., Aykent S., Siegel N. R., Rogers S. G., Fraley R. T. (1986). *Science* 233:478–481.

Reference 41. Shimamoto K., Terada R., Izawa T., Fujimoto H. (1989). *Nature* 338:274–276.

Reference 42. Shure M., Wesler S., Federoff, N. (1983). *Cell* 35:225–233.

Reference 43. Southern E. M. (1975). *J Mol Biol* 98:503–517.

Reference 44. Szoka, U.S. Pat. No. 4,394,448

Reference 45. Thompson C. K., Movva N. R., Tizard R., Crameri R., Davies J. E., Lauwereys M., Botterman J. (1987). *EMBO J* 6:2519–2623.

Reference 46. Tomes D. (1990). Annual Meting Proceedings, 26th Annual Corn Breeders School, University of Illinois, Feb. 26–27, pp. 7–9.

Reference 47. Twell D., Klein T. M., Fromm M. E., McCormick S. (1989). *Plant Physiol* 91:1270–1274.

Reference 48. Vaeck M., Reynaerts A., Hofte H., Jansens S., De Beuckeleer M., Dean C., Zabeau M., Van Montagu M., Leemans J. (1987). *Nature* 328:33–37.

Reference 49. Withers L. A., King P. J. (1979). *Plant Physiol* 64:675–678.

Reference 50. Wong, Y. C. et al. (1988). *Plant Mol Biol* 11:433–439.

Reference 51. Yang H., Zhang M. H., Davey M. R., Mulligan B. J., Cocking E. C. (1988). *Plant Cell Rep* 7:421–425.

Reference 52. Zhang M. H., Yang H., Rech E. L., Golds T. J., David A. S., Mulligan B. J., Cocking E. C., Davey E. R. (1988). *Plant Cell Rep* 7:379–384.

Reference 53. White, J., Chang, S. P., Bibb, M. J., Bibb, M. J. (1990), *Nucl Acids Res,* 18:1062.

Reference 54. Zukowsky et al. (1983), *Proc. Natl. Acad. Sci. USA* 80:1101–1105.

Reference 55. Katz et al. (1983) *J. Gen. Microbiol.* 129:2703–2714.

Reference 56. Doring, H. P. and Starlinger (1986), *Ann. Rev. Genet.* 20:175–200

Reference 57. Federoff, N. (1989), "Maize Transposable Elements", in *Mobile DNA*. Wowe, M. M. and Berg, D. E., eds., Amer. Soc. Microbiol., Wash., D.C., pp. 377–411.

Reference 58. Shapiro, J. A. (1983), *Mobile Genetic Elements,* Academic Press, N.Y.

Reference 59. Dellaporta, S. L., Greenblatt, I. M., Kermicle, J., Hicks, J. B., and Wessler, S. (1988), *Stadler Symposium* 11:263–282.

Reference 60. European Patent Application 154,204 (Sep. 11, 1985).

Reference 61. Stief, A., Winter, D., Stratling, W. H., and Sippel, A. E. (1989), *Nature* 341:343.

Reference 62. Phi-Van, L., Kries, J. P., Ostertag, W., Stratling, W. H. (1990), *Mol Cell Biol* 10:2302–2307.

Reference 63. Coe, E. H., Neuffer, M. G., and Hoisington, D. A. (1988), in *Corn and Corn Improvement,* Sprague, G. F. and Dudley, J. W., eds., pp. 81–258

Reference 64. Johnson, R., Norvdez, J., An, G, and Ryan, C. (1989), *Proc. Natl. Acad. Sci. USA* 86:9871–9875

Reference 65. Hammock, B. D., Bonning, B. C., Possee, R. D., Hanzlik, T. N., and Maeda, S. (1990), *Nature* 344:458–461

Reference 66. Berg, D. E., Egner, C., Hirschel, B. J., Howard, J., Jorgensen, R., and Tisty, T. D. (1980) *Cold Spring Harbor Symposium* 45:448–465

Reference 67. Hinchee, M. A. W., Connor-Ward, D. V., Newell, C. A., McDonell, R. E., Sato, S. J., Gasser, C. S., Fischhoff, D. A., Re, C. B., Fraley, R. T., Horsch, R. B. (1988) *Bio/technol* 6:915–922.

Reference 68. Odell, J. T., Nagy, F., Chua, N. H. (1985) *Nature* 313:810–812.

Reference 69. Lawton, M. A., Tierney, M. A., Nakamura, I., Anderson, E., Komeda, Y., Dube, P., Hoffman, N., Fraley, R. T., Beachy, R.N. (1987), *Plant Mol. Biol.* 9:315–324.

Reference 70. Ebert, P. R., Ha, S. B., An. G. (1987), *PNAS* 84:5745–5749.

Reference 71. Walker, J. C., Howard, E. A., Dennis, E. S., Peacock, W. J. (1987), *PNAS* 84:6624–6628.

Reference 72. Yang, N. S., Russell, D. (1990), *PNAS* 87:4144–4148.

Reference 73. Conkling, M. A., Cheng, C. L., Yamamoto, Y. T., Goodman, H. M. (1990), *Plant Physiol.* 93:1203–1211.

Reference 74. Fromm, H., Katagiri, F., Chua, N. H. (1989), *The Plant Cell* 1:977–984.

Reference 75. Ingelbrecht, I. L. W., Herman, L. M. F., Dekeyser, R. A., Van Montagu, M. C., Depicker, A. G. (1989), *The Plant Cell* 1:671–680; Bevan, M., Barnes, W. M., Chilton, M. D. (1983), *Nucleic Acid Res.* 11:369–385.

Reference 76. Callis, J., Fromm, M., Walbot, V. (1987), *Genes and Develop.* 1:1183–1200.

Reference 77. Vasil, V., Clancy, M., Ferl, R. J., Vasil, I. K., Hannah, L. C. (1989), *Plant Physiol.* 91:1575–1579.

Reference 78. Gallie, D. R., Lucas, W. J., Walbot, V. (1989), *The Plant Cell* 1:301–311.

Reference 79. Sambrook, J., Fritsch, E. F., and Maniatus, T. (1989), *Molecular Cloning, A Laboratory Manual* 2nd ed.

Reference 80. Gelvin, S. B., Schilperoort, R. A., Varma, D. P. S., eds. *Plant Molecular Biology Manual* (1990).

Reference 81. Fransz, P. F., de Ruijter, N. C. A., Schel, J. H. N. (1989), *Plant Cell Rep* 8:67–70

Reference 82. Potrykus, I., Saul, M. W., Petruska, J., Paszkowski, J., Shillito, R. D. (1985), *Mol Gen Genet* 199:183–188

Reference 83. Stalker, D. M., Malyj, L. D., McBride, K. E. (1988), *J Biol Chem* 263:6310–6314

Reference 84. Ow, D. W., Wood, K. V., DeLuca, M., dewet, J. R., Helinski, D. R., Howell, S. H. (1986) *Science* 234:856–859

Reference 85. Ikatu, N., Souza, M. B. N., Valencia, F. F., Castro, M. E. B., Schenberg A. C. G., Pizzirani-Kleiner, A., Astolfi-Filho, S. (1990), *Bio/technol* 8:241–242

Reference 86. Watrud, L. S., Perlak, F. J., Tran, M.-T., Kusano, K., Mayer, E. J., Miller-Widemann, M. A., Obukowicz, M. G., Nelson, D. R., Kreitinger, J. P., and Kaufman, R. J. (1985), in *Engineered Organisms and the Environment,* H. O. Halvorson et al., eds., Am. Soc. Microbiol., Washington, D.C.

Reference 87. Cutler, A. J., Saleem, M., Kendell, E., Gusta, L. V., Georges, F., Fletcher, G. L. (1989), *J Plant Physiol* 135:351–354.

Reference 88. Hilder, V. A., Gatehouse, A. M. R., Sheerman, S. E., Barker, R. F., Boulter, D. (1987) *Nature* 330:160–163.

Reference 89. *Avermectin and Abamectin.* (1989) W. C. Campbell, ed.

Reference 90. Ikeda, H., Kotaki, H., Omura, S. (1987), *J Bacteriol* 169:5615–5621.

Reference 91. Gatehouse, A. M., Dewey, F. M., Dove, J., Fenton, K. A., Dusztai, A. (1984), *J Sci Food Agric* 35:373–380

Reference 92. Broakaert, W. F., Parijs, J., Leyns, F., Joos, H., Peumans, W. J. (1989) *Science* 245:1100–1102.

Reference 93. Barkai-Golan, R., Mirelman, D., Sharon, N. (1978) *Arch. Microbiol* 116:119–124

Reference 93. Comai, L., U.S. Pat. No. 4,535,060; and ATCC deposit 39256.

Reference 94. European Patent Application publication number 0218571 A2, published Apr. 15, 1987.

Reference 95. Thillet, J., Absil, J., Stone, S. R., Pictet, R. (1988), *J Biol Chem* 263:12500–12508

Reference 96. Chandler, V. L., Radicella, J. P., Robbins, P. P., Chen, J., Turks, D. (1989), *The Plant Cell* 1:1175–1183

Reference 97. Dellaporta, S., Greenblatt, I., Kermicle, J., Hicks, J. B., Wessler, S. (1988) in *Chromosome Structure and Function: Impact of New Concepts,* 18*th Stadler Genetics Symposium,* J. P. Gustafson and R. Appels, eds (New York: Plenum Press), pp. 263–282.

Reference 98. Sutcliffe, J. G. (1978), *Proc Natl Acad Sci USA* 75:3737–3741

---

What is claimed is:

1. A method for the production of fertile, transgenic monocotyledonous plants, said method comprising the steps of:
   (a) contacting recipient monocotyledonous cells other than maize or rice with a DNA composition comprising a phosphinothricin acetyl transferase gene under conditions of microprojectile bombardment allowing the uptake of DNA by recipient cells;
   (b) regenerating plants from recipient cells which have received the DNA component; and
   (c) identifying fertile, transgenic plants which contain the DNA component.

2. The method of claim 1, wherein said monocotyledonous cells comprise wheat, oat, or barley cells.

3. The method of claim 1, wherein said recipient cells comprise callus cells, gametic cells, or meristematic cells.

4. The method of claim 1, wherein said recipient cells comprise cells obtained from suspension culture.

5. The method of claim 4, wherein said suspension culture is prepared from an embryogenic callus.

6. The method of claim 5, wherein said callus comprises a Type II callus.

7. The method of claim 1, wherein the DNA composition comprises a transposable element.

8. The method of claim 7, wherein the transposable element comprises an Ac, Ds or Mu element.

9. The method of claim 1, wherein the DNA composition comprises plasmids.

10. The method of claim 1, wherein recipient cells which have received a DNA component are selected for prior to regeneration.

11. The method of claim 10, wherein cells are selected by incubation in contact with a selective medium.

12. The method of claim 1, wherein uptake of the DNA composition by recipient cells is achieved by passing particles on which the DNA composition has been coated through a screen and into the cells.

13. The method of claim 12, wherein the particles comprise tungsten or platinum.

14. The method of claim 1, wherein regenerating plants from recipient cells comprises the steps of:
   (a) culturing recipient cells which have received DNA in a media comprising an embryogenic promoting hormone until callus organization is observed;
   (b) transferring said cells to a media which includes a tissue organization promoting hormone;
   (c) subculturing said cells onto media without said hormones, to allow for shoot elongation or root development; and
   (d) transferring said cells onto a minimal medium, to provide for hardening of the plant.

15. The method of claim 14, wherein the embryogenic promoting hormone comprises dicamba.

16. The method of claim 14, wherein the embryogenic promoting hormone comprises 2,4-D.

17. The method of claim 14, wherein the tissue organization promoting medium comprises BAP, myoinositol and 2,4-D.

18. The method of claim 14, wherein the tissue organization promoting medium comprises ABA, BAP, NAA, IAA, 2-IP or myoinositol.

19. The method of claim 14, wherein the media employed for step (c) includes myoinositol.

20. The method of claim 14, further comprising applying to said cells a hormone to stimulate rooting.

21. The method of claim 20, wherein IBA is applied to stimulate rooting.

22. The method of claim 14, wherein the minimal media comprises Clark's media.

23. The method of claim 1, further comprising obtaining progeny of one of said fertile, transgenic plants, wherein said progeny is a fertile, transgenic plant that comprises the gene.

24. The method of claim 23, further comprising breeding said progeny with a non-transgenic plant, and obtaining therefrom an offspring fertile, transgenic monocot plant that comprises the gene.

25. The method of claim 23, further comprising breeding said progeny with a second transgenic monocot plant to prepare an offspring fertile, transgenic plant that comprises the gene.

26. The method of any one of claims 1, 23, 24, or 25, wherein the fertile, transgenic monocot plant is an inbred plant.

27. The method of claim 23, further comprising preparing seed from one or more fertile, transgenic monocot plants that comprises the gene, wherein said seed contains said component.

28. The method of claim 27, further comprising cultivating seed to prepare a fertile, transgenic monocot plant that comprises the gene.

29. The method of claim 1, wherein the DNA component comprises bar gene.

30. The method of claim 1, wherein the DNA comprises a promoter and 3' region operatively linked to a selected gene.

31. The method of claim 30, wherein said promoter comprises a CaMV 35S, CaMV 19S, nos, Adh, sucrose synthase, R-allele or root cell promoter.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GAGGATCCGT    CGACCATGGT    AAGCTTAGCG    GGCCC                           3 6

( 2 ) INFORMATION FOR SEQ ID NO:2:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (xi) SEQUENCE DESCRIPTION: SEQ ID NO:2:

GATCCGTCGA CCATGGCGCT TCAAGCTTC                                29

(2) INFORMATION FOR SEQ ID NO:3:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (xi) SEQUENCE DESCRIPTION: SEQ ID NO:3:

GCAGCTGGTA CCGCGAAGTT CGAAGGGCT                                29